US008022188B2

(12) United States Patent
Siegel et al.

(10) Patent No.: US 8,022,188 B2
(45) Date of Patent: Sep. 20, 2011

(54) IMMUNOSUPPRESSANT BINDING ANTIBODIES AND METHODS OF OBTAINING AND USING SAME

(75) Inventors: Robert W. Siegel, Beach Park, IL (US); Joan D. Tyner, Beach Park, IL (US); Terry Y. Nakagawa, Evanston, IL (US)

(73) Assignee: Abbott Laboratories, Abbott Park, IL (US)

( * ) Notice: Subject to any disclaimer, the term of this patent is extended or adjusted under 35 U.S.C. 154(b) by 615 days.

(21) Appl. No.: 11/788,949

(22) Filed: Apr. 23, 2007

(65) Prior Publication Data

US 2008/0176756 A1 Jul. 24, 2008

Related U.S. Application Data

(60) Provisional application No. 60/856,614, filed on Nov. 3, 2006, provisional application No. 60/794,370, filed on Apr. 24, 2006.

(51) Int. Cl.
*C07K 16/00* (2006.01)
*C12N 5/07* (2010.01)
*C07H 21/04* (2006.01)

(52) U.S. Cl. .................... 530/387.1; 435/326; 536/23.53

(58) Field of Classification Search ............... 530/387.1; 435/326; 536/23.53
See application file for complete search history.

(56) References Cited

U.S. PATENT DOCUMENTS 4,816,397 A 3/1989 Boss et al.
4,894,366 A 1/1990 Okuharra et al.
5,223,409 A * 6/1993 Ladner et al. ...................... 506/1
5,489,668 A 2/1996 Morrison et al.
5,532,137 A * 7/1996 Niwa et al. ................... 435/7.92
5,635,406 A * 6/1997 Grenier et al. ................ 436/536
5,990,150 A 11/1999 Matsui et al.
6,015,662 A 1/2000 Hackett, Jr. et al.
6,090,382 A 7/2000 Salfeld et al.
6,300,065 B1 10/2001 Kieke et al.
6,423,538 B1 7/2002 Wittrup et al.
6,696,251 B1 2/2004 Wittrup et al.
6,699,658 B1 3/2004 Wittrup et al.
6,759,243 B2 7/2004 Kranz et al.
6,777,540 B1 * 8/2004 Okumura et al. .......... 530/387.9
7,078,495 B1 * 7/2006 Kasper et al. .............. 530/389.8
7,186,518 B2 * 3/2007 Wang et al. .................. 435/7.92
7,575,875 B2 * 8/2009 Konrath et al. ................ 435/7.1
7,592,186 B2 * 9/2009 Drengler et al. .............. 436/507
7,625,726 B2 * 12/2009 Gu et al. ....................... 435/118
7,718,380 B2 * 5/2010 Konrath et al. ................ 435/7.1
2002/0137127 A1 * 9/2002 Moore et al. ................. 435/69.1
2004/0102429 A1 5/2004 Modak et al.
2005/0112778 A1 * 5/2005 Wang et al. ................... 436/501
2005/0176080 A1 * 8/2005 Bodepudi et al. ............ 435/7.92
2005/0227289 A1 10/2005 Reilly et al.
2008/0020401 A1 1/2008 Grenier et al.

FOREIGN PATENT DOCUMENTS

EP 0 293 892 12/1988
WO 0109190 2/2001
WO WO 01/09190 * 2/2001

OTHER PUBLICATIONS

Tietz, Norbert W. Clinical Guide to Laboratory Tests. Philadelphia, P.A., W. B. Saunders Company, 1983. pp. 346, 376, 398, 446, 516, and 695.
International Search Report (Jul. 11, 2008), see note in Office action.
Ausubel, et al. Current Protocols in Molecular Biology, vol. Supplemental 24 (1993), pp. 6.3.1-6.3.6.
Bird, et al. Science, vol. 242 (Oct. 21, 1988), pp. 423-426.
Boder, et al. Nature Biotechnology, vol. 15 (Jun. 15, 1997), pp. 553-557.
Boder, et al. Biotechnology Prog, vol. 14 (1998), pp. 55-62.
Boder, et al. Methods in Enzymology, vol. 328 (2000), pp. 430-444.
Boder, et al. PNAS, vol. 97, No. 20 (2000), pp. 10701-10705.
Boss, et al. Immunology Today, vol. 6, No. 1 (1985), pp. 12-13.
Darling, et al. Assay and Drug Development Technologies, vol. 2, No. 6 (2004), pp. 647-657.
Feldhaus Nature Biotechnology, vol. 21 (Feb. 2003), pp. 163-170.
Feldhaus and Siegel Journal of Immunology Methods, vol. 290, No. 1-2 (2004), pp. 69-80.
Feldhaus, et al. Methods in Molecular Biology 2nd Edition (Totowa, NJ, Humana Press Inc., 2004), pp. 311-332.
Huston, et al. Proc. Natl. Academy of Science USA, vol. 85 (Aug. 1988), pp. 5879-5883.
IMx Tacrolimus II Package Insert, Abbott Diagnostics Division (Sep. 2007).
Inamura, et al. Transplantation, vol. 45, No. 1 (Jan. 1988), pp. 206-209.
Kahan, et al. Clinical Chemistry, vol. 36, No. 8 (1990), pp. 1510-1516. Kaufman, et al. Journal of Molecular Biology, vol. 159 (1982), pp. 601-621.
McCafferty, et al. Nature, vol. 384 (Dec. 6, 1990), pp. 552-554.
Mizushima and Nagata Nucleic Acids Research, vol. 18 (1990), pp. 5322.
Murthy, et al. Clinical Biochemistry, vol. 31, No. 8 (Nov. 1998), pp. 613-617.
Paul, et al. Fundamental Immunology 2nd Edition (New York, Raven Press 1989), pp. 332-336.
Schiestl, et al. Current Genetics, vol. 16 (1989), pp. 339-346.
Urlaub, et al. Proc. Natl. Academy of Science USA, vol. 77, No. 7 (Jul. 1980), pp. 4219-4220.
Urlaub, et al. Cell, vol. 33 (Jun. 1983), pp. 405-412.
Warty, et al. Therapeutic Drug Monitoring, vol. 15 (1993), pp. 204-208.

(Continued)

*Primary Examiner* — Amber D. Steele
(74) *Attorney, Agent, or Firm* — Audrey L. Bartnicki; Carol Larcher; Larcher & Chao Law Group

(57) ABSTRACT

The present invention relates among other things to antibodies that immunospecifically bind to at least one agent of interest (e.g., an immunosuppressive agent), methods for producing such antibodies, and immunoassays that employ said antibodies. Additionally, the present invention also relates to methods for selecting an antibody for use in a diagnostic immunoassay and methods for selecting an antigen for use in a diagnostic immunoassay. The present invention further relates to the improvement of antibody recognition of an active parent drug in the presence of one or more of its major metabolites.

7 Claims, 18 Drawing Sheets

OTHER PUBLICATIONS

Winkler, et al. Transplantation Proceedings, vol. 27, No. 1 (Feb. 1995), pp. 822-825.

U.S.P.T.O. Office Action dated Aug. 21, 2009, cover sheet and pp. 1-10, Notice of References, Information Disclosure Statement by Applicant and Considered by Examiner in U.S. Appl. No. 11/490,624.

ISA/US, International Search Report for International Application No. PCT/US07/88056, dated Aug. 25, 2008.

Melnikova et al., "Antigen-binding activity of monoclonal antibodies after incubation with organic solvents.", Biochemistery (Moscow), vol. 65, No. 11, 2000 pp. 1256-1265.

Tamura et al., "A highly sensitive Method to Assay FK506 Levels in Plasma", Transplantation Proceedings, 19, 5, 1987, pp. 23-29.

ISA/EP Extended European Search Report for Application No. EP07861291 dated Jan. 11, 2010, 11 pages, Abbott's Reference 8166EPO1.

* cited by examiner

```
GluValGlu LeuValGlu SerGlyGly AspLeuVal LysProGly GlySerLeu LysLeuSer CysAlaAla SerGlyPhe ThrPheSer
GAGGTGGAA TTGGTGGAG TCTGGGGGA GACTTAGTG AAGCCTGGA GGGTCCCTG AAACTCTCC TGTGCAGCC TCTGGATTC ACTTTCAGT
CTCCACCTT AACCACCTC AGACCCCCT CTGAATCAC TTCGGACCT CCCAGGGAC TTTGAGAGG ACACGTCGG AGACCTAAG TGAAAGTCA
SerTyrGly MetSerTrp ValArgGln ThrProAsp LysArgLeu GluTrpVal AlaThrIle SerSerGly GlyThrTyr ThrPheTyr
AGTTATGGC ATGTCTTGG GTTCGCCAG ACGCCAGAC AAGAGGCTG GAGTGGGTC GCAACCATT AGTAGTGGT GGTACTTAC ACCTTCTAT
TCAATACCG TACAGAACC CAAGCGGTC TGCGGTCTG TTCTCCGAC CTCACCCAG CGTTGGTAA TCATCACCA CCATGAATG TGGAAGATA
ProAspSer ValLysGly ArgPheThr IleSerArg AspAsnAla LysAsnThr LeuSerLeu GlnMetSer SerLeuLys SerAlaAsp
CCAGACAGT GTGAAGGGG CGCTTCACC ATCTCCAGA GACAATGCC AAGAACACC CTGTCCCTG CAAATGAGC AGTCTGAAG TCTGCAGAC
GGTCTGTCA CACTTCCCC GCGAAGTGG TAGAGGTCT CTGTTACGG TTCTTGTGG GACAGGGAC GTTTACTCG TCAGACTTC AGACGTCTG
ThrAlaMet TyrTyrCys SerArgGln ThrAspGly TyrSerTrp PheProTyr TrpGlyGln GlyThrLeu ValThrVal SerAla
ACAGCCATG TATTACTGT TCAAGACAG ACCGATGGT TACTCCTGG TTTCCTTAT TGGGGCCAA GGGACTCTG GTCACTGTC TCTGCA
TGTCGGTAC ATAATGACA AGTTCTGTC TGGCTACCA ATGAGGACC AAAGGAATA ACCCCGGTT CCCTGAGAC CAGTGACAG AGACGT
```

2B.

```
AspValLeu MetThrGln ThrProLeu SerLeuPro ValSerLeu GlyAspGln AlaSerIle SerCysLys SerSerGln SerIleVal
GATGTTTTG ATGACCCAA ACTCCACTC TCCCTGCCT GTCAGTCTT GGAGATCAA GCCTCCATC TCTTGCAAA TCTAGTCAG AGCATTGTA
CTACAAAAC TACTGGGTT TGAGGTGAG AGGGACGGA CAGTCAGAA CCTCTAGTT CGGAGGTAG AGAACGTTT AGATCAGTC TCGTAACAT
HisSerThr GlyAsnThr PheLeuGlu TrpPheLeu GlnLysPro GlyGlnSer ProLysLeu LeuIleTyr LysIleSer AsnArgPhe
CATAGTACT GGAAACACC TTTTTAGAA TGGTTTTTG CAGAAGCCA GGCCAGTCT CCAAAGCTC CTGATCTAC AAAATTTCC AACCGATTT
GTATCATGA CCTTTGTGG AAAAATCTT ACCAAAAAC GTCTTCGGT CCGGTCAGA GGTTTCGAG GACTAGATG TTTTAAAGG TTGGCTAAA
SerGlyVal ProAspArg PheSerGly SerGlySer GlyThrAsp PheThrLeu LysIleSer ArgValGlu SerGluAsp LeuGlyVal
TCTGGGGTC CCAGACAGG TTCAGTGGC AGTGGATCA GGGACAGAT TTCACACTC AAGATCAGC AGAGTGGAG TCTGAGGAT CTGGGAGTT
AGACCCCAG GGTCTGTCC AAGTCACCG TCACCTAGT CCCTGTCTA AAGTGTGAG TTCTAGTCG TCTCACCTC AGACTCCTA GACCCTCAA
TyrTyrCys PheGlnGly SerHisVal ProLeuThr PheGlyAla GlyThrLys LeuGluLeu LysArgAla
TATTACTGC TTTCAAGGT TCACATGTT CCGCTCACG TTCGGTGCT GGGACCAAG CTGGAGCTG AAACGGGCG
ATAATGACG AAAGTTCCA AGTGTACAA GGCGAGTGC AAGCCACGA CCCTGGTTC GACCTCGAC TTTGCCCGC
```

| | H1 | | H2 | | H3 |
|---|---|---|---|---|---|
| | GFTFSSYGMS (SEQ ID NO:2) | | TISSGGTYTF (SEQ ID NO: 4) | | QTDGYSWFPY (SEQ ID NO: 6) |
| H1-1 | GFT | H2-1 | TIS | H3-1 | QTD |
| H1-2 | FTF | H2-2 | ISS | H3-2 | TDG |
| H1-3 | TFS | H2-3 | SSG | H3-3 | DGY |
| H1-4 | FSS | H2-4 | SGG | H3-4 | GYS |
| H1-5 | SSY | H2-5 | GGT | H3-5 | YSW |
| H1-6 | SYG | H2-6 | GTY | H3-6 | SWF |
| H1-7 | YGM | H2-7 | TYT | H3-7 | WFP |
| H1-8 | GMS | H2-8 | YTF | H3-8 | FPY |

| | | | | | |
|---|---|---|---|---|---|
| | KISSQSIVHSTGNTFLE(SEQ ID NO:93) | | KISNRFS(SEQ ID NO:11) | | FQGSHVPLT(SEQ ID NO:13) |
| L1-1 | KIS | L2-1 | KIS | L3-1 | FQG |
| L1-2 | ISS | L2-2 | ISN | L3-2 | QGS |
| L1-2 | SSQ | L2-3 | SNR | L3-3 | GSH |
| L1-3 | SQS | L2-4 | NRF | L3-4 | SHV |
| L1-4 | QSI | L2-5 | RFS | L3-5 | HVP |
| L1-5 | SIV | | | L3-6 | VPL |
| L1-6 | IVH | | | L3-7 | PLT |
| L1-7 | VHS | | | | |
| L1-8 | HST | | | | |
| L1-9 | STG | | | | |
| L1-10 | TGN | | | | |
| L1-11 | GNT | | | | |
| L1-12 | NTF | | | | |
| L1-13 | TFL | | | | |
| L1-14 | FLE | | | | |

Fig. 6

| Clone | FR1 | CDR-H1 | FR2 | CDR-H2 |
|---|---|---|---|---|
| 1-60-46 WT | EVELVESGGDLVKPGGSLKLSCAAS **(SEQ ID NO:1)** | GFTFSSYGMS **(SEQ ID NO:2)** | WVRQTPDKRLEWVA **(SEQ ID NO:3)** | TISSGGTYTF **(SEQ ID NO:4)** |
| H2-1 | EVELVESGGDLVKPGGSLKLSCAAS **(SEQ ID NO:1)** | GFTFSSYGMS **(SEQ ID NO:2)** | WVRQTPDKRLEWVA **(SEQ ID NO:3)** | TISSGGT**W**TF **(SEQ ID NO:15)** |
| H2-1A | EVELVESGGDLVKPGGSLKLSCAAS **(SEQ ID NO:1)** | GFTFSSYGMS **(SEQ ID NO:2)** | WVRQTPDKRLEWVA **(SEQ ID NO:3)** | TISSGG**AW**TF **(SEQ ID NO:16)** |
| H2-1B | EVELVESGGDLVKPGGSLKLSCAAS **(SEQ ID NO:1)** | GFTFSSYGMS **(SEQ ID NO:2)** | WVRQTPDKRLEWVA **(SEQ ID NO:3)** | TISSGG**KWV**F **(SEQ ID NO:17)** |
| H2-3B | EVELVESGGDLVKPGGSLKLSCAAS **(SEQ ID NO:1)** | GFTFSSYGMS **(SEQ ID NO:2)** | WVRQTPDKRLEWVA **(SEQ ID NO:3)** | TISSGG**EW**TF **(SEQ ID NO:18)** |

| Clone | FR3 | CDR-H3 | FR4 |
|---|---|---|---|
| 1-60-46 WT | YPDSVKGRFTISRDNAKNTLSLQMSSLKSADTAMYYCSR **(SEQ ID NO:5)** | QTDGYSWFPY **(SEQ ID NO:6)** | WGQGTLVTVSA **(SEQ ID NO:7)** |
| H2-1 | YPDSVKGRFTISRDNAKNTLSLQMSSLKSADTAMYYCSR **(SEQ ID NO:5)** | QTDGYSWFPY **(SEQ ID NO:6)** | WGQGTLVTVSA **(SEQ ID NO:7)** |
| H2-1A | YPDSVKGRFTISRDNAKNTLSLQMSSLKSADTAMYYCSR **(SEQ ID NO:5)** | QTDGYSWFPY **(SEQ ID NO:6)** | WGQGTLVTVSA **(SEQ ID NO:7)** |
| H2-1B | YPDSVKGRFTISRDNAKNTLSLQMSSLKSADTAMYYCSR **(SEQ ID NO:5)** | QTDGYSWFPY **(SEQ ID NO:6)** | WGQGTLVTVSA **(SEQ ID NO:7)** |
| H2-3B | YPDSVKGRFTISRDNAKNTLSLQMSSLKSADTAMYYCSR **(SEQ ID NO:5)** | QTDGYSWFPY **(SEQ ID NO:6)** | WGQGTLVTVSA **(SEQ ID NO:7)** |
| H2-1 | YPDSVKGRFTISRDNAKNTLSLQMSSLKSADTAMYYCSR **(SEQ ID NO:5)** | QTDGYSWFPY **(SEQ ID NO:6)** | WGQGTLVTVSA **(SEQ ID NO:7)** |

Fig. 7A

| Clone | FR1 | CDR-L1 | FR2 | CDR-L2 |
|---|---|---|---|---|
| 1-60-46 WT | DVLMTQTPLSLPVSLGDQASISC **(SEQ ID NO:8)** | KSSQSIVHSTGNTFLE **(SEQ ID NO:9)** | WFLQKPGQSPKLLIY **(SEQ ID NO:10)** | KISNRFS **(SEQ ID NO:11)** |
| L1-1 | DVLMTQTPLSLPVSLGDQASISC **(SEQ ID NO:8)** | KSSQ**G**IVHSTGNTFLE **(SEQ ID NO:19)** | WFLQKPGQSPKLLIY **(SEQ ID NO:10)** | KISNRFS **(SEQ ID NO:11)** |
| L1-2A | DVLMTQTPLSLPVSLGDQASISC **(SEQ ID NO:8)** | KSS**AG**IVHSTGNTFLE **(SEQ ID NO:20)** | WFLQKPGQSPKLLIY **(SEQ ID NO:10)** | KISNRFS **(SEQ ID NO:11)** |
| L1-4B | DVLMTQTPLSLPVSLGDQASISC **(SEQ ID NO:8)** | KSS**GGL**VHSTGNTFLE **(SEQ ID NO:21)** | WFLQKPGQSPKLLIY **(SEQ ID NO:10)** | KISNRFS **(SEQ ID NO:11)** |
| L1-1B | DVLMTQTPLSLPVSLGDQASISC **(SEQ ID NO:8)** | KSSQ**GL**VHSTGNTFLE **(SEQ ID NO:22)** | WFLQKPGQSPKLLIY **(SEQ ID NO:10)** | KISNRFS **(SEQ ID NO:11)** |
| L3-A | DVLMTQTPLSLPVSLGDQASISC **(SEQ ID NO:8)** | KSSQSIVHSTGNTFLE **(SEQ ID NO:9)** | WFLQKPGQSPKLLIY **(SEQ ID NO:10)** | KISNRFS **(SEQ ID NO:11)** |
| L3-B | DVLMTQTPLSLPVSLGDQASISC **(SEQ ID NO:8)** | KSSQSIVHSTGNTFLE **(SEQ ID NO:9)** | WFLQKPGQSPKLLIY **(SEQ ID NO:10)** | KISNRFS **(SEQ ID NO:11)** |
| L3-C | DVLMTQTPLSLPVSLGDQASISC **(SEQ ID NO:8)** | KSSQSIVHSTGNTFLE **(SEQ ID NO:9)** | WFLQKPGQSPKLLIY **(SEQ ID NO:10)** | KISNRFS **(SEQ ID NO:11)** |
| L3-D | DVLMTQTPLSLPVSLGDQASISC **(SEQ ID NO:8)** | KSSQSIVHSTGNTFLE **(SEQ ID NO:9)** | WFLQKPGQSPKLLIY **(SEQ ID NO:10)** | KISNRFS **(SEQ ID NO:11)** |
| L3-1B | DVLMTQTPLSLPVSLGDQASISC **(SEQ ID NO:8)** | KSSQSIVHSTGNTFLE **(SEQ ID NO:9)** | WFLQKPGQSPKLLIY **(SEQ ID NO:10)** | KISNRFS **(SEQ ID NO:11)** |
| L3-1A | DVLMTQTPLSLPVSLGDQASISC **(SEQ ID NO:8)** | KSSQSIVHSTGNTFLE **(SEQ ID NO:9)** | WFLQKPGQSPKLLIY **(SEQ ID NO:10)** | KISNRFS **(SEQ ID NO:11)** |
| L3-2A | DVLMTQTPLSLPVSLGDQASISC **(SEQ ID NO:8)** | KSSQSIVHSTGNTFLE **(SEQ ID NO:9)** | WFLQKPGQSPKLLIY **(SEQ ID NO:10)** | KISNRFS **(SEQ ID NO:11)** |
| L3-3A | DVLMTQTPLSLPVSLGDQASISC **(SEQ ID NO:8)** | KSSQSIVHSTGNTFLE **(SEQ ID NO:9)** | WFLQKPGQSPKLLIY **(SEQ ID NO:10)** | KISNRFS **(SEQ ID NO:11)** |
| L3-4A | DVLMTQTPLSLPVSLGDQASISC **(SEQ ID NO:8)** | KSSQSIVHSTGNTFLE **(SEQ ID NO:9)** | WFLQKPGQSPKLLIY **(SEQ ID NO:10)** | KISNRFS **(SEQ ID NO:11)** |
| L3-2B | DVLMTQTPLSLPVSLGDQASISC **(SEQ ID NO:8)** | KSSQSIVHSTGNTFLE **(SEQ ID NO:9)** | WFLQKPGQSPKLLIY **(SEQ ID NO:10)** | KISNRFS **(SEQ ID NO:11)** |

Fig. 7B

| Clone | FR3 | CDR-L3 | FR4 |
|---|---|---|---|
| 1-60-46 WT | GVPDRFSGSGSGTDFTLKISRVESEDLGVYYC (SEQ ID NO:12) | FQGSHVPLT (SEQ ID NO:13) | FGAGTKLELKRA (SEQ ID NO:14) |
| L1-1 | GVPDRFSGSGSGTDFTLKISRVESEDLGVYYC (SEQ ID NO:12) | FQGSHVPLT (SEQ ID NO:13) | FGAGTKLELKRA (SEQ ID NO:14) |
| L1-2A | GVPDRFSGSGSGTDFTLKISRVESEDLGVYYC (SEQ ID NO:12) | FQGSHVPLT (SEQ ID NO:13) | FGAGTKLELKRA (SEQ ID NO:14) |
| L1-4B | GVPDRFSGSGSGTDFTLKISRVESEDLGVYYC (SEQ ID NO:12) | FQGSHVPLT (SEQ ID NO:13) | FGAGTKLELKRA (SEQ ID NO:14) |
| L1-1B | GVPDRFSGSGSGTDFTLKISRVESEDLGVYYC (SEQ ID NO:12) | FQGSHVPLT (SEQ ID NO:13) | FGAGTKLELKRA (SEQ ID NO:14) |
| L3-A | GVPDRFSGSGSGTDFTLKISRVESEDLGVYYC (SEQ ID NO:12) | FQGSH**A**PLT (SEQ ID NO:23) | FGAGTKLELKRA (SEQ ID NO:14) |
| L3-B | GVPDRFSGSGSGTDFTLKISRVESEDLGVYYC (SEQ ID NO:12) | FQGS**RA**PLT (SEQ ID NO:24) | FGAGTKLELKRA (SEQ ID NO:14) |
| L3-C | GVPDRFSGSGSGTDFTLKISRVESEDLGVYYC (SEQ ID NO:12) | FQGSH**D**PLT (SEQ ID NO:25) | FGAGTKLELKRA (SEQ ID NO:14) |
| L3-D | GVPDRFSGSGSGTDFTLKISRVESEDLGVYYC (SEQ ID NO:12) | FQGSH**C**PLT (SEQ ID NO:26) | FGAGTKLELKRA (SEQ ID NO:14) |
| L3-1B | GVPDRFSGSGSGTDFTLKISRVESEDLGVYYC (SEQ ID NO:12) | FQGSH**S**PLT (SEQ ID NO:27) | FGAGTKLELKRA (SEQ ID NO:14) |
| L3-1A | GVPDRFSGSGSGTDFTLKISRVESEDLGVYYC (SEQ ID NO:12) | FQG**GRC**PLT (SEQ ID NO:28) | FGAGTKLELKRA (SEQ ID NO:14) |
| L3-2A | GVPDRFSGSGSGTDFTLKISRVESEDLGVYYC (SEQ ID NO:12) | FQG**GVC**PLT (SEQ ID NO:29) | FGAGTKLELKRA (SEQ ID NO:14) |
| L3-3A | GVPDRFSGSGSGTDFTLKISRVESEDLGVYYC (SEQ ID NO:12) | FQGS**TC**PLT (SEQ ID NO:30) | FGAGTKLELKRA (SEQ ID NO:14) |
| L3-4A | GVPDRFSGSGSGTDFTLKISRVESEDLGVYYC (SEQ ID NO:12) | FQGS**KC**PLT (SEQ ID NO:31) | FGAGTKLELKRA (SEQ ID NO:14) |
| L3-2B | GVPDRFSGSGSGTDFTLKISRVESEDLGVYYC (SEQ ID NO:12) | FQGS**SS**PLT (SEQ ID NO:32) | FGAGTKLELKRA (SEQ ID NO:14) |

Fig. 8

| | koff (1/sec) | | koff improvement | | KD (M) | | KD improvement | |
|---|---|---|---|---|---|---|---|---|
| clone | no organic | 10% MeOH | no organic | 10% MeOH | no organic | 10% MeOH | no organic | 10% MeOH |
| WT | 1.30E-04 | 9.38E-04 | 1.0 | 1.0 | 4.18E-10 | 5.80E-10 | 1.0 | 1.0 |
| H2-1 | 5.2E-05 | 4.7E-04 | 2.5 | 2.0 | | | | |
| H2-1A | 2.9E-05 | 1.6E-04 | 4.5 | 5.9 | 5.3E-11 | 1.3E-10 | 7.9 | 4.5 |
| H2-1B | 3.4E-05 | 2.5E-04 | 3.8 | 3.8 | | | | |
| H2-3B | 3.7E-05 | 1.9E-04 | 3.5 | 4.9 | | | | |
| L1-2A | 2.6E-05 | 2.2E-04 | 5.0 | 4.3 | | | | |
| L1-4A | 3.3E-05 | 2.3E-04 | 3.9 | 4.1 | | | | |
| L1-1B | 2.8E-05 | 1.9E-04 | 4.6 | 4.9 | 1.4E-10 | 2.7E-10 | 3.0 | 2.1 |
| L3-A | 6.0E-05 | 4.7E-04 | 2.2 | 2.0 | | | | |
| L3-1A | 3.5E-05 | 1.2E-04 | 3.7 | 7.8 | 2.6E-10 | 4.0E-10 | 1.6 | 1.5 |
| L3-2A | 4.3E-05 | 1.5E-04 | 3.0 | 6.3 | | | | |
| L3-3A | 5.0E-05 | 1.7E-04 | 2.6 | 5.5 | | | | |
| L3-4A | 5.0E-05 | 1.9E-04 | 2.6 | 4.9 | | | | |
| L3-1B | 4.7E-05 | 3.5E-04 | 2.8 | 2.7 | | | | |
| L3-2B | 4.2E-05 | 3.0E-04 | 3.1 | 3.2 | 2.2E-10 | 3.6E-10 | 1.9 | 1.6 |
| H2-1A / L1-1B / L3-1A | 4.4E-05 | 1.3E-04 | 3.0 | 7.2 | | 4.1E-10 | | 1.4 |
| H2-1A / L1-1B / L3-2B | 3.9E-05 | 8.5E-05 | 3.3 | 11.1 | | 6.1E-11 | | 9.5 |
| H2-1A / L1-1B / L3-A | 2.40E-05 | 7.50E-05 | 5.4 | 12.5 | | 3.80E-11 | | 15.3 |
| H2-1B / L1-1B / L3 -1B | | 5.90E-05 | | 15.9 | | 5.30E-11 | | 10.9 |
| H2-3B / L1-1B /L3-1B | | 1.00E-04 | | 9.4 | | | | |
| H2-3B / L1-4A / L3-1B | | 1.50E-04 | | 6.3 | | | | |
| H2-1A / L1-1B / L3-1B | | 6.60E-05 | | 14.2 | | 4.90E-11 | | 11.8 |
| H2-1A / L3-1A | 4.6E-05 | 5.5E-05 | 2.8 | 17.1 | | 7.4E-11 | | 7.8 |
| H2-1A / L3-2B | 3.90E-05 | 1.20E-04 | 3.3 | 7.8 | | 6.30E-11 | | 9.2 |
| L1-1B / L3-1A | 4.40E-05 | 2.50E-04 | 3.0 | 3.8 | | 1.00E-09 | | 0.6 |
| L1-1B / L3-2B | 4.50E-05 | 2.30E-04 | 2.9 | 4.1 | | 1.60E-10 | | 3.6 |
| H2-3B / L3-2A | | 6.90E-05 | | 13.6 | | | | |

| | IGG | | | | | | |
|---|---|---|---|---|---|---|---|
| MUTATIONS | CDR-H1 | CDR-H2 | CDR-H3 | CDR-L1 | CDR-L2 | CDR-L3 | NOMEN-CLATURE |
| 1-60-46 WT | GFTFSSYGMS (SEQ ID NO:2) | TISSGGTYTF (SEQ ID NO:4) | QTDGYSWFPY (SEQ ID NO:6) | KSSQSIVHSTGNTFLE (SEQ ID NO:9) | KISNRFS (SEQ ID NO:11) | FQGSHVPLT (SEQ ID NO:13) | WT |
| H2-1A/L1-1B/L3-2B | GFTFSSYGMS (SEQ ID NO:2) | TISSGG**AW**TF (SEQ ID NO:16) | QTDGYSWFPY (SEQ ID NO:6) | KSSQ**GL**VHSTGNTFLE (SEQ ID NO:22) | KISNRFS (SEQ ID NO:11) | FQGS**SS**PLT (SEQ ID NO:32) | AM1 |
| H2-1A/L1-1B/L3-A | GFTFSSYGMS (SEQ ID NO:2) | TISSGG**AW**TF (SEQ ID NO:16) | QTDGYSWFPY (SEQ ID NO:6) | KSSQ**GL**VHSTGNTFLE (SEQ ID NO:22) | KISNRFS (SEQ ID NO:11) | FQGSH**A**PLT (SEQ ID NO:23) | AM2 |
| H2-1A/L3-2B | GFTFSSYGMS (SEQ ID NO:2) | TISSGG**AW**TF (SEQ ID NO:16) | QTDGYSWFPY (SEQ ID NO:6) | KSSQSIVHSTGNTFLE (SEQ ID NO:9) | KISNRFS (SEQ ID NO:11) | FQGS**SS**PLT (SEQ ID NO:32) | AM3 |
| H2-1A/L1-1B/L3-1A | GFTFSSYGMS (SEQ ID NO:2) | TISSGG**AW**TF (SEQ ID NO:16) | QTDGYSWFPY (SEQ ID NO:6) | KSSQ**GL**VHSTGNTFLE (SEQ ID NO:22) | KISNRFS (SEQ ID NO:11) | FQG**GRC**PLT (SEQ ID NO:28) | AM4 |
| H2-1B/L1-1B/L3-1B | GFTFSSYGMS (SEQ ID NO:2) | TISSGG**KWV**F (SEQ ID NO:17) | QTDGYSWFPY (SEQ ID NO:6) | KSSQ**GL**VHSTGNTFLE (SEQ ID NO:22) | KISNRFS (SEQ ID NO:11) | FQGSH**S**PLT (SEQ ID NO:27) | AM5 |

TACROLIMUS IMMUNOASSAY WITH METHANOL DILUENT

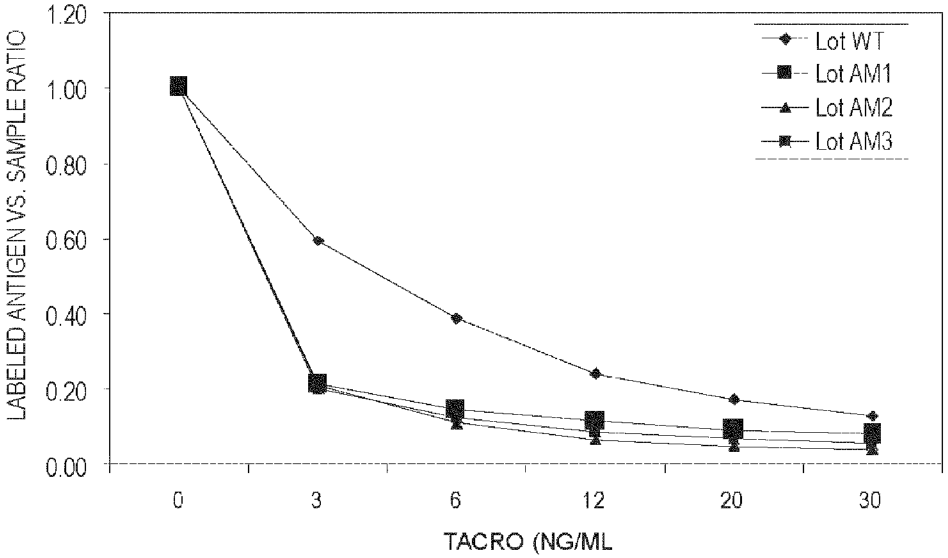

Fig. 11

```
GluValGlu LeuValGlu SerGlyGly AspLeuVal LysProGly GlySerLeu LysLeuSer CysAlaAla SerGlyPhe ThrPheSer
GAGGTGGAA TTGGTGGAG TCTGGGGGA GACTTAGTG AAGCCTGGA GGGTCCCTG AAACTCTCC TGTGCAGCC TCTGGATTC ACTTTCAGT
CTCCACCTT AACCACCTC AGACCCCCT CTGAATCAC TTCGGACCT CCCAGGGAC TTTGAGAGG ACACGTCGG AGACCTAAG TGAAAGTCA
SerTyrGly MetSerTrp ValArgGln ThrProAsp LysArgLeu GluTrpVal AlaThrIle SerSerGly GlyAlaTrp ThrPheTyr
AGTTATGGC ATGTCTTGG GTTCGCCAG ACGCCAGAC AAGAGGCTG GAGTGGGTC GCAACCATT AGTAGTGGT GGTGCCTGG ACGTTCTAT
TCAATACCG TACAGAACC CAAGCGGTC TGCGGTCTG TTCTCCGAC CTCACCCAG CGTTGGTAA TCATCACCA CCACGGACC TGCAAGATA
ProAspSer ValLysGly ArgPheThr IleSerArg AspAsnAla LysAsnThr LeuSerLeu GlnMetSer SerLeuLys SerAlaAsp
CCAGACAGT GTGAAGGGG CGCTTCACC ATCTCCAGA GACAATGCC AAGAACACC CTGTCCCTG CAAATGAGC AGTCTGAAG TCTGCAGAC
GGTCTGTCA CACTTCCCC GCGAAGTGG TAGAGGTCT CTGTTACGG TTCTTGTGG GACAGGGAC GTTTACTCG TCAGACTTC AGACGTCTG
ThrAlaMet TyrTyrCys SerArgGln ThrAspGly TyrSerTrp PheProTyr TrpGlyGln GlyThrLeu ValThrVal SerAlaSer
ACAGCCATG TATTACTGT TCAAGACAG ACCGATGGT TACTCCTGG TTTCCTTAT TGGGGCCAA GGGACTCTG GTCACTGTC TCTGCAAGC
TGTCGGTAC ATAATGACA AGTTCTGTC TGGCTACCA ATGAGGACC AAAGGAATA ACCCCGGTT CCCTGAGAC CAGTGACAG AGACGTTCG
AlaLysThr ThrAlaPro SerValTyr ProLeuAla ProValCys GlyAspThr ThrGlySer SerValThr LeuGlyCys LeuValLys
GCTAAAACA ACAGCCCCA TCGGTCTAT CCACTGGCC CCTGTGTGT GGAGATACA ACTGGCTCC TCGGTGACT CTAGGATGC CTGGTCAAG
CGATTTTGT TGTCGGGGT AGCCAGATA GGTGACCGG GGACACACA CCTCTATGT TGACCGAGG AGCCACTGA GATCCTACG GACCAGTTC
GlyTyrPhe ProGluPro ValThrLeu ThrTrpAsn SerGlySer LeuSerSer GlyValHis ThrPhePro AlaValLeu GlnSerAsp
GGTTATTTC CCTGAGCCA GTGACCTTG ACCTGGAAC TCTGGATCC CTGTCCAGT GGTGTGCAC ACCTTCCCA GCTGTCCTG CAGTCTGAC
CCAATAAAG GGACTCGGT CACTGGAAC TGGACCTTG AGACCTAGG GACAGGTCA CCACACGTG TGGAAGGGT CGACAGGAC GTCAGACTG
LeuTyrThr LeuSerSer SerValThr ValThrSer SerThrTrp ProSerGln SerIleThr CysAsnVal AlaHisPro AlaSerSer
CTCTACACC CTCAGCAGC TCAGTGACT GTAACCTCG AGCACCTGG CCCAGCCAG TCCATCACC TGCAATGTG GCCCACCCG GCAAGCAGC
GAGATGTGG GAGTCGTCG AGTCACTGA CATTGGAGC TCGTGGACC GGGTCGGTC AGGTAGTGG ACGTTACAC CGGGTGGGC CGTTCGTCG
ThrLysVal AspLysLys IleGluPro ArgGlyPro ThrIleLys ProCysPro ProCysLys CysProAla ProAsnLeu LeuGlyGly
ACCAAGGTG GACAAGAAA ATTGAGCCC AGAGGGCCC ACAATCAAG CCCTGTCCT CCATGCAAA TGCCCAGCA CCTAACCTC TTGGGTGGA
TGGTTCCAC CTGTTCTTT TAACTCGGG TCTCCCGGG TGTTAGTTC GGGACAGGA GGTACGTTT ACGGGTCGT GGATTGGAG AACCCACCT
ProSerVal PheIlePhe ProProLys IleLysAsp ValLeuMet IleSerLeu SerProIle ValThrCys ValValVal AspValSer
CCATCCGTC TTCATCTTC CCTCCAAAG ATCAAGGAT GTACTCATG ATCTCCCTG AGCCCCATA GTCACATGT GTGGTGGTG GATGTGAGC
GGTAGGCAG AAGTAGAAG GGAGGTTTC TAGTTCCTA CATGAGTAC TAGAGGGAC TCGGGGTAT CAGTGTACA CACCACCAC CTACACTCG
GluAspAsp ProAspVal GlnIleSer TrpPheVal AsnAsnVal GluValHis ThrAlaGln ThrGlnThr HisArgGlu AspTyrAsn
GAGGATGAC CCAGATGTC CAGATCAGC TGGTTTGTG AACAACGTG GAAGTACAC ACAGCTCAG ACACAAACC CATAGAGAG GATTACAAC
CTCCTACTG GGTCTACAG GTCTAGTCG ACCAAACAC TTGTTGCAC CTTCATGTG TGTCGAGTC TGTGTTTGG GTATCTCTC CTAATGTTG
SerThrLeu ArgValVal SerAlaLeu ProIleGln HisGlnAsp TrpMetSer GlyLysGlu PheLysCys LysValAsn AsnLysAsp
AGTACTCTC CGGGTGGTC AGTGCCCTC CCCATCCAG CACCAGGAC TGGATGAGT GGCAAGGAG TTCAAATGC AAGGTCAAC AACAAAGAC
TCATGAGAG GCCCACCAG TCACGGGAG GGGTAGGTC GTGGTCCTG ACCTACTCA CCGTTCCTC AAGTTTACG TTCCAGTTG TTGTTTCTG
LeuProAla ProIleGlu ArgThrIle SerLysPro LysGlySer ValArgAla ProGlnVal TyrValLeu ProProPro GluGluGlu
CTCCCAGCG CCCATCGAG AGAACCATC TCAAAACCC AAAGGGTCA GTAAGAGCT CCACAGGTA TATGTCTTG CCTCCACCA GAAGAAGAG
GAGGGTCGC GGGTAGCTC TCTTGGTAG AGTTTTGGG TTTCCCAGT CATTCTCGA GGTGTCCAT ATACAGAAC GGAGGTGGT CTTCTTCTC
MetThrLys LysGlnVal ThrLeuThr CysMetVal ThrAspPhe MetProGlu AspIleTyr ValGluTrp ThrAsnAsn GlyLysThr
ATGACTAAG AAACAGGTC ACTCTGACC TGCATGGTC ACAGACTTC ATGCCTGAA GACATTTAC GTGGAGTGG ACCAACAAC GGGAAAACA
TACTGATTC TTTGTCCAG TGAGACTGG ACGTACCAG TGTCTGAAG TACGGACTT CTGTAAATG CACCTCACC TGGTTGTTG CCCTTTTGT
GluLeuAsn TyrLysAsn ThrGluPro ValLeuAsp SerAspGly SerTyrPhe MetTyrSer LysLeuArg ValGluLys LysAsnTrp
GAGCTAAAC TACAAGAAC ACTGAACCA GTCCTGGAC TCTGATGGT TCTTACTTC ATGTACAGC AAGCTGAGA GTGGAAAAG AAGAACTGG
CTCGATTTG ATGTTCTTG TGACTTGGT CAGGACCTG AGACTACCA AGAATGAAG TACATGTCG TTCGACTCT CACCTTTTC TTCTTGACC
ValGluArg AsnSerTyr SerCysSer ValValHis GluGlyLeu HisAsnHis HisThrThr LysSerPhe SerArgThr ProGlyLys
GTGGAAAGA AATAGCTAC TCCTGTTCA GTGGTCCAC GAGGGTCTG CACAATCAC CACACGACT AAGAGCTTC TCCCGGACT CCGGGTAAA
CACCTTTCT TTATCGATG AGGACAAGT CACCAGGTG CTCCCAGAC GTGTTAGTG GTGTGCTGA TTCTCGAAG AGGGCCTGA GGCCCATTT
```

Fig. 12

```
AspValLeu MetThrGln ThrProLeu SerLeuPro ValSerLeu GlyAspGln AlaSerIle SerCysLys SerSerGln GlyLeuVal
GATGTTTTG ATGACCCAA ACTCCACTC TCCCTGCCT GTCAGTCTT GGAGATCAA GCCTCCATC TCTTGCAAA TCTAGTCAG GGGTTGGTC
CTACAAAAC TACTGGGTT TGAGGTGAG AGGGACGGA CAGTCAGAA CCTCTAGTT CGGAGGTAG AGAACGTTT AGATCAGTC CCCAACCAG
HisSerThr GlyAsnThr PheLeuGlu TrpPheLeu GlnLysPro GlyGlnSer ProLysLeu LeuIleTyr LysIleSer AsnArgPhe
CATAGTACT GGAAACACC TTTTTAGAA TGGTTTTTG CAGAAGCCA GGCCAGTCT CCAAAGCTC CTGATCTAC AAAATTTCC AACCGATTT
GTATCATGA CCTTTGTGG AAAAATCTT ACCAAAAAC GTCTTCGGT CCGGTCAGA GGTTTCGAG GACTAGATG TTTTAAAGG TTGGCTAAA
SerGlyVal ProAspArg PheSerGly SerGlySer GlyThrAsp PheThrLeu LysIleSer ArgValGlu SerGluAsp LeuGlyVal
TCTGGGGTC CCAGACAGG TTCAGTGGC AGTGGATCA GGGACAGAT TTCACACTC AAGATCAGC AGAGTGGAG TCTGAGGAT CTGGGAGTT
AGACCCCAG GGTCTGTCC AAGTCACCG TCACCTAGT CCCTGTCTA AAGTGTGAG TTCTAGTCG TCTCACCTC AGACTCCTA GACCCTCAA
TyrTyrCys PheGlnGly SerHisAla ProLeuThr PheGlyAla GlyThrLys LeuGluLeu LysArgAla SerAlaAsp AlaAlaPro
TATTACTGC TTTCAAGGT TCACATGCT CCGCTCACG TTCGGTGCT GGGACCAAG CTGGAGCTG AAACGGGCG AGCGCTGAT GCTGCACCA
ATAATGACG AAAGTTCCA AGTGTACGA GGCGAGTGC AAGCCACGA CCCTGGTTC GACCTCGAC TTTGCCCGC TCGCGACTA CGACGTGGT
ThrValSer IlePhePro ProSerSer GluGlnLeu ThrSerGly GlyAlaSer ValValCys PheLeuAsn AsnPheTyr ProLysAsp
ACTGTATCC ATCTTCCCA CCATCCAGT GAGCAGTTA ACATCTGGA GGTGCCTCA GTCGTGTGC TTCTTGAAC AACTTCTAC CCCAAAGAC
TGACATAGG TAGAAGGGT GGTAGGTCA CTCGTCAAT TGTAGACCT CCACGGAGT CAGCACACG AAGAACTTG TTGAAGATG GGGTTTCTG
IleAsnVal LysTrpLys IleAspGly SerGluArg GlnAsnGly ValLeuAsn SerTrpThr AspGlnAsp SerLysAsp SerThrTyr
ATCAATGTC AAGTGGAAG ATTGATGGC AGTGAACGA CAAAATGGC GTCCTGAAC AGTTGGACT GATCAGGAC AGCAAAGAC AGCACCTAC
TAGTTACAG TTCACCTTC TAACTACCG TCACTTGCT GTTTTACCG CAGGACTTG TCAACCTGA CTAGTCCTG TCGTTTCTG TCGTGGATG
SerMetSer SerThrLeu ThrLeuThr LysAspGlu TyrGluArg HisAsnSer TyrThrCys GluAlaThr HisLysThr SerThrSer
AGCATGAGC AGCACCCTC ACGTTGACC AAGGACGAG TATGAACGA CATAACAGC TATACCTGT GAGGCCACT CACAAGACA TCAACTTCA
TCGTACTCG TCGTGGGAG TGCAACTGG TTCCTGCTC ATACTTGCT GTATTGTCG ATATGGACA CTCCGGTGA GTGTTCTGT AGTTGAAGT
ProIleVal LysSerPhe AsnArgAsn GluCys
CCCATTGTC AAGAGCTTC AACAGGAAT GAGTGT
GGGTAACAG TTCTCGAAG TTGTCCTTA CTCACA
```

```
GluValGln LeuGlnGln SerGlyPro AspLeuVal LysProGly AlaSerMet LysIleSer CysLysAla SerGlyTyr SerPheThr
GAGGTCCAG CTGCAACAG TCTGGACCT GACCTGGTG AAGCCTGGA GCTTCAATG AAGATTTCC TGCAAGGCT TCTGGTTAC TCATTCACT
CTCCAGGTC GACGTTGTC AGACCTGGA CTGGACCAC TTCGGACCT CGAAGTTAC TTCTAAAGG ACGTTCCGA AGACCAATG AGTAAGTGA
SerTyrThr LeuAsnTrp ValArgGln SerProGly LysAsnLeu GluTrpIle GlyLeuIle TyrProTyr AsnGlyGly ThrAsnTyr
AGCTACACC CTGAACTGG GTGAGGCAG AGCCCTGGA AAGAACCTT GAGTGGATT GGACTTATT TATCCTTAC AATGGTGGT ACTAATTAC
TCGATGTGG GACTTGACC CACTCCGTC TCGGGACCT TTCTTGGAA CTCACCTAA CCTGAATAA ATAGGAATG TTACCACCA TGATTAATG
AsnGlnLys PheAsnAsp LysAlaThr PheThrVal AspLysSer SerSerThr AlaTyrMet GluLeuLeu SerLeuThr SerGluAsp
AACCAGAAA TTCAACGAC AAGGCCACA TTTACTGTG GACAAGTCA TCCAGCACA GCCTACATG GAGCTCCTC AGTCTGACG TCTGAGGAC
TTGGTCTTT AAGTTGCTG TTCCGGTGT AAATGACAC CTGTTCAGT AGGTCGTGT CGGATGTAC CTCGAGGAG TCAGACTGC AGACTCCTG
SerAlaVal TyrTyrCys AlaArgVal GlyTyrTyr GlyThrThr ProTyrTyr AlaMetAsp TyrTrpGly GlnGlyThr SerValThr
TCTGCAGTC TATTACTGT GCAAGGGTT GGTTACTAC GGAACTACT CCTTACTAT GCTATGGAC TACTGGGGT CAAGGAACC TCAGTCACC
AGACGTCAG ATAATGACA CGTTCCCAA CCAATGATG CCTTGATGA GGAATGATA CGATACCTG ATGACCCCA GTTCCTTGG AGTCAGTGG
ValSerSer
GTCTCCTCA
CAGAGGAGT
```

13B.

```
AspIleVal LeuThrGln SerProAla SerLeuAla ValSerLeu GlyGlnArg AlaThrIle SerCysArg AlaSerLys SerValAsp
GACATTGTA CTGACCCAA TCTCCAGCT TCTTTGGCT GTGTCTCTA GGGCAGAGG GCCACCATC TCCTGCAGA GCCAGCAAA AGTGTTGAT
CTGTAACAT GACTGGGTT AGAGGTCGA AGAAACCGA CACAGAGAT CCCGTCTCC CGGTGGTAG AGGACGTCT CGGTCGTTT TCACAACTA
TyrTyrGly IleSerPhe MetAsnTrp PheGlnGln LysProGly GlnProPro LysLeuLeu IleTyrAla AlaSerSer GlnGlySer
TATTATGGC ATTAGTTTT ATGAACTGG TTCCAACAG AAACCAGGA CAGCCACCC AAACTCCTC ATCTATGCT GCATCCAGC CAAGGATCC
ATAATACCG TAATCAAAA TACTTGACC AAGGTTGTC TTTGGTCCT GTCGGTGGG TTTGAGGAG TAGATACGA CGTAGGTCG GTTCCTAGG
GlyValPro AlaArgPhe SerGlySer GlySerGly ThrAspPhe SerLeuSer IleHisPro MetGluGlu AspAspThr AlaMetTyr
GGGGTCCCT GCCAGGTTT AGTGGCAGT GGGTCTGGG ACAGACTTC AGCCTCAGC ATCCATCCT ATGGAGGAG GATGATACT GCAATGTAT
CCCCAGGGA CGGTCCAAA TCACCGTCA CCCAGACCC TGTCTGAAG TCGGAGTCG TAGGTAGGA TACCTCCTC CTACTATGA CGTTACATA
PheCysGln HisSerLys GluValPro TrpThrPhe GlyGlyGly ThrAsnLeu GluIleLys ArgAla
TTCTGTCAG CACAGTAAG GAGGTTCCG TGGACGTTC GGTGGAGGC ACCAACCTG GAAATCAAA CGGGCG
AAGACAGTC GTGTCATTC CTCCAAGGC ACCTGCAAG CCACCTCCG TGGTTGGAC CTTTAGTTT GCCCGC
```

| Clone | DCR-H1 | CDR-H2 | CDR-H3 |
|---|---|---|---|
| **29-56-14 WT** | GYSFTSYTLN (SEQ ID NO: 94) | IYPYNGGTN (SEQ ID NO: 95) | VGYYGTTPYYAMDY (SEQ ID NO: 97) |
| **R2-9 Mutant** | GYSFTSYTLN (SEQ ID NO: 94) | I**HLP**NGGTN (SEQ ID NO: 96) | VGYYG**PSW**YYAMDY (SEQ ID NO:98) |

| Clone | CDR-L1 | CDR-L2 | CDR-L3 |
|---|---|---|---|
| **29-56-14 WT** | RASKSVDYYGISFMN (SEQ ID NO: 99) | AASSQGS (SEQ ID NO: 100) | QHSKEVPWT (SEQ ID NO: 102) |
| **R2-9 Mutant** | RASKSVDYYGISFMN (SEQ ID NO: 99) | AAS**KRA**S (SEQ ID NO: 101) | QHS**MQ**VPWT (SEQ ID NO: 103) |

FIG. 14

Fig. 16
CsA
M17
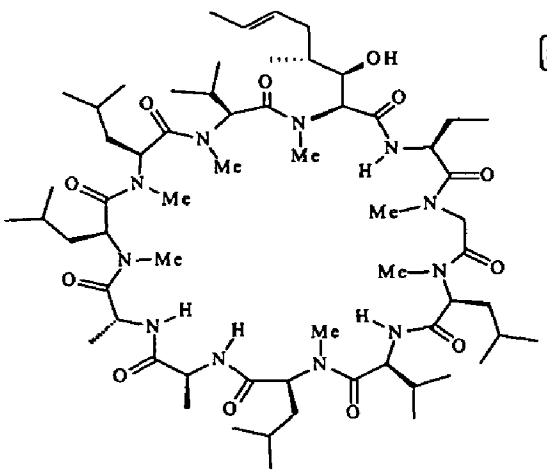
Cyclosporine A (1)
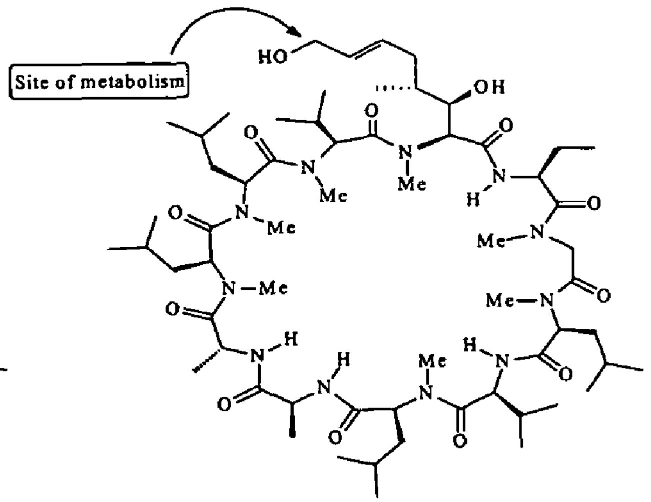
Cyclosporine A-metabolite (2, AM1 or M17)
Cyclosporine
(Cyclosporine A, Cyclosporin A, CsA)
Molecular Formula: $C_{62} H_{111} N_{11} O_{12}$
Molecular Weight: 1202.61
AM1/M17 Metabolite
Molecular Formula: $C_{62} H_{111} N_{11} O_{13}$
Molecular Weight: 1218.61

SEQUENCE LISTING

```
<160> NUMBER OF SEQ ID NOS: 103

<210> SEQ ID NO 1
<211> LENGTH: 25
<212> TYPE: PRT
<213> ORGANISM: Mouse

<400> SEQUENCE: 1

Glu Val Glu Leu Val Glu Ser Gly Gly Asp Leu Val Lys Pro Gly Gly
1               5                   10                  15

Ser Leu Lys Leu Ser Cys Ala Ala Ser
            20                  25


<210> SEQ ID NO 2
<211> LENGTH: 10
<212> TYPE: PRT
<213> ORGANISM: Mouse

<400> SEQUENCE: 2

Gly Phe Thr Phe Ser Ser Tyr Gly Met Ser
1               5                   10


<210> SEQ ID NO 3
<211> LENGTH: 14
<212> TYPE: PRT
<213> ORGANISM: Mouse

<400> SEQUENCE: 3

Trp Val Arg Gln Thr Pro Asp Lys Arg Leu Glu Trp Val Ala
1               5                   10


<210> SEQ ID NO 4
<211> LENGTH: 10
<212> TYPE: PRT
<213> ORGANISM: Mouse

<400> SEQUENCE: 4

Thr Ile Ser Ser Gly Gly Thr Tyr Thr Phe
1               5                   10


<210> SEQ ID NO 5
<211> LENGTH: 39
<212> TYPE: PRT
<213> ORGANISM: Mouse

<400> SEQUENCE: 5

Tyr Pro Asp Ser Val Lys Gly Arg Phe Thr Ile Ser Arg Asp Asn Ala
1               5                   10                  15

Lys Asn Thr Leu Ser Leu Gln Met Ser Ser Leu Lys Ser Ala Asp Thr
            20                  25                  30

Ala Met Tyr Tyr Cys Ser Arg
        35
```

<210> SEQ ID NO 6
<211> LENGTH: 10
<212> TYPE: PRT
<213> ORGANISM: Mouse

<400> SEQUENCE: 6

```
Gln Thr Asp Gly Tyr Ser Trp Phe Pro Tyr
1               5                   10
```

<210> SEQ ID NO 7
<211> LENGTH: 11
<212> TYPE: PRT
<213> ORGANISM: Mouse

<400> SEQUENCE: 7

```
Trp Gly Gln Gly Thr Leu Val Thr Val Ser Ala
1               5                   10
```

<210> SEQ ID NO 8
<211> LENGTH: 23
<212> TYPE: PRT
<213> ORGANISM: Mouse

<400> SEQUENCE: 8

```
Asp Val Leu Met Thr Gln Thr Pro Leu Ser Leu Pro Val Ser Leu Gly
1               5                   10                  15

Asp Gln Ala Ser Ile Ser Cys
            20
```

<210> SEQ ID NO 9
<211> LENGTH: 16
<212> TYPE: PRT
<213> ORGANISM: Mouse

<400> SEQUENCE: 9

```
Lys Ser Ser Gln Ser Ile Val His Ser Thr Gly Asn Thr Phe Leu Glu
1               5                   10                  15
```

<210> SEQ ID NO 10
<211> LENGTH: 15
<212> TYPE: PRT
<213> ORGANISM: Mouse

<400> SEQUENCE: 10

```
Trp Phe Leu Gln Lys Pro Gly Gln Ser Pro Lys Leu Leu Ile Tyr
1               5                   10                  15
```

<210> SEQ ID NO 11
<211> LENGTH: 7
<212> TYPE: PRT
<213> ORGANISM: Mouse

<400> SEQUENCE: 11

```
Lys Ile Ser Asn Arg Phe Ser
1               5
```

<210> SEQ ID NO 12
<211> LENGTH: 32
<212> TYPE: PRT
<213> ORGANISM: Mouse

<400> SEQUENCE: 12

```
Gly Val Pro Asp Arg Phe Ser Gly Ser Gly Ser Gly Thr Asp Phe Thr
1               5                   10                  15

Leu Lys Ile Ser Arg Val Glu Ser Glu Asp Leu Gly Val Tyr Tyr Cys
```

-continued 20 25 30

<210> SEQ ID NO 13
<211> LENGTH: 9
<212> TYPE: PRT
<213> ORGANISM: Mouse

<400> SEQUENCE: 13

Phe Gln Gly Ser His Val Pro Leu Thr
1 5

<210> SEQ ID NO 14
<211> LENGTH: 12
<212> TYPE: PRT
<213> ORGANISM: Mouse

<400> SEQUENCE: 14

Phe Gly Ala Gly Thr Lys Leu Glu Leu Lys Arg Ala
1 5 10

<210> SEQ ID NO 15
<211> LENGTH: 10
<212> TYPE: PRT
<213> ORGANISM: Mouse

<400> SEQUENCE: 15

Thr Ile Ser Ser Gly Gly Thr Trp Thr Phe
1 5 10

<210> SEQ ID NO 16
<211> LENGTH: 10
<212> TYPE: PRT
<213> ORGANISM: Mouse

<400> SEQUENCE: 16

Thr Ile Ser Ser Gly Gly Ala Trp Thr Phe
1 5 10

<210> SEQ ID NO 17
<211> LENGTH: 10
<212> TYPE: PRT
<213> ORGANISM: Mouse

<400> SEQUENCE: 17

Thr Ile Ser Ser Gly Gly Lys Trp Val Phe
1 5 10

<210> SEQ ID NO 18
<211> LENGTH: 10
<212> TYPE: PRT
<213> ORGANISM: Mouse

<400> SEQUENCE: 18

Thr Ile Ser Ser Gly Gly Glu Trp Thr Phe
1 5 10

<210> SEQ ID NO 19
<211> LENGTH: 16
<212> TYPE: PRT
<213> ORGANISM: Mouse

<400> SEQUENCE: 19

Lys Ser Ser Gln Gly Ile Val His Ser Thr Gly Asn Thr Phe Leu Glu
1 5 10 15

<210> SEQ ID NO 20
<211> LENGTH: 16
<212> TYPE: PRT
<213> ORGANISM: Mouse

<400> SEQUENCE: 20

Lys Ser Ser Ala Gly Ile Val His Ser Thr Gly Asn Thr Phe Leu Glu
1               5                   10                  15

<210> SEQ ID NO 21
<211> LENGTH: 16
<212> TYPE: PRT
<213> ORGANISM: Mouse

<400> SEQUENCE: 21

Lys Ser Ser Gly Gly Leu Val His Ser Thr Gly Asn Thr Phe Leu Glu
1               5                   10                  15

<210> SEQ ID NO 22
<211> LENGTH: 16
<212> TYPE: PRT
<213> ORGANISM: Mouse

<400> SEQUENCE: 22

Lys Ser Ser Gln Gly Leu Val His Ser Thr Gly Asn Thr Phe Leu Glu
1               5                   10                  15

<210> SEQ ID NO 23
<211> LENGTH: 9
<212> TYPE: PRT
<213> ORGANISM: Mouse

<400> SEQUENCE: 23

Phe Gln Gly Ser His Ala Pro Leu Thr
1               5

<210> SEQ ID NO 24
<211> LENGTH: 9
<212> TYPE: PRT
<213> ORGANISM: Mouse

<400> SEQUENCE: 24

Phe Gln Gly Ser Arg Ala Pro Leu Thr
1               5

<210> SEQ ID NO 25
<211> LENGTH: 9
<212> TYPE: PRT
<213> ORGANISM: Mouse

<400> SEQUENCE: 25

Phe Gln Gly Ser His Asp Pro Leu Thr
1               5

<210> SEQ ID NO 26
<211> LENGTH: 9
<212> TYPE: PRT
<213> ORGANISM: Mouse

<400> SEQUENCE: 26

Phe Gln Gly Ser His Cys Pro Leu Thr
1               5

<210> SEQ ID NO 27
<211> LENGTH: 9
<212> TYPE: PRT

<213> ORGANISM: Mouse

<400> SEQUENCE: 27

Phe Gln Gly Ser His Ser Pro Leu Thr
1 5

<210> SEQ ID NO 28
<211> LENGTH: 9
<212> TYPE: PRT
<213> ORGANISM: Mouse

<400> SEQUENCE: 28

Phe Gln Gly Gly Arg Cys Pro Leu Thr
1 5

<210> SEQ ID NO 29
<211> LENGTH: 9
<212> TYPE: PRT
<213> ORGANISM: Mouse

<400> SEQUENCE: 29

Phe Gln Gly Gly Val Cys Pro Leu Thr
1 5

<210> SEQ ID NO 30
<211> LENGTH: 9
<212> TYPE: PRT
<213> ORGANISM: Mouse

<400> SEQUENCE: 30

Phe Gln Gly Ser Thr Cys Pro Leu Thr
1 5

<210> SEQ ID NO 31
<211> LENGTH: 9
<212> TYPE: PRT
<213> ORGANISM: Mouse

<400> SEQUENCE: 31

Phe Gln Gly Ser Lys Cys Pro Leu Thr
1 5

<210> SEQ ID NO 32
<211> LENGTH: 9
<212> TYPE: PRT
<213> ORGANISM: Mouse

<400> SEQUENCE: 32

Phe Gln Gly Ser Ser Ser Pro Leu Thr
1 5

<210> SEQ ID NO 33
<211> LENGTH: 10
<212> TYPE: PRT
<213> ORGANISM: Mouse
<220> FEATURE:
<221> NAME/KEY: MISC_FEATURE
<222> LOCATION: (7)..(7)
<223> OTHER INFORMATION: Xaa= Thr, Ala, Lys or Glu
<220> FEATURE:
<221> NAME/KEY: MISC_FEATURE
<222> LOCATION: (8)..(8)
<223> OTHER INFORMATION: Xaa= Tyr or Trp
<220> FEATURE:
<221> NAME/KEY: MISC_FEATURE
<222> LOCATION: (9)..(9)
<223> OTHER INFORMATION: Xaa= Thr or Val

<400> SEQUENCE: 33

Thr Ile Ser Ser Gly Gly Xaa Xaa Xaa Phe
1 5 10

<210> SEQ ID NO 34
<211> LENGTH: 16
<212> TYPE: PRT
<213> ORGANISM: Mouse
<220> FEATURE:
<221> NAME/KEY: MISC_FEATURE
<222> LOCATION: (4)..(4)
<223> OTHER INFORMATION: Xaa= Gln, Ala or Gly
<220> FEATURE:
<221> NAME/KEY: MISC_FEATURE
<222> LOCATION: (5)..(5)
<223> OTHER INFORMATION: Xaa= Ser or Gly
<220> FEATURE:
<221> NAME/KEY: MISC_FEATURE
<222> LOCATION: (6)..(6)
<223> OTHER INFORMATION: Xaa= Ile or Leu

<400> SEQUENCE: 34

Lys Ser Ser Xaa Xaa Xaa Val His Ser Thr Gly Asn Thr Phe Leu Glu
1 5 10 15

<210> SEQ ID NO 35
<211> LENGTH: 9
<212> TYPE: PRT
<213> ORGANISM: Mouse
<220> FEATURE:
<221> NAME/KEY: MISC_FEATURE
<222> LOCATION: (4)..(4)
<223> OTHER INFORMATION: Xaa = Ser or Gly
<220> FEATURE:
<221> NAME/KEY: MISC_FEATURE
<222> LOCATION: (5)..(5)
<223> OTHER INFORMATION: Xaa = His, Arg, Val, Thr, Lys or Ser
<220> FEATURE:
<221> NAME/KEY: MISC_FEATURE
<222> LOCATION: (6)..(6)
<223> OTHER INFORMATION: Xaa = Val, Ala, Asp, Cys or Ser

<400> SEQUENCE: 35

Phe Gln Gly Xaa Xaa Xaa Pro Leu Thr
1 5

<210> SEQ ID NO 36
<211> LENGTH: 15
<212> TYPE: PRT
<213> ORGANISM: Artificial Sequence
<220> FEATURE:
<223> OTHER INFORMATION: Synthetic

<400> SEQUENCE: 36

Gly Pro Ala Lys Glu Leu Thr Pro Leu Lys Glu Ala Lys Val Ser
1 5 10 15

<210> SEQ ID NO 37
<211> LENGTH: 20
<212> TYPE: DNA
<213> ORGANISM: Artificial Sequence
<220> FEATURE:
<223> OTHER INFORMATION: Synthetic

<400> SEQUENCE: 37
tagcatgact ggtggacagc 20

<210> SEQ ID NO 38
<211> LENGTH: 18
<212> TYPE: DNA

<213> ORGANISM: Artificial Sequence
<220> FEATURE:
<223> OTHER INFORMATION: Synthetic

<400> SEQUENCE: 38
cgtagaatcg agaccgag 18

<210> SEQ ID NO 39
<211> LENGTH: 1350
<212> TYPE: DNA
<213> ORGANISM: Mouse

<400> SEQUENCE: 39
gaggtggaat tggtggagtc tgggggagac ttagtgaagc ctggagggtc cctgaaactc 60
tcctgtgcag cctctggatt cactttcagt agttatggca tgtcttgggt tcgccagacg 120
ccagacaaga ggctggagtg ggtcgcaacc attagtagtg gtggtgcctg gacgttctat 180
ccagacagtg tgaaggggcg cttcaccatc tccagagaca atgccaagaa caccctgtcc 240
ctgcaaatga gcagtctgaa gtctgcagac acagccatgt attactgttc aagacagacc 300
gatggttact cctggtttcc ttattggggc caagggactc tggtcactgt ctctgcaagc 360
gctaaaacaa cagccccatc ggtctatcca ctggcccctg tgtgtggaga tacaactggc 420
tcctcggtga ctctaggatg cctggtcaag ggttatttcc ctgagccagt gaccttgacc 480
tggaactctg gatccctgtc cagtggtgtg cacaccttcc cagctgtcct gcagtctgac 540
ctctacaccc tcagcagctc agtgactgta acctcgagca cctggcccag ccagtccatc 600
acctgcaatg tggcccaccc ggcaagcagc accaaggtgg acaagaaaat tgagcccaga 660
gggcccacaa tcaagccctg tcctccatgc aaatgcccag cacctaacct cttgggtgga 720
ccatccgtct tcatcttccc tccaaagatc aaggatgtac tcatgatctc cctgagcccc 780
atagtcacat gtgtggtggt ggatgtgagc gaggatgacc cagatgtcca gatcagctgg 840
tttgtgaaca acgtggaagt acacacagct cagacacaaa cccatagaga ggattacaac 900
agtactctcc gggtggtcag tgccctcccc atccagcacc aggactggat gagtggcaag 960
gagttcaaat gcaaggtcaa caacaaagac ctcccagcgc ccatcgagag aaccatctca 1020
aaacccaaag ggtcagtaag agctccacag gtatatgtct tgcctccacc agaagaagag 1080
atgactaaga aacaggtcac tctgacctgc atggtcacag acttcatgcc tgaagacatt 1140
tacgtggagt ggaccaacaa cgggaaaaca gagctaaact acaagaacac tgaaccagtc 1200
ctggactctg atggttctta cttcatgtac agcaagctga gagtggaaaa gaagaactgg 1260
gtggaaagaa atagctactc ctgttcagtg gtccacgagg gtctgcacaa tcaccacacg 1320
actaagagct tctcccggac tccgggtaaa 1350

<210> SEQ ID NO 40
<211> LENGTH: 450
<212> TYPE: PRT
<213> ORGANISM: Mouse

<400> SEQUENCE: 40

Glu Val Glu Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Ala Trp Thr Phe Tyr Pro Asp Ser Val

```
    50                  55                  60

Lys Gly Arg Phe Thr Ile Ser Arg Asp Asn Ala Lys Asn Thr Leu Ser
65                  70                  75                  80

Leu Gln Met Ser Ser Leu Lys Ser Ala Asp Thr Ala Met Tyr Tyr Cys
                85                  90                  95

Ser Arg Gln Thr Asp Gly Tyr Ser Trp Phe Pro Tyr Trp Gly Gln Gly
            100                 105                 110

Thr Leu Val Thr Val Ser Ala Ser Ala Lys Thr Thr Ala Pro Ser Val
        115                 120                 125

Tyr Pro Leu Ala Pro Val Cys Gly Asp Thr Thr Gly Ser Ser Val Thr
    130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Thr Ser
            180                 185                 190

Ser Thr Trp Pro Ser Gln Ser Ile Thr Cys Asn Val Ala His Pro Ala
        195                 200                 205

Ser Ser Thr Lys Val Asp Lys Lys Ile Glu Pro Arg Gly Pro Thr Ile
    210                 215                 220

Lys Pro Cys Pro Pro Cys Lys Cys Pro Ala Pro Asn Leu Leu Gly Gly
225                 230                 235                 240

Pro Ser Val Phe Ile Phe Pro Pro Lys Ile Lys Asp Val Leu Met Ile
                245                 250                 255

Ser Leu Ser Pro Ile Val Thr Cys Val Val Val Asp Val Ser Glu Asp
            260                 265                 270

Asp Pro Asp Val Gln Ile Ser Trp Phe Val Asn Asn Val Glu Val His
        275                 280                 285

Thr Ala Gln Thr Gln Thr His Arg Glu Asp Tyr Asn Ser Thr Leu Arg
    290                 295                 300

Val Val Ser Ala Leu Pro Ile Gln His Gln Asp Trp Met Ser Gly Lys
305                 310                 315                 320

Glu Phe Lys Cys Lys Val Asn Asn Lys Asp Leu Pro Ala Pro Ile Glu
                325                 330                 335

Arg Thr Ile Ser Lys Pro Lys Gly Ser Val Arg Ala Pro Gln Val Tyr
            340                 345                 350

Val Leu Pro Pro Pro Glu Glu Glu Met Thr Lys Lys Gln Val Thr Leu
        355                 360                 365

Thr Cys Met Val Thr Asp Phe Met Pro Glu Asp Ile Tyr Val Glu Trp
    370                 375                 380

Thr Asn Asn Gly Lys Thr Glu Leu Asn Tyr Lys Asn Thr Glu Pro Val
385                 390                 395                 400

Leu Asp Ser Asp Gly Ser Tyr Phe Met Tyr Ser Lys Leu Arg Val Glu
                405                 410                 415

Lys Lys Asn Trp Val Glu Arg Asn Ser Tyr Ser Cys Ser Val Val His
            420                 425                 430

Glu Gly Leu His Asn His His Thr Thr Lys Ser Phe Ser Arg Thr Pro
        435                 440                 445

Gly Lys
    450

<210> SEQ ID NO 41
<211> LENGTH: 663
```

<212> TYPE: DNA
<213> ORGANISM: Mouse

<400> SEQUENCE: 41

```
gatgttttga tgacccaaac tccactctcc ctgcctgtca gtcttggaga tcaagcctcc     60

atctcttgca aatctagtca ggggttggtc catagtactg gaaacacctt tttagaatgg    120

tttttgcaga agccaggcca gtctccaaag ctcctgatct acaaaatttc caaccgattt    180

tctggggtcc cagacaggtt cagtggcagt ggatcaggga cagatttcac actcaagatc    240

agcagagtgg agtctgagga tctgggagtt tattactgct ttcaaggttc acatgctccg    300

ctcacgttcg gtgctgggac caagctggag ctgaaacggg cgagcgctga tgctgcacca    360

actgtatcca tcttcccacc atccagtgag cagttaacat ctggaggtgc ctcagtcgtg    420

tgcttcttga acaacttcta ccccaaagac atcaatgtca agtggaagat tgatggcagt    480

gaacgacaaa atggcgtcct gaacagttgg actgatcagg acagcaaaga cagcacctac    540

agcatgagca gcaccctcac gttgaccaag gacgagtatg aacgacataa cagctatacc    600

tgtgaggcca ctcacaagac atcaacttca cccattgtca agagcttcaa caggaatgag    660

tgt                                                                  663
```

<210> SEQ ID NO 42
<211> LENGTH: 221
<212> TYPE: PRT
<213> ORGANISM: Mouse

<400> SEQUENCE: 42

```
Asp Val Leu Met Thr Gln Thr Pro Leu Ser Leu Pro Val Ser Leu Gly
1               5                   10                  15

Asp Gln Ala Ser Ile Ser Cys Lys Ser Ser Gln Gly Leu Val His Ser
            20                  25                  30

Thr Gly Asn Thr Phe Leu Glu Trp Phe Leu Gln Lys Pro Gly Gln Ser
        35                  40                  45

Pro Lys Leu Leu Ile Tyr Lys Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ser Glu Asp Leu Gly Val Tyr Tyr Cys Phe Gln Gly
                85                  90                  95

Ser His Ala Pro Leu Thr Phe Gly Ala Gly Thr Lys Leu Glu Leu Lys
            100                 105                 110

Arg Ala Ser Ala Asp Ala Ala Pro Thr Val Ser Ile Phe Pro Pro Ser
        115                 120                 125

Ser Glu Gln Leu Thr Ser Gly Gly Ala Ser Val Val Cys Phe Leu Asn
    130                 135                 140

Asn Phe Tyr Pro Lys Asp Ile Asn Val Lys Trp Lys Ile Asp Gly Ser
145                 150                 155                 160

Glu Arg Gln Asn Gly Val Leu Asn Ser Trp Thr Asp Gln Asp Ser Lys
                165                 170                 175

Asp Ser Thr Tyr Ser Met Ser Ser Thr Leu Thr Leu Thr Lys Asp Glu
            180                 185                 190

Tyr Glu Arg His Asn Ser Tyr Thr Cys Glu Ala Thr His Lys Thr Ser
        195                 200                 205

Thr Ser Pro Ile Val Lys Ser Phe Asn Arg Asn Glu Cys
    210                 215                 220
```

-continued

<210> SEQ ID NO 43
<211> LENGTH: 357
<212> TYPE: DNA
<213> ORGANISM: Mouse

<400> SEQUENCE: 43
gaggtggaat tggtggagtc tgggggagac ttagtgaagc ctggagggtc cctgaaactc 60
tcctgtgcag cctctggatt cactttcagt agttatggca tgtcttgggt tcgccagacg 120
ccagacaaga ggctggagtg ggtcgcaacc attagtagtg gtggtactta caccttctat 180
ccagacagtg tgaaggggcg cttcaccatc tccagagaca atgccaagaa caccctgtcc 240
ctgcaaatga gcagtctgaa gtctgcagac acagccatgt attactgttc aagacagacc 300
gatggttact cctggtttcc ttattggggc caagggactc tggtcactgt ctctgca 357

<210> SEQ ID NO 44
<211> LENGTH: 119
<212> TYPE: PRT
<213> ORGANISM: Mouse

<400> SEQUENCE: 44

Glu Val Glu Leu Val Glu Ser Gly Gly Asp Leu Val Lys Pro Gly Gly
1 5 10 15

Ser Leu Lys Leu Ser Cys Ala Ala Ser Gly Phe Thr Phe Ser Ser Tyr
20 25 30

Gly Met Ser Trp Val Arg Gln Thr Pro Asp Lys Arg Leu Glu Trp Val
35 40 45

Ala Thr Ile Ser Ser Gly Gly Thr Tyr Thr Phe Tyr Pro Asp Ser Val
50 55 60

Lys Gly Arg Phe Thr Ile Ser Arg Asp Asn Ala Lys Asn Thr Leu Ser
65 70 75 80

Leu Gln Met Ser Ser Leu Lys Ser Ala Asp Thr Ala Met Tyr Tyr Cys
85 90 95

Ser Arg Gln Thr Asp Gly Tyr Ser Trp Phe Pro Tyr Trp Gly Gln Gly
100 105 110

Thr Leu Val Thr Val Ser Ala
115

<210> SEQ ID NO 45
<211> LENGTH: 342
<212> TYPE: DNA
<213> ORGANISM: Mouse

<400> SEQUENCE: 45
gatgttttga tgacccaaac tccactctcc ctgcctgtca gtcttggaga tcaagcctcc 60
atctcttgca aatctagtca gagcattgta catagtactg gaaacacctt tttagaatgg 120
tttttgcaga agccaggcca gtctccaaag ctcctgatct acaaaatttc caaccgattt 180
tctggggtcc cagacaggtt cagtggcagt ggatcaggga cagatttcac actcaagatc 240
agcagagtgg agtctgagga tctgggagtt tattactgct ttcaaggttc acatgttccg 300
ctcacgttcg gtgctgggac caagctggag ctgaaacggg cg 342

<210> SEQ ID NO 46
<211> LENGTH: 114
<212> TYPE: PRT
<213> ORGANISM: Mouse

<400> SEQUENCE: 46

Asp Val Leu Met Thr Gln Thr Pro Leu Ser Leu Pro Val Ser Leu Gly

-continued

```
1               5                   10                  15

Asp Gln Ala Ser Ile Ser Cys Lys Ser Ser Gln Ser Ile Val His Ser
            20                  25                  30

Thr Gly Asn Thr Phe Leu Glu Trp Phe Leu Gln Lys Pro Gly Gln Ser
        35                  40                  45

Pro Lys Leu Leu Ile Tyr Lys Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ser Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

Arg Ala
```

<210> SEQ ID NO 47
<211> LENGTH: 45
<212> TYPE: DNA
<213> ORGANISM: Mouse

<400> SEQUENCE: 47
gcggcccagc cggccatggc cgaggtggaa ttggtggagt ctggg 45

<210> SEQ ID NO 48
<211> LENGTH: 42
<212> TYPE: DNA
<213> ORGANISM: Mouse

<400> SEQUENCE: 48
agactcgagg gcggccgccc gtttcagctc cagcttggtc cc 42

<210> SEQ ID NO 49
<211> LENGTH: 60
<212> TYPE: DNA
<213> ORGANISM: Mouse

<400> SEQUENCE: 49
aaggagttga cgcccctgaa ggaggcgaag gtctctgatg ttttgatgac ccaaactcca 60

<210> SEQ ID NO 50
<211> LENGTH: 60
<212> TYPE: DNA
<213> ORGANISM: Mouse

<400> SEQUENCE: 50
cgcctccttc aggggcgtca actccttggc gggacctgca gagacagtga ccagagtccc 60

<210> SEQ ID NO 51
<211> LENGTH: 53
<212> TYPE: DNA
<213> ORGANISM: Mouse

<400> SEQUENCE: 51
ttcttgtcgc gattttaaaa ggtgtccagt gcgaggtgga attggtggag tct 53

<210> SEQ ID NO 52
<211> LENGTH: 33
<212> TYPE: DNA
<213> ORGANISM: Mouse

<400> SEQUENCE: 52

```
tgttttagcg cttgcagaga cagtgaccag agt                               33


<210> SEQ ID NO 53
<211> LENGTH: 36
<212> TYPE: DNA
<213> ORGANISM: Mouse

<400> SEQUENCE: 53

cccggctcgc gatgcgatgt tttgatgacc caaact                            36


<210> SEQ ID NO 54
<211> LENGTH: 33
<212> TYPE: DNA
<213> ORGANISM: Mouse

<400> SEQUENCE: 54

agcatcagcg ctcgcccgtt tcagctccag ctt                               33


<210> SEQ ID NO 55
<211> LENGTH: 369
<212> TYPE: DNA
<213> ORGANISM: Mouse
<220> FEATURE:
<221> NAME/KEY: CDS
<222> LOCATION: (1)..(369)

<400> SEQUENCE: 55

gag gtc cag ctg caa cag tct gga cct gac ctg gtg aag cct gga gct      48
Glu Val Gln Leu Gln Gln Ser Gly Pro Asp Leu Val Lys Pro Gly Ala
1               5                   10                  15

tca atg aag att tcc tgc aag gct tct ggt tac tca ttc act agc tac      96
Ser Met Lys Ile Ser Cys Lys Ala Ser Gly Tyr Ser Phe Thr Ser Tyr
            20                  25                  30

acc ctg aac tgg gtg agg cag agc cct gga aag aac ctt gag tgg att     144
Thr Leu Asn Trp Val Arg Gln Ser Pro Gly Lys Asn Leu Glu Trp Ile
        35                  40                  45

gga ctt att tat cct tac aat ggt ggt act aat tac aac cag aaa ttc     192
Gly Leu Ile Tyr Pro Tyr Asn Gly Gly Thr Asn Tyr Asn Gln Lys Phe
    50                  55                  60

aac gac aag gcc aca ttt act gtg gac aag tca tcc agc aca gcc tac     240
Asn Asp Lys Ala Thr Phe Thr Val Asp Lys Ser Ser Ser Thr Ala Tyr
65                  70                  75                  80

atg gag ctc ctc agt ctg acg tct gag gac tct gca gtc tat tac tgt     288
Met Glu Leu Leu Ser Leu Thr Ser Glu Asp Ser Ala Val Tyr Tyr Cys
                85                  90                  95

gca agg gtt ggt tac tac gga act act cct tac tat gct atg gac tac     336
Ala Arg Val Gly Tyr Tyr Gly Thr Thr Pro Tyr Tyr Ala Met Asp Tyr
            100                 105                 110

tgg ggt caa gga acc tca gtc acc gtc tcc tca                         369
Trp Gly Gln Gly Thr Ser Val Thr Val Ser Ser
        115                 120


<210> SEQ ID NO 56
<211> LENGTH: 123
<212> TYPE: PRT
<213> ORGANISM: Mouse

<400> SEQUENCE: 56

Glu Val Gln Leu Gln Gln Ser Gly Pro Asp Leu Val Lys Pro Gly Ala
1               5                   10                  15

Ser Met Lys Ile Ser Cys Lys Ala Ser Gly Tyr Ser Phe Thr Ser Tyr
            20                  25                  30

Thr Leu Asn Trp Val Arg Gln Ser Pro Gly Lys Asn Leu Glu Trp Ile
```

-continued

```
        35                  40                  45

Gly Leu Ile Tyr Pro Tyr Asn Gly Gly Thr Asn Tyr Asn Gln Lys Phe
    50                  55                  60

Asn Asp Lys Ala Thr Phe Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Val Gly Tyr Tyr Gly Thr Thr Pro Tyr Tyr Ala Met Asp Tyr
            100                 105                 110

Trp Gly Gln Gly Thr Ser Val Thr Val Ser Ser
        115                 120


<210> SEQ ID NO 57
<211> LENGTH: 339
<212> TYPE: DNA
<213> ORGANISM: Mouse
<220> FEATURE:
<221> NAME/KEY: CDS
<222> LOCATION: (1)..(339)

<400> SEQUENCE: 57

gac att gta ctg acc caa tct cca gct tct ttg gct gtg tct cta ggg       48
Asp Ile Val Leu Thr Gln Ser Pro Ala Ser Leu Ala Val Ser Leu Gly
1               5                   10                  15

cag agg gcc acc atc tcc tgc aga gcc agc aaa agt gtt gat tat tat       96
Gln Arg Ala Thr Ile Ser Cys Arg Ala Ser Lys Ser Val Asp Tyr Tyr
            20                  25                  30

ggc att agt ttt atg aac tgg ttc caa cag aaa cca gga cag cca ccc      144
Gly Ile Ser Phe Met Asn Trp Phe Gln Gln Lys Pro Gly Gln Pro Pro
        35                  40                  45

aaa ctc ctc atc tat gct gca tcc agc caa gga tcc ggg gtc cct gcc      192
Lys Leu Leu Ile Tyr Ala Ala Ser Ser Gln Gly Ser Gly Val Pro Ala
    50                  55                  60

agg ttt agt ggc agt ggg tct ggg aca gac ttc agc ctc agc atc cat      240
Arg Phe Ser Gly Ser Gly Ser Gly Thr Asp Phe Ser Leu Ser Ile His
65                  70                  75                  80

cct atg gag gag gat gat act gca atg tat ttc tgt cag cac agt aag      288
Pro Met Glu Glu Asp Asp Thr Ala Met Tyr Phe Cys Gln His Ser Lys
                85                  90                  95

gag gtt ccg tgg acg ttc ggt gga ggc acc aac ctg gaa atc aaa cgg      336
Glu Val Pro Trp Thr Phe Gly Gly Gly Thr Asn Leu Glu Ile Lys Arg
            100                 105                 110

gcg                                                                  339
Ala


<210> SEQ ID NO 58
<211> LENGTH: 113
<212> TYPE: PRT
<213> ORGANISM: Mouse

<400> SEQUENCE: 58

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Asp Tyr Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Ser Gln Gly Ser Gly Val Pro Ala
    50                  55                  60

Arg Phe Ser Gly Ser Gly Ser Gly Thr Asp Phe Ser Leu Ser Ile His
```

```
65                  70                  75                  80

Pro Met Glu Glu Asp Asp Thr Ala Met Tyr Phe Cys Gln His Ser Lys
                85                  90                  95

Glu Val Pro Trp Thr Phe Gly Gly Gly Thr Asn Leu Glu Ile Lys Arg
            100                 105                 110

Ala


<210> SEQ ID NO 59
<211> LENGTH: 42
<212> TYPE: DNA
<213> ORGANISM: Artificial Sequence
<220> FEATURE:
<223> OTHER INFORMATION: Synthetic

<400> SEQUENCE: 59

ggcccagccg gccatggccg aggtccagct gcaacagtct gg                        42


<210> SEQ ID NO 60
<211> LENGTH: 63
<212> TYPE: DNA
<213> ORGANISM: Artificial Sequence
<220> FEATURE:
<223> OTHER INFORMATION: Synthetic

<400> SEQUENCE: 60

cttcgcctcc ttcaggggcg tcaactcctt ggcgggacct gaggagacgg tgactgaggt     60

tcc                                                                   63


<210> SEQ ID NO 61
<211> LENGTH: 60
<212> TYPE: DNA
<213> ORGANISM: Artificial Sequence
<220> FEATURE:
<223> OTHER INFORMATION: Synthetic

<400> SEQUENCE: 61

caaggagttg acgcccctga aggaggcgaa ggtctctgac attgtactga cccaatctcc     60


<210> SEQ ID NO 62
<211> LENGTH: 44
<212> TYPE: DNA
<213> ORGANISM: Artificial Sequence
<220> FEATURE:
<223> OTHER INFORMATION: Synthetic

<400> SEQUENCE: 62

tctagactcg agggcggccg cccgtttgat ttccaggttg gtgc                      44


<210> SEQ ID NO 63
<211> LENGTH: 9
<212> TYPE: PRT
<213> ORGANISM: Artificial
<220> FEATURE:
<223> OTHER INFORMATION: Synthetic

<400> SEQUENCE: 63

Thr Trp Thr Gln Ser Ile Ser His Val
1               5


<210> SEQ ID NO 64
<211> LENGTH: 9
<212> TYPE: PRT
<213> ORGANISM: Artificial
<220> FEATURE:
<223> OTHER INFORMATION: Synthetic
```

<400> SEQUENCE: 64

Ala Trp Thr Gln Ser Ile Ser His Val
1               5

<210> SEQ ID NO 65
<211> LENGTH: 9
<212> TYPE: PRT
<213> ORGANISM: Artificial
<220> FEATURE:
<223> OTHER INFORMATION: Synthetic

<400> SEQUENCE: 65

Lys Trp Val Gln Ser Ile Ser His Val
1               5

<210> SEQ ID NO 66
<211> LENGTH: 9
<212> TYPE: PRT
<213> ORGANISM: Artificial
<220> FEATURE:
<223> OTHER INFORMATION: Synthetic

<400> SEQUENCE: 66

Glu Trp Thr Gln Ser Ile Ser His Val
1               5

<210> SEQ ID NO 67
<211> LENGTH: 9
<212> TYPE: PRT
<213> ORGANISM: Artificial
<220> FEATURE:
<223> OTHER INFORMATION: Synthetic

<400> SEQUENCE: 67

Thr Tyr Thr Gln Gly Ile Ser His Val
1               5

<210> SEQ ID NO 68
<211> LENGTH: 9
<212> TYPE: PRT
<213> ORGANISM: Artificial
<220> FEATURE:
<223> OTHER INFORMATION: Synthetic

<400> SEQUENCE: 68

Thr Tyr Thr Ala Gly Ile Ser His Val
1               5

<210> SEQ ID NO 69
<211> LENGTH: 9
<212> TYPE: PRT
<213> ORGANISM: Artificial
<220> FEATURE:
<223> OTHER INFORMATION: Synthetic

<400> SEQUENCE: 69

Thr Tyr Thr Gly Gly Leu Ser His Val
1               5

<210> SEQ ID NO 70
<211> LENGTH: 9
<212> TYPE: PRT
<213> ORGANISM: Artificial
<220> FEATURE:
<223> OTHER INFORMATION: Synthetic

<400> SEQUENCE: 70

Thr Tyr Thr Gln Gly Leu Ser His Val
1 5

<210> SEQ ID NO 71
<211> LENGTH: 9
<212> TYPE: PRT
<213> ORGANISM: Artificial
<220> FEATURE:
<223> OTHER INFORMATION: Synthetic

<400> SEQUENCE: 71

Thr Tyr Thr Gln Ser Ile Ser His Ala
1 5

<210> SEQ ID NO 72
<211> LENGTH: 9
<212> TYPE: PRT
<213> ORGANISM: Artificial
<220> FEATURE:
<223> OTHER INFORMATION: Synthetic

<400> SEQUENCE: 72

Thr Tyr Thr Gln Ser Ile Ser Arg Ala
1 5

<210> SEQ ID NO 73
<211> LENGTH: 9
<212> TYPE: PRT
<213> ORGANISM: Artificial
<220> FEATURE:
<223> OTHER INFORMATION: Synthetic

<400> SEQUENCE: 73

Thr Tyr Thr Gln Ser Ile Ser His Asp
1 5

<210> SEQ ID NO 74
<211> LENGTH: 9
<212> TYPE: PRT
<213> ORGANISM: Artificial
<220> FEATURE:
<223> OTHER INFORMATION: Synthetic

<400> SEQUENCE: 74

Thr Tyr Thr Gln Ser Ile Ser His Cys
1 5

<210> SEQ ID NO 75
<211> LENGTH: 9
<212> TYPE: PRT
<213> ORGANISM: Artificial
<220> FEATURE:
<223> OTHER INFORMATION: Synthetic

<400> SEQUENCE: 75

Thr Tyr Thr Gln Ser Ile Ser His Ser
1 5

<210> SEQ ID NO 76
<211> LENGTH: 9
<212> TYPE: PRT
<213> ORGANISM: Artificial
<220> FEATURE:
<223> OTHER INFORMATION: Synthetic

<400> SEQUENCE: 76

Thr Tyr Thr Gln Ser Ile Gly Arg Cys 1 5

<210> SEQ ID NO 77
<211> LENGTH: 9
<212> TYPE: PRT
<213> ORGANISM: Artificial
<220> FEATURE:
<223> OTHER INFORMATION: Synthetic

<400> SEQUENCE: 77

Thr Tyr Thr Gln Ser Ile Gly Val Cys
1 5

<210> SEQ ID NO 78
<211> LENGTH: 9
<212> TYPE: PRT
<213> ORGANISM: Artificial
<220> FEATURE:
<223> OTHER INFORMATION: Synthetic

<400> SEQUENCE: 78

Thr Tyr Thr Gln Ser Ile Ser Thr Cys
1 5

<210> SEQ ID NO 79
<211> LENGTH: 9
<212> TYPE: PRT
<213> ORGANISM: Artificial
<220> FEATURE:
<223> OTHER INFORMATION: Synthetic

<400> SEQUENCE: 79

Thr Tyr Thr Gln Ser Ile Ser Lys Cys
1 5

<210> SEQ ID NO 80
<211> LENGTH: 9
<212> TYPE: PRT
<213> ORGANISM: Artificial
<220> FEATURE:
<223> OTHER INFORMATION: Synthetic

<400> SEQUENCE: 80

Thr Tyr Thr Gln Ser Ile Ser Ser Ser
1 5

<210> SEQ ID NO 81
<211> LENGTH: 9
<212> TYPE: PRT
<213> ORGANISM: Artificial
<220> FEATURE:
<223> OTHER INFORMATION: Synthetic

<400> SEQUENCE: 81

Ala Trp Thr Gln Gly Leu Ser Ser Ser
1 5

<210> SEQ ID NO 82
<211> LENGTH: 9
<212> TYPE: PRT
<213> ORGANISM: Artificial
<220> FEATURE:
<223> OTHER INFORMATION: Synthetic

<400> SEQUENCE: 82

Ala Trp Thr Gln Gly Leu Ser His Ala
1 5

<210> SEQ ID NO 83
<211> LENGTH: 9
<212> TYPE: PRT
<213> ORGANISM: Artificial
<220> FEATURE:
<223> OTHER INFORMATION: Synthetic

<400> SEQUENCE: 83

Ala Trp Thr Gln Ser Ile Gly Arg Cys
1               5

<210> SEQ ID NO 84
<211> LENGTH: 9
<212> TYPE: PRT
<213> ORGANISM: Artificial
<220> FEATURE:
<223> OTHER INFORMATION: Synthetic

<400> SEQUENCE: 84

Ala Trp Thr Gln Ser Ile Ser Ser Ser
1               5

<210> SEQ ID NO 85
<211> LENGTH: 9
<212> TYPE: PRT
<213> ORGANISM: Artificial
<220> FEATURE:
<223> OTHER INFORMATION: Synthetic

<400> SEQUENCE: 85

Ala Trp Thr Gln Gly Leu Gly Arg Cys
1               5

<210> SEQ ID NO 86
<211> LENGTH: 9
<212> TYPE: PRT
<213> ORGANISM: Artificial
<220> FEATURE:
<223> OTHER INFORMATION: Synthetic

<400> SEQUENCE: 86

Thr Tyr Thr Gln Gly Leu Gly Arg Cys
1               5

<210> SEQ ID NO 87
<211> LENGTH: 9
<212> TYPE: PRT
<213> ORGANISM: Artificial
<220> FEATURE:
<223> OTHER INFORMATION: Synthetic

<400> SEQUENCE: 87

Thr Tyr Thr Gln Gly Leu Ser Ser Ser
1               5

<210> SEQ ID NO 88
<211> LENGTH: 9
<212> TYPE: PRT
<213> ORGANISM: Artificial
<220> FEATURE:
<223> OTHER INFORMATION: Synthetic

<400> SEQUENCE: 88

Lys Trp Val Gln Gly Leu Ser His Ser
1               5

<210> SEQ ID NO 89

<211> LENGTH: 9
<212> TYPE: PRT
<213> ORGANISM: Artificial
<220> FEATURE:
<223> OTHER INFORMATION: Synthetic

<400> SEQUENCE: 89

Glu Trp Thr Gln Gly Leu Ser His Ser
1               5

<210> SEQ ID NO 90
<211> LENGTH: 9
<212> TYPE: PRT
<213> ORGANISM: Artificial
<220> FEATURE:
<223> OTHER INFORMATION: Synthetic

<400> SEQUENCE: 90

Glu Trp Thr Gln Ser Ile Gly Val Cys
1               5

<210> SEQ ID NO 91
<211> LENGTH: 9
<212> TYPE: PRT
<213> ORGANISM: Artificial
<220> FEATURE:
<223> OTHER INFORMATION: Synthetic

<400> SEQUENCE: 91

Glu Trp Thr Gly Gly Leu Ser His Ser
1               5

<210> SEQ ID NO 92
<211> LENGTH: 9
<212> TYPE: PRT
<213> ORGANISM: Artificial
<220> FEATURE:
<223> OTHER INFORMATION: Synthetic

<400> SEQUENCE: 92

Ala Trp Thr Gln Gly Leu Ser His Ser
1               5

<210> SEQ ID NO 93
<211> LENGTH: 17
<212> TYPE: PRT
<213> ORGANISM: Artificial
<220> FEATURE:
<223> OTHER INFORMATION: Synthetic

<400> SEQUENCE: 93

Lys Ile Ser Ser Gln Ser Ile Val His Ser Thr Gly Asn Thr Phe Leu
1               5                   10                  15

Glu

<210> SEQ ID NO 94
<211> LENGTH: 10
<212> TYPE: PRT
<213> ORGANISM: Mouse

<400> SEQUENCE: 94

Gly Tyr Ser Phe Thr Ser Tyr Thr Leu Asn
1               5                   10

<210> SEQ ID NO 95
<211> LENGTH: 9
<212> TYPE: PRT

<213> ORGANISM: Mouse

<400> SEQUENCE: 95

Ile Tyr Pro Tyr Asn Gly Gly Thr Asn
1 5

<210> SEQ ID NO 96
<211> LENGTH: 9
<212> TYPE: PRT
<213> ORGANISM: Artificial
<220> FEATURE:
<223> OTHER INFORMATION: Synthetic

<400> SEQUENCE: 96

Ile His Leu Pro Asn Gly Gly Thr Asn
1 5

<210> SEQ ID NO 97
<211> LENGTH: 14
<212> TYPE: PRT
<213> ORGANISM: Mouse

<400> SEQUENCE: 97

Val Gly Tyr Tyr Gly Thr Thr Pro Tyr Tyr Ala Met Asp Tyr
1 5 10

<210> SEQ ID NO 98
<211> LENGTH: 14
<212> TYPE: PRT
<213> ORGANISM: Artificial
<220> FEATURE:
<223> OTHER INFORMATION: Synthetic

<400> SEQUENCE: 98

Val Gly Tyr Tyr Gly Pro Ser Trp Tyr Tyr Ala Met Asp Tyr
1 5 10

<210> SEQ ID NO 99
<211> LENGTH: 15
<212> TYPE: PRT
<213> ORGANISM: Mouse

<400> SEQUENCE: 99

Arg Ala Ser Lys Ser Val Asp Tyr Tyr Gly Ile Ser Phe Met Asn
1 5 10 15

<210> SEQ ID NO 100
<211> LENGTH: 7
<212> TYPE: PRT
<213> ORGANISM: Mouse

<400> SEQUENCE: 100

Ala Ala Ser Ser Gln Gly Ser
1 5

<210> SEQ ID NO 101
<211> LENGTH: 7
<212> TYPE: PRT
<213> ORGANISM: Artificial
<220> FEATURE:
<223> OTHER INFORMATION: Synthetic

<400> SEQUENCE: 101

Ala Ala Ser Lys Arg Ala Ser
1 5

-continued

```
<210> SEQ ID NO 102
<211> LENGTH: 9
<212> TYPE: PRT
<213> ORGANISM: Mouse

<400> SEQUENCE: 102

Gln His Ser Lys Glu Val Pro Trp Thr
1               5


<210> SEQ ID NO 103
<211> LENGTH: 9
<212> TYPE: PRT
<213> ORGANISM: Artificial
<220> FEATURE:
<223> OTHER INFORMATION: Synthetic

<400> SEQUENCE: 103

Gln His Ser Met Gln Val Pro Trp Thr
1               5
```

IMMUNOSUPPRESSANT BINDING ANTIBODIES AND METHODS OF OBTAINING AND USING SAME

RELATED APPLICATION INFORMATION

This application claims priority to U.S. Application No. 60/856,614 filed Nov. 3, 2006 and U.S. Application No. 60/794,370 filed Apr. 24, 2006 which is hereby incorporated by reference in its entirety.

FIELD OF THE INVENTION

Among other things, the present invention relates to antibodies that immunospecifically bind with a high binding affinity to at least one agent of interest, e.g., an immunosuppressive agent. The present invention also relates to methods for producing antibodies to an agent of interest (e.g., an immunosuppressive agent) and immunoassays that employ said antibodies. Additionally, the present invention relates to methods for selecting an antibody for use in a diagnostic immunoassay and methods for selecting an antigen for use in a diagnostic immunoassay. The present invention further relates to the improvement of antibody recognition of an active parent drug in the presence of one or more of its major metabolites.

BACKGROUND OF THE INVENTION

Tacrolimus, also known as FK506, is the generic name for a macrolide immunosuppressant produced by the bacterium *Streptomyces tsukabaensis*, in the soil (See, Inamura, N., et al., *Transplantation,* 45(1):206-209 (1988)). The first generation major metabolites of tacrolimus are 13-O-demethylated tacrolimus ("M-I"), 31-O-demethylated tacrolimus ("M-II"), and 15-O-demethylated tacrolimus ("M-III"). Tacrolimus has been used intravenously and orally for the prevention of organ rejection, particularly in patients receiving liver, kidney or bone marrow transplantation.

Cyclosporine ("CsA") is an immunosuppressive drug obtained from certain soil fungi. While primarily used to prevent organ rejection after transplant, CsA also has been used to treat other illnesses, such as aplastic anemia, or to prevent graft versus host disease (GVHD).

Tacrolimus has an in vivo potency 50-100 times greater than cyclosporine CsA (See, Murthy, J. N., et al., *Clinical Biochemistry,* 31(8):613-617 (1998)). The immunosuppressive effect of tacrolimus is similar to CsA and is thought to be through the selective inhibition of the generation of cytotoxic T cells. Id. At the molecular level, tacrolimus appears to selectively block the early transcriptional activities in the T-cell response. Id. This action of tacrolimus is attributed to the binding of drug to specific cytosolic proteins called immunophilins to form a complex. Id. This complex interacts with calcium dependent calcineurin-calmodulin translocation pathways and inhibits the nuclear translocation of a transcriptional factor ("NF-AT"), which binds to an enhancer polynucleotide sequence of the IL-2 genes needed for the transcription of IL-2 mRNA.

Clinically, tacrolimus is known to reduce rejection episodes in transplant patients. Although therapeutically beneficial, tacrolimus exhibits some toxicity similar to that of CsA, which includes nephrotoxicity, gastrointestinal tract complications and neurotoxicity. Id. Unlike CsA, tacrolimus does not cause hirsutism or hypercholesterolemia. Id. In view of the toxicity issues related to tacrolimus, immunoassays are used to monitor the blood concentrations of tacrolimus in patients receiving treatment with this drug.

A variety of different diagnostic immunoassays are commercially available for monitoring the blood concentrations of tacrolimus. Several of these immunoassays use organic solvents to extract the tacrolimus from whole blood samples. The organic solvent increases the equilibrium dissociation constant ($K_D$) and/or lowers the functional activity of the antibody used in the assays. The reduced activity of the antibody leads to lower assay sensitivity and potentially lowers accuracy and robustness. Attempts have been made to increase assay sensitivity by reducing the amount of organic solvent used during the extraction process. However, reducing the amount of the solvent was found to impact the extraction efficiency and hence the assay reproducibility.

Likewise, a variety of different diagnostic immunoassays are commercially available for monitoring the blood concentrations of CsA, e.g., utilizing an anti-cyclosporine antibody. Current literature suggests that the generation of CsA metabolites can mask the concentration of active parent drug (CsA). The appropriate dosage of CsA immunosuppressant is critical for organ transplantation patients.

Therefore, there is a need in the art for new antibodies that have improved binding characteristics (such as affinity and specificity) that can be used in such diagnostic immunoassays. There also is a need for methods of screening for and obtaining such antibodies.

SUMMARY OF THE INVENTION

In one aspect, the present invention relates to an antibody (e.g., an isolated antibody) which specifically binds to an immunosuppressive agent with an equilibrium dissociation constant ($K_D$) of less than $1.9\times10^{-11}$ M when said antibody has not been exposed to or incubated with at least one selection diluent. Preferably, the antibody has $K_D$ of between $1.89\times10^{-11}$ M and $1.0\times10^{-13}$ M, more preferably, a $K_D$ of between $1.89\times10^{-1}$ M and 1.0×16-12 M.

The immunosuppressive agent immunospecifically bound by said antibody can be a calcineurin inhibitor, a target of rapamycin, an interleukin-2 α-chain blocker, an inhibitor of inosine monophosphate dehydrogenase, an inhibitor of dihydrofolic acid reductase, a corticosteroid or an immunosuppressive antimetabolite.

In another aspect, the present invention relates to an isolated antibody which specifically binds to an immunosuppressive agent with a $K_D$ of less than $1.52\times10^{-10}$ M when said antibody is incubated with, exposed to, or is in the presence of at least one selection diluent.

Preferably, the antibody has $K_D$ of between $1.51\times10^{-10}$ M and $1.0\times10^{-12}$ M, more preferably, a $K_D$ of between $1.51\times10^{-10}$ M and $1.0\times10^{11}$ M.

The immunosuppressive agent immunospecifically bound by said antibody can be a calcineurin inhibitor, a target of rapamycin, an interleukin-2 α-chain blocker, an inhibitor of inosine monophosphate dehydrogenase, an inhibitor of dihydrofolic acid reductase, a corticosteroid or an immunosuppressive antimetabolite.

The at least one selection diluent can comprise a buffer, salt, detergent, binding competitor, solvent or combinations thereof. The buffer can be MES, MOPS, HEPES, TRIS, phosphate, citrate or borate. The salt can be NaCl, KCl or zinc sulfate. The detergent can be an anionic detergent, a cationic detergent, a non-ionic detergent or a zwitterionic detergent. The binding competitor can be a metabolite hapten, hormone, drug, enzyme, receptor, protein, peptide, polypeptide, oligonucleotides, polynucleotide or a cross-reactant having a lower affinity than an epitope of interest. The solvent can be dimethylformamide, dimethyl sulfoxide, polyethylene glycol, ethylene glycol, methanol, ethanol or combinations thereof.

In other aspects, the present invention relates to a Chinese Hamster Ovary cell line 1-60-46 AM2 CHO 2-577 (also known as "CHO Cell Line: Tacrolimus 1-60-46 AM2 CHO 2-577" or "Tacrolimus 1-60-46 AM2 CHO 2-577") having A.T.C.C. Accession No. PTA-7436, an antibody made from DNA extracted from a Chinese Hamster Ovary cell line 1-60-46 AM2 CHO 2-577 having A.T.C.C. Accession No. PTA-7436, and a chimeric antibody or a tacrolimus binding fragment thereof produced by a Chinese Hamster Ovary cell line 1-60-46 AM2 CHO 2-577, wherein said cell line has A.T.C.C. Accession No. PTA-7436.

In yet still other aspects, the present invention relates to a Chinese Hamster Ovary cell line 1-60-46 AM2 CHO 1-1157 (also known as "CHO Cell Line: Tacrolimus 1-60-46 AM2 CHO 1-1157" or "Tacrolimus 1-60-46 AM2 CHO 1-1157" or "1-1157") having A.T.C.C. Accession No. PTA-7446, an antibody made from DNA extracted from a Chinese Hamster Ovary cell line 1-60-46 AM2 CHO 1-1157 having A.T.C.C. Accession No. PTA-7446 and a chimeric antibody or a tacrolimus binding fragment thereof produced by a Chinese Hamster Ovary cell line 1-60-46 AM2 CHO 1-1157, wherein said cell line has A.T.C.C. Accession No. PTA-7446.

In still yet another aspect, the present invention relates to an isolated antibody which specifically binds to tacrolimus, wherein said antibody has a variable heavy domain and a variable light domain, the variable heavy domain comprising a heavy chain complementary determining region ("CDR") 1, a heavy chain CDR 2 and a heavy chain CDR 3, the variable light domain comprising a light chain CDR 1, a light chain CDR 2 and a light chain CDR 3, wherein (a) Heavy Chain CDR 1 has an amino acid sequence of: Gly-Phe-Thr-Phe-Ser-Ser-Tyr-Gly-Met-Ser (SEQ ID NO:2);

(b) Heavy Chain CDR 2 has an amino acid sequence having a formula of: Thr-Ile-Ser-Ser-Gly-Gly-$Xaa_1$-$Xaa_2$-$Xaa_3$-Phe (SEQ ID NO:33)

wherein $Xaa_1$ is selected from the group consisting of threonine (Thr), alanine (Ala), lysine (Lys) and glutamic acid (Glu);

wherein $Xaa_2$ is selected from the group consisting of tyrosine (Tyr) and tryptophan (Trp); and wherein $Xaa_3$ is selected from the group consisting of threonine (Thr) and valine (Val);

(c) Heavy Chain CDR 3 has an amino acid sequence of: Gln-Thr-Asp-Gly-Tyr-Ser-Trp-Phe-Pro-Tyr (SEQ ID NO:6);

(d) Light Chain CDR 1 has an amino acid sequence having a formula of: Lys-Ser-Ser-$Xaa_4$-$Xaa_5$-$Xaa_6$-Val-His-Ser-Thr-Gly-Asn-Thr-Phe-Leu-Glu (SEQ ID NO:34)

wherein $Xaa_4$ is selected from the group consisting of: glutamine (Gln), alanine (Ala) and glycine (Gly);

wherein $Xaa_5$ is selected from the group consisting of: serine (Ser) and glycine (Gly); and wherein $Xaa_6$ is selected from the group consisting of: isoleucine (Ile) and leucine (Leu);

(e) Light Chain CDR 2 has an amino acid sequence having the formula of: Lys-Ile-Ser-Asn-Arg-Phe-Ser (SEQ ID NO:11)

(f) Light Chain CDR 3 has an amino acid sequence having a formula of: Phe-Gln-Gly-$Xaa_7$-$Xaa_8$-$Xaa_9$-Pro-Leu-Thr (SEQ ID NO:35)

wherein $Xaa_7$ is selected from the group consisting of: Serine (Ser) and Glycine (Gly);

wherein $Xaa_8$ is selected from the group consisting of: histidine (His), arginine (Arg), valine (Val), threonine (Thr), lysine (Lys) and serine (Ser); and wherein $Xaa_9$ is selected from the group consisting of: valine (Val), alanine (Ala), aspartic acid (Asp), cysteine (Cys) and Serine (Ser); with the proviso that if in heavy chain CDR 2 $Xaa_1$ is Thr, $Xaa_2$ is Tyr and $Xaa_3$ is Thr and in the light chain CDR $Xaa_4$ is Gln, $Xaa_5$ is Ser and $Xaa_6$ is Ile, then in light chain CDR 3 $Xaa_9$ is other than Val if $Xaa_7$ is Ser and $Xaa_8$ is His, or $Xaa_8$ is other than His if $Xaa_7$ is Ser and $Xaa_9$ is Val or $Xaa_7$ is other than Ser if $Xaa_8$ is His and $Xaa_9$ is Val.

In the above-described antibody: (1) $Xaa_1$ is Thr, $Xaa_2$ is Trp, $Xaa_3$ is Thr, $Xaa_4$ is Gln, $Xaa_5$ is Ser, $Xaa_6$ is Ile, $Xaa_7$ is Ser, $Xaa_8$ is His and $Xaa_9$ is Val; (2) $Xaa_1$ is Ala, $Xaa_2$ is Trp, $Xaa_3$ is Thr, $Xaa_4$ is Gln, $Xaa_5$ is Ser, $Xaa_6$ is Ile, $Xaa_7$ is Ser, $Xaa_8$ is His and $Xaa_9$ is Val; (3) $Xaa_1$ is Lys, $Xaa_2$ is Trp, $Xaa_3$ is Val, $Xaa_4$ is Gln, $Xaa_5$ is Ser, $Xaa_6$ is Ile, $Xaa_7$ is Ser, $Xaa_8$ is His and $Xaa_9$ is Val; (4) $Xaa_1$ is Glu, $Xaa_2$ is Trp, $Xaa_3$ is Thr, $Xaa_4$ is Gln, $Xaa_5$ is Ser, $Xaa_6$ is Ile, $Xaa_7$ is Ser, $Xaa_8$ is His, and $Xaa_9$ is Val; (5) $Xaa_1$ is Thr, $Xaa_2$ is Tyr, $Xaa_3$ is Thr, $Xaa_4$ is Gln, $Xaa_5$ is Gly, $Xaa_6$ is Ile, $Xaa_7$ is Ser, $Xaa_8$ is His, and $Xaa_9$ is Val; (6) $Xaa_1$ is Thr, $Xaa_2$ is Tyr, $Xaa_3$ is Thr, $Xaa_4$ is Ala, $Xaa_5$ is Gly, $Xaa_6$ is Ile, $Xaa_7$ is Ser, $Xaa_8$ is His, and $Xaa_9$ is Val; (7) $Xaa_1$ is Thr, $Xaa_2$ is Tyr, $Xaa_3$ is Thr, $Xaa_4$ is Gly, $Xaa_5$ is Gly, $Xaa_6$ is Leu, $Xaa_7$ is Ser, $Xaa_8$ is His, and $Xaa_9$ is Val; (8) $Xaa_1$ is Thr, $Xaa_2$ is Tyr, $Xaa_3$ is Thr, $Xaa_4$ is Gln, $Xaa_5$ is Gly, $Xaa_6$ is Leu, $Xaa_7$ is Ser, $Xaa_8$ is His, and $Xaa_9$ is Val; (9) $Xaa_1$ is Thr, $Xaa_2$ is Tyr, $Xaa_3$ is Thr, $Xaa_4$ is Gln, $Xaa_5$ is Ser, $Xaa_6$ is Ile, $Xaa_7$ is Ser, $Xaa_8$ is His and $Xaa_9$ is Ala; (10) $Xaa_1$ is Thr, $Xaa_2$ is Tyr, $Xaa_3$ is Thr, $Xaa_4$ is Gln, $Xaa_5$ is Ser, $Xaa_6$ is Ile, $Xaa_7$ is Ser, $Xaa_8$ is Arg, and $Xaa_9$ is Ala; (11) $Xaa_1$ is Thr; $Xaa_2$ is Tyr, $Xaa_3$ is Thr, $Xaa_4$ is Gln, $Xaa_5$ is Ser, $Xaa_6$ is Ile, $Xaa_7$ is Ser, $Xaa_8$ is His, and $Xaa_9$ is Asp; (12) $Xaa_1$ is Thr, $Xaa_2$ is Tyr, $Xaa_3$ is Thr, $Xaa_4$ is Gln, $Xaa_5$ is Ser, $Xaa_6$ is Ile, $Xaa_7$ is Ser, $Xaa_8$ is His, and $Xaa_9$ is Cys; (13) $Xaa_1$ is Thr, $Xaa_2$ is Tyr, $Xaa_3$ is Thr, $Xaa_4$ is Gln, $Xaa_5$ is Ser, $Xaa_6$ is Ile, $Xaa_7$ is Ser, $Xaa_8$ is His, and $Xaa_9$ is Ser; (14) $Xaa_1$ is Thr, $Xaa_2$ is Tyr, $Xaa_3$ is Thr, $Xaa_4$ is Gln, $Xaa_5$ is Ser, $Xaa_6$ is Ile, $Xaa_7$ is Gly, $Xaa_8$ is Arg, and $Xaa_9$ is Cys; (15) $Xaa_1$ is Thr, $Xaa_2$ is Tyr, $Xaa_3$ is Thr, $Xaa_4$ is Gln, $Xaa_5$ is Ser, $Xaa_6$ is Ile, $Xaa_7$ is Gly, $Xaa_8$ is Val, and $Xaa_9$ is Cys; (16) $Xaa_1$ is Thr, $Xaa_2$ is Tyr; $Xaa_3$ is Thr, $Xaa_4$ is Gln, $Xaa_5$ is Ser, $Xaa_6$ is Ile, $Xaa_7$ is Ser, $Xaa_8$ is Thr and $Xaa_9$ is Cys; (17) $Xaa_1$ is Thr, $Xaa_2$ is Tyr, $Xaa_3$ is Thr, $Xaa_4$ is Gln, $Xaa_5$ is Ser, $Xaa_6$ is Ile, $Xaa_7$ is Ser, $Xaa_8$ is Lys, and $Xaa_9$ is Cys; (18) $Xaa_1$ is Thr, $Xaa_2$ is Tyr, $Xaa_3$ is Thr, $Xaa_4$ is Gln, $Xaa_5$ is Ser, $Xaa_6$ is Ile, $Xaa_7$ is Ser, $Xaa_8$ is Ser, and $Xaa_9$ is Ser; (19) $Xaa_1$ is Ala, $Xaa_2$ is Trp, $Xaa_3$ is Thr, $Xaa_4$ is Gln, $Xaa_5$ is Gly, $Xaa_6$ is Leu, $Xaa_7$ is Ser, $Xaa_8$ is Ser, and $Xaa_9$ is Ser; (20) $Xaa_1$ is Ala, $Xaa_2$ is Trp, $Xaa_3$ is Thr, $Xaa_4$ is Gln, $Xaa_5$ is Gly, $Xaa_6$ is Leu, $Xaa_7$ is Ser, $Xaa_8$ is His, and $Xaa_9$ is Ala; (21) $Xaa_1$ is Ala, $Xaa_2$ is Trp, $Xaa_3$ is Thr, $Xaa_4$ is Gln, $Xaa_5$ is Ser, $Xaa_6$ is Ile, $Xaa_7$ is Gly, $Xaa_8$ is Arg, and $Xaa_9$ is Cys; (22) $Xaa_1$ is Ala, $Xaa_2$ is Trp, $Xaa_3$ is Thr, $Xaa_4$ is Gln, $Xaa_5$ is Ser, $Xaa_6$ is Ile, $Xaa_7$ is Ser, $Xaa_8$ is Ser, and $Xaa_9$ is Ser; (23) $Xaa_1$ is Ala, $Xaa_2$ is Trp, $Xaa_3$ is Thr, $Xaa_4$ is Gln, $Xaa_5$ is Gly, $Xaa_6$ is Leu, $Xaa_7$ is Gly, $Xaa_8$ is Arg, and $Xaa_9$ is Cys; (24) $Xaa_1$ is Thr, $Xaa_2$ is Tyr, $Xaa_3$ is Thr, $Xaa_4$ is Gln, $Xaa_5$ is Gly, $Xaa_6$ is Leu, $Xaa_7$ is Gly, $Xaa_8$ is Arg, and $Xaa_9$ is Cys; (25) $Xaa_1$ is Thr, $Xaa_2$ is Tyr, $Xaa_3$ is Thr, $Xaa_4$ is Gln, $Xaa_5$ is Gly, $Xaa_6$ is Leu, $Xaa_7$ is Ser, $Xaa_8$ is Ser, and $Xaa_9$ is Ser; (26) $Xaa_1$ is Lys, $Xaa_2$ is Trp, $Xaa_3$ is Val, $Xaa_4$ is Gln, $Xaa_5$ is Gly, $Xaa_6$ is Leu, $Xaa_7$ is Ser, $Xaa_8$ is His, and $Xaa_9$ is Ser; (27) $Xaa_1$ is Glu, $Xaa_2$ is Trp, $Xaa_3$ is Thr, $Xaa_4$ is Gln, $Xaa_5$ is Gly, $Xaa_6$ is Leu, $Xaa_7$ is Ser, $Xaa_8$ is His, and $Xaa_9$ is Ser; (28) $Xaa_1$ is Glu, $Xaa_2$ is Trp, $Xaa_3$ is Thr, $Xaa_4$ is Gln, $Xaa_5$ is Ser, $Xaa_6$ is Ile, $Xaa_7$ is Gly, $Xaa_8$ is Val, and $Xaa_9$ is Cys; (29) $Xaa_1$ is Glu, $Xaa_2$ is Trp, $Xaa_3$ is Thr, $Xaa_4$ is Gly, $Xaa_5$ is Gly, $Xaa_6$ is Leu, $Xaa_7$ is Ser, $Xaa_8$ is His and $Xaa_9$ is Ser; or (30) $Xaa_1$ is Ala, $Xaa_2$ is Trp, $Xaa_3$ is Thr, $Xaa_4$ is Gln, $Xaa_5$ is Gly, $Xaa_6$ is Leu, $Xaa_7$ is Ser, $Xaa_8$ is His, and $Xaa_9$ is Ser.

The above-described antibody may have a $K_D$ of between $1.89\times10^{-11}$ M and $1.0\times10^{-13}$ M when said antibody has not been exposed to or incubated with at least one selection diluent and a $K_D$ of between 1.51×10 M and $1.0\times10^{-12}$ M when said antibody is incubated with, exposed to, or is in the presence of at least one selection diluent.

The above-described antibody can be monoclonal antibody, a multispecific antibody, a human antibody, a fully humanized antibody, a partially humanized antibody, an animal antibody, a recombinant antibody, a chimeric antibody, a single-chain Fv, a single chain antibody, a single domain antibody, a Fab fragment, a F(ab') fragment, a disulfide-linked Fvs, an anti-idiotypic antibody, or a functionally active epitope-binding fragment thereof.

In yet a further aspect, the present invention relates to a diagnostic immunoassay for tacrolimus, wherein said immunoassay comprises any of the hereinbefore described antibodies. Additionally, said immunoassay can comprise: (1) a single antibody that specifically binds to an immunosuppressive agent; or (2) an additional specific binding partner for tacrolimus.

In yet still a further aspect, the present invention relates to a method for selecting an antibody for use in a diagnostic immunoassay, wherein said antibody binds to an epitope of interest. The method can comprise the following steps:

a) contacting at least one antibody with a sample in the presence of at least one selection diluent, wherein said sample contains an epitope of interest to which said antibody is believed to bind and further wherein said antibody is a present in a bio-display format;

b) determining the equilibrium dissociation constant ($K_D$), disassociation rate constant ($k_d$), association rate constant ($k_a$) or functional activity of the antibody; and c) selecting an antibody based on the equilibrium dissociation constant, dissociation rate constant, association rate constant or functional activity determined in step b).

Alternatively, the method can comprise the following steps:

a) incubating at least one antibody in the presence of at least one selection diluent, wherein said antibody is present in a bio-display format;

b) contacting at least one antibody with a sample, wherein said sample contains an epitope of interest to which said antibody is believed to bind;

c) determining the equilibrium dissociation constant ($K_D$), disassociation rate constant ($k_d$), association rate constant ($k_a$) or functional activity of the antibody; and d) selecting an antibody based on the equilibrium dissociation constant, disassociation rate constant, association rate constant or functional activity determined in step c).

In the above-described methods, the sample can contain an immunosuppressive agent, such as, a calcineurin inhibitor, a target of rapamycin, an interleukin-2 α-chain blocker, an inhibitor of inosine monophosphate dehydrogenase, an inhibitor of dihydrofolic acid reductase, a corticosteroid or an immunosuppressive antimetabolite. Additionally, in the above-described methods, the at least one selection diluent can comprise a buffer, salt, detergent, binding competitor, solvent or combinations thereof. The buffer can be MES, MOPS, HEPES, TRIS, phosphate, citrate or borate. The salt can be NaCl, KCl or zinc sulfate. The detergent can be an anionic detergent, a cationic detergent, a non-ionic detergent or a zwitterionic detergent. The binding competitor can be a metabolite hapten, hormone, drug, enzyme, receptor, protein, peptide, polypeptide, oligonucleotide or polynucleotide. The solvent can be dimethylformamide, dimethyl sulfoxide, polyethylene glycol, ethylene glycol, methanol, ethanol or combinations thereof.

In another embodiment, the present invention relates to a method for selecting an antibody for use in a diagnostic immunoassay, wherein said antibody binds to tacrolimus. The method can comprise the steps of:

a) contacting at least one antibody with tacrolimus in the presence of at least one selection diluent, wherein said antibody is a present in a bio-display format;

b) determining the equilibrium dissociation constant ($K_D$), disassociation rate constant ($k_d$), association rate constant ($k_a$) or functional activity of the antibody; and c) selecting an antibody based on the equilibrium dissociation constant, disassociation rate constant, association rate constant or functional activity determined in step b).

Alternatively, the method can comprise the steps of:

a) incubating at least one antibody in the presence of at least one selection diluent, wherein said antibody is present in a bio-display format;

b) contacting at least one antibody with tacrolimus in the presence of at least one selection diluent;

c) determining the equilibrium dissociation constant ($K_D$), disassociation rate constant ($k_d$), association rate constant ($k_a$) or functional activity of the antibody; and d) selecting an antibody based on the equilibrium dissociation constant, disassociation rate constant, association rate constant or functional activity determined in step c).

Additionally, in the above-described methods, the at least one selection diluent can comprise a buffer, salt, detergent, binding competitor or solvent. The buffer can be MES, MOPS, HEPES, TRIS, phosphate, citrate or borate. The salt can be NaCl, KCl or zinc sulfate. The detergent can be an anionic detergent, a cationic detergent, a non-ionic detergent or a zwitterionic detergent. The binding competitor can be a metabolite hapten, hormone, drug, enzyme, receptor, protein, peptide, polypeptide, oligonucleotide or polynucleotide. The solvent can be dimethylformamide, dimethyl sulfoxide, polyethylene glycol, ethylene glycol, methanol, ethanol or combinations thereof.

In yet another aspect, the present invention relates to a method for selecting a specific binding partner for detecting an analyte of interest in test sample for use in a diagnostic immunoassay. The method can comprises the steps of:

a) contacting a specific binding partner with a sample in the presence of at least one selection diluent, wherein said sample contains the epitope of interest and the specific binding partner binds to the epitope of interest, and further wherein said specific binding partner is present in a bio-display format;

b) determining the equilibrium dissociation constant ($K_D$), disassociation rate constant ($k_d$), association rate constant ($k_a$) or functional activity of the specific binding partner; and c) selecting a specific binding partner based on the equilibrium dissociation constant, dissociation rate constant, association rate constant or functional activity of the specific binding partner determined in step b).

In the above-described method, the sample can contain an immunosuppressive agent, such as, a calcineurin inhibitor, a target of rapamycin, an interleukin-2 α-chain blocker, an inhibitor of inosine monophosphate dehydrogenase, an inhibitor of dihydrofolic acid reductase, a corticosteroid or an immunosuppressive antimetabolite. Additionally, in the above-described method, the at least one selection diluent can comprise a buffer, salt, detergent, binding competitor or solvent. The buffer can be MES, MOPS, HEPES, TRIS, phosphate, citrate or borate. The salt can be NaCl, KCl or zinc sulfate. The detergent can be an anionic detergent, a cationic detergent, a non-ionic detergent or a zwitterionic detergent. The binding competitor can be a metabolite hapten, hormone, drug, enzyme, receptor, protein, peptide, polypeptide, oligonucleotide or polynucleotide. The solvent can be dimethylformamide, dimethyl sulfoxide, polyethylene glycol, ethylene glycol, methanol, ethanol or combinations thereof.

In another embodiment, the invention relates to a method of screening for antibodies having improved specificity for an agent using yeast display. The method optionally comprises the steps of:

(a) obtaining a yeast display library comprising antibodies (e.g., scFvs, optionally which are mutated) present on the surface of yeast cells;

(b) contacting the yeast cells with the agent in the presence of a binding competitor;

(c) identifying yeast cells having antibodies displayed thereon which exhibit binding to the agent in the presence of the binding competitor, wherein such binding indicates an improved specificity for the agent.

Optionally the method is carried out with the binding competitor is present in excess over the agent of interest (e.g., from about 5- to about 100-fold, from about 100-fold to about 1000-fold, about 5-fold, about 10-fold, about 25-fold, about 100-fold, or about 200-fold in excess). Optionally the amount of excess is calculated on a molar basis (e.g., nanomolar excess).

In one embodiment the agent comprises an immunosuppressive agent, and the binding competitor is a metabolite of the immunosuppressive agent. Optionally the immunosuppressive agent is selected from the group consisting of cyclosporines and tacrolimus, and the metabolite is selected from the group consisting of M-I, M-II, M-III, M1, M8, M9, M13, M17, M18, M21 and combinations thereof.

In another embodiment the method of screening is carried out wherein the binding competitor (e.g., metabolite) comprises a plurality of binding competitors (e.g., metabolites). Optionally, the plurality of binding competitors (e.g., metabolites) can comprise two (e.g., metabolites, including but not limited to M17 and M1), three, four, five six, seven, eight, nine or ten binding competitors (e.g., metabolites). When the binding competitor is a metabolite, optionally the plurality of metabolites is selected from the group consisting of M-I, M-II, M-III, M1, M8, M9, M13, M17, M18 and M21.

In yet another preferred embodiment, the method can be employed to obtain antibodies having preferred characteristics (e.g., improved specificity) by carrying out the screening in a stepwise fashion. For instance, instead of comprising a plurality of binding competitors (e.g., metabolites), screening can be carried out using one or more binding competitors (e.g., metabolites) followed by one or more rounds of additional screening using one or more binding competitors (e.g., metabolites).

Moreover, optionally the methods described herein of screening to obtain antibodies having preferred characteristics (e.g., preferred binding characteristics, such as preferred affinity or specificity) can be combined, and used in combination either simultaneously, or sequentially. For example, the methods can relate to a method of screening for antibodies having improved affinity for an epitope of interest. Such a method can comprise the steps of:

(a) obtaining a library comprising antibodies present in a bio-display format wherein said antibodies comprise mutations;

(b) contacting said antibodies with sample comprising said epitope in the presence of at least one selection diluent; and (c) identifying antibodies present in said bio-display format which exhibit reduced dissociation rates in the presence of said selection diluent as compared to the dissociation rate of comparable antibody not comprising mutations, wherein such reduced dissociation rates indicate an improved affinity for said epitope.

Alternatively, the method can comprise the steps of: A method of screening for a specific binding partner having improved affinity for an epitope of interest, said method comprising the steps of:

(a) obtaining a library comprising specific binding partners present in a bio-display format wherein said specific binding partners comprise mutations;

(b) contacting said specific binding partners with sample comprising said epitope in the presence of at least one selection diluent; and (c) identifying specific binding partners present in said bio-display format which exhibit reduced dissociation rates in the presence of said selection diluent as compared to the dissociation rate of a comparable specific binding partner not comprising mutations, wherein such reduced dissociation rates indicate an improved affinity for said epitope.

In the above-described methods, the contacting of said antibodies with said sample and said selection diluent can be done either simultaneously or sequentially. Additionally, in the above-described methods, the at least one selection diluent can comprise a buffer, salt, detergent, binding competitor or solvent. The buffer can be MES, MOPS, HEPES, TRIS, phosphate, citrate or borate. The salt can be NaCl, KCl or zinc sulfate. The detergent can be an anionic detergent, a cationic detergent, a non-ionic detergent or a zwitterionic detergent. The binding competitor can be a metabolite hapten, hormone, drug, enzyme, receptor, protein, peptide, polypeptide, oligonucleotide or polynucleotide. The solvent can be dimethylformamide, dimethyl sulfoxide, polyethylene glycol, ethylene glycol, methanol, ethanol or combinations thereof. Additionally, in the above-described methods, the sample can contain an immunosuppressive agent, such as, a calcineurin inhibitor, a target of rapamycin, an interleukin-2 α-chain blocker, an inhibitor of inosine monophosphate dehydrogenase, an inhibitor of dihydrofolic acid reductase, a corticosteroid or an immunosuppressive antimetabolite.

BRIEF DESCRIPTION OF THE FIGURES

FIGS. 2A and 2B show the nucleic acid sequences of the tacrolimus 1-60-46 WT heavy chain variable ("VH") sequence (SEQ ID NO:43) (FIG. 2A) and the light chain variable ("VL") sequence (SEQ ID NO:45) (FIG. 2B). Three letter codes representing the amino acids encoded by the nucleic acid sequences are shown on top.

FIG. 6 shows a chart comparing the amino acid sequences of the tacrolimus WT 1-60-46 VH regions (SEQ ID NOS:1-7) with mutant clones isolated from mutagenic VH CDR libraries. Clone names are denoted on the left and the various regions comprising the VH sequence are shown across the top. Amino acids that differ from the WT 1-60-46 sequence are in bold and underlined. The CDR H2 regions of various mutant clones are shown in SEQ ID NOS:15-18.

FIGS. 7A-7B show a chart comparing the amino acid sequences of the tacrolimus WT 1-60-46 VL regions (SEQ ID NOS:8-14) with the mutant clones isolated from mutagenic VL CDR libraries. The clone names are denoted on the left and the various regions comprising the VH sequence are shown across the top. Amino acids that differ from the WT 1-60-46 sequence are in bold and underlined (FIG. 7A). The CDR L1 regions of the mutant clones are shown in SEQ ID NOS:19-22 (FIG. 7B). The CDR L3 regions of the mutant clones are shown in SEQ ID NOS:23-32.

FIG. 8 shows a chart comparing the affinity parameters of the tacrolimus WT 1-60-46 scFv clone to unique mutants. The clone names are denoted on the left. Clones containing various mutational combinations are named by sequential listing of the clones that contain the individual mutations. The affinity parameters tested (with or without 10% methanol) are shown across the top. Improvement values were determined using the ratio of the WT 1-60-46 scFv value to the mutant scFv value for the parameter described.

FIG. 9A shows the dissociation rate analysis. Antigen-binding signals were normalized against a no dissociation control rx for each clone and plotted versus time as measured in seconds. FIG. 9B shows the equilibrium dissociation constant ($K_D$) analysis. Antigen-binding signals were normalized to the maximal mean fluorescence intensity value at saturating antigen conditions for each clone and plotted against concentration of antigen (which is referred to as "bt-tacro").

FIG. 10A shows a chart comparing the amino acid residues (i.e., SEQ ID NOS: 2, 4, 6, 9, 11, 13, 16, 17, 22, 23, 27, 28, and 32) in all of the VH and VL CDR regions from the tacrolimus 1-60-46 mutant clones converted into IgG with the WT 1-60-46 (WT) sequence. The various mutational combinations present in any given sequence are denoted on the left by sequential listing of the clones that contain the individual mutations. The resulting nomenclature for each 1-60-46 mutant IgG produced is shown on the right (namely, AM1, AM2, AM3, AM4 or AM5). Amino acids that differ from the WT 1-60-46 sequence are in bold and underlined.

FIG. 10B shows a graph showing immunoassay results comparing WT 1-60-46 IgG with various 1-60-46 mutant IgG (AM1, AM2 or AM3) using an assay extraction buffer (the assay extraction buffer contained 90% methanol, 10% ethylene glycol and 100 mM zinc sulfate). Microparticles coated with the denoted IgGs were incubated with labeled tacrolimus antigen (which was used as a tracer) at various concentrations of unlabeled tacrolimus antigen (0 ng/ml-30 ng/ml). The ratio of the tracer signal (which is shown on the X-axis) is plotted against the concentration of unlabeled tacrolimus (which is shown on the Y-axis).

FIG. 11 shows the nucleic acid sequence of the tacrolimus 1-60-46 AM2 murine heavy chain IgG (SEQ ID NO:39). The corresponding amino acid sequence (SEQ ID NO:40) encoded by the nucleic acid sequence is shown on top.

FIG. 12 shows the nucleic acid sequence of the tacrolimus 1-60-46 AM2 murine light chain (SEQ ID NO:41). The corresponding amino acid sequence (SEQ ID NO:42) encoded by the nucleic acid sequence is on top.

FIGS. 13A and 13B show the nucleic acid sequences of the cyclosporine hybridoma 29-56-14 WT heavy chain variable (VH) sequence (SEQ ID NO:55) and the light chain variable (VL) sequence (SEQ ID NO:57). Three letter codes representing the amino acids (SEQ ID NOS: 56 and 58, respectively) encoded by the nucleic acid sequences are shown on top.

FIG. 14 shows 29-56-14 WT and combinatorial mutant R2-9 CDR sequences (i.e., SEQ ID NOS: 94-103). Amino acid mutations that contribute to improved cross-reactivity were identified for mutant R2-9 in CDR-H2, H3, L2, and L3. Mutated sequences that differed from CsA 29-56-14 WT are indicated in bold and underlined type.

FIG. 16 shows the structure of cyclosporine A (on the left) and a metabolite of cyclosporine A (on the right), which is referred to herein as "AM1 or M17". The molecular formula and molecular weight of cyclosporine A and metabolite M17 (AM1) are listed below the corresponding structure.

DETAILED DESCRIPTION OF THE INVENTION

Definitions

Figure 1B:
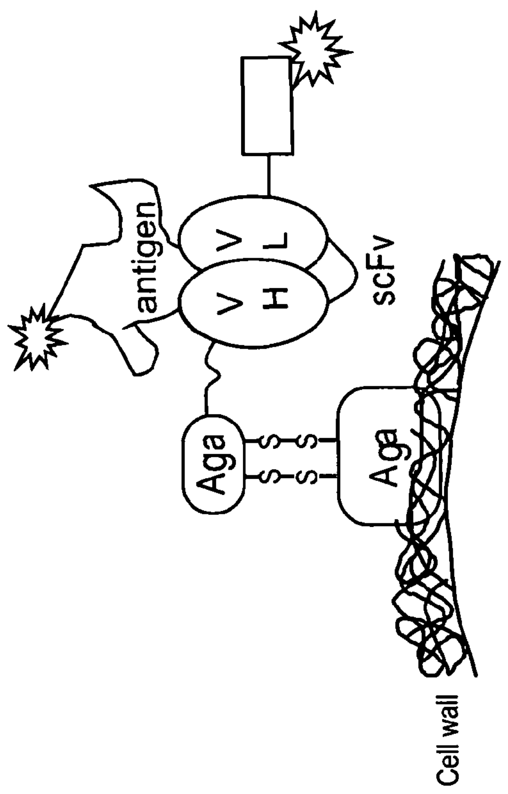
FIG. 1B shows a schematic of yeast cell surface display of scFv antibody.
Figure 1A:
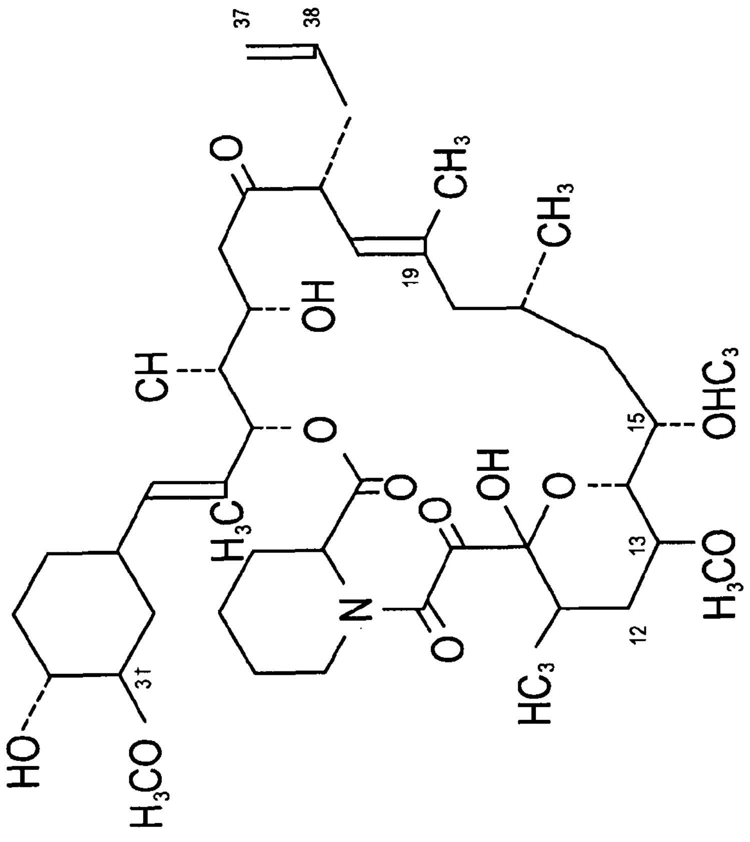
FIG. 1A shows the structure of tacrolimus.

As used herein, the terms "antibody" and "antibodies" refer to monoclonal antibodies, multispecific antibodies, human antibodies, humanized antibodies (fully or partially humanized), animal antibodies (such as, but not limited to a, a bird (for example, a duck or goose), a shark or whale, a mammal, including a non-primate (for example, a cow, pig, camel, llama, horse, goat, rabbit, sheep, hamsters, guinea pig, cat, dog, rat, mouse, etc) or a non-human primate (for example, a monkey, such as a cynomologous monkey, a chimpanzee, etc), recombinant antibodies, chimeric antibodies, single-chain Fvs ("scFv"), single chain antibodies, single domain antibodies, Fab fragments, F(ab') fragments, disulfide-linked Fvs ("sdFv"), and anti-idiotypic ("anti-Id") antibodies (including, for example, anti-Id antibodies to antibodies of the present invention), and functionally active epitope-binding fragments of any of the above. In particular, antibodies include immunoglobulin molecules and immunologically active fragments of immunoglobulin molecules, namely, molecules that contain an antigen binding site. Immunoglobulin molecules can be of any type (for example, IgG, IgE, IgM, IgD, IgA and IgY), class (for example, $IgG_1$, $IgG_2$, $IgG_3$, $IgG_4$, $IgA_1$ and $IgA_2$) or subclass. An antibody whose affinity (namely, $K_D$, $k_d$ or $k_a$) has been increased or improved via the screening of a combinatory antibody library that has been prepared using bio-display, is referred to herein as an "affinity maturated antibody".

As used herein, "specific" or "specificity" in the context of an interaction between members of a specific binding pair (as defined herein, e.g., an antigen and antibody) refers to the selective reactivity of the interaction.

As used herein, the term "association rate constant", "$k_{on}$" or "$k_a$" as used interchangeably herein, refers to the value indicating the binding strength (degree) of an antibody to its target antigen or the rate of complex formation between an antibody and antigen as shown by the below:

$$\text{Antibody}(\text{“}Ab\text{”})+\text{Antigen}(\text{“}Ag\text{”})\rightarrow Ab\text{–}Ag$$

Methods for determining association rate constants are well known in the art. For example, a Biacore® (Sweden) assay can be used. Additionally, a KinExA® (Kinetic Exclusion Assay) assay, available from Sapidyne Instruments (Boise, Id.) can also be used.

As used herein, the term "bio-display" or "bio-display format" refers to any in vitro display system or methodology that couples the genotype of a gene of interest to its encoded phenotype, thereby allowing the polynucleotide (DNA) sequence encoding the protein exhibiting a trait of interest to be recovered. Examples of bio-display systems or methodologies include, but are not limited to, yeast display, phage display, bacterial display, ribosomal/mRNA display, DNA display and in vitro compartmentalization. More specifically, as described in more detail herein, a tacrolimus 1-60-46 antibody was constructed, cloned into a plasmid thereby allowing inducible expression on the surface of the yeast *Saccharomyces cerevisiae* and stably transformed into said yeast host by virtue of an auxotrophic marker present on the plasmid.

As used herein, the term "binding competitor" refers to any molecule that competes or cross-reacts with a molecule containing an epitope of interest from interacting or binding with its specific binding partner. Preferably, the molecule that competes or cross-reacts with the molecule containing the epitope of interest binds to the specific binding partner with a lower affinity (such as, but not limited to, a lower $K_D$, a higher $k_d$ or a lower $k_a$) than the molecule containing the epitope of interest. Examples of a binding competitor include, but are not limited to, metabolites (for example, metabolites of drugs, including but not limited to immunosuppressive agents), such as 13-O-demethylated tacrolimus ("M-I"), 31-O-demethylated tacrolimus ("M-II") and 15-O-demethylated tacrolimus ("M-III"), which are metabolites of tacrolimus or M1, M8, M9, M13 M17, M18 or M21, which are the metabolites of cyclosporine, haptens, hormones, drugs, enzymes, receptors, proteins, peptides, polypeptides, oligonucleotides or polynucleotides. For example, cyclosporine antibody has $K_D$ for parent cyclosporine drug of $9.5\times10^{-10}$ M and $K_D$ for metabolite M17 of $1.45\times10^{-8}$ M.

As used herein, the terms "cross-reacts" or "cross-reactivity" refers to the ability of two epitopes, molecules or ligands to react with the same site on the same specific binding partner, typically with different affinities.

As used herein, the term "disassociation rate constant", "$k_{off}$" or "$k_d$" as used interchangeably herein, refers to the value indicating the disassociation strength (degree) of an antibody from its target antigen or separation of Ab–Ag complex over time into free Ab and antigen as shown by the below:

$$Ab+Ag\leftarrow Ab\text{–}Ag$$

Methods for determining disassociation rate constants are well known in the art. For example, a Biacore® (Sweden) assay can be used. Additionally, a KinExA® (Kinetic Exclusion Assay) assay, available from Sapidyne Instruments (Boise, Id.) can also be used.

As used herein, the term "inhibition constant", "$K_i$", refers to the concentration of binding competitor that would occupy 50% of the available binding sites of one member of a specific binding pair (e.g., antibody) in the absence of the other member of the specific binding pair (e.g., antigen specifically recognized by said antibody) as shown by the equation below:

$$Ki=IC_{50}/(1+([A]/KD))$$

where $IC_{50}$ equals the concentration of binding competitor which displaces 50% of the specific binding at a particular concentration of labeled antigen, [A] equals the concentration of labeled antigen used in the assay, and KD equals the equilibrium dissociation constant of the members of the specific binding pair (e.g., antigen and antibody).

As used herein, the term "epitope", "epitopes" or "epitopes of interest" refer to a site(s) on any molecule that is recognized and is capable of binding to a complementary site(s) on its specific binding partner. The molecule and specific binding partner are part of a specific binding pair. For example, an epitope can be a polypeptide, protein, hapten, carbohydrate antigen (such as, but not limited to, glycolipids, glycoproteins or lipopolysaccharides) or polysaccharide and its specific binding partner, can be, but is not limited to, an antibody.

As used herein, the term "equilibrium dissociation constant" or "$K_D$" as used interchangeably, herein, refers to the value obtained by dividing the disassociation rate constant ($k_{off}$) by the association rate constant ($k_{on}$). The association rate constant, the disassociation rate constant and the equilibrium dissociation constant are used to represent the binding affinity of an antibody to an antigen.

As used herein, the term "humanized" antibody refers to an immunoglobulin variant or fragment thereof, which is capable of binding to a predetermined antigen and which comprises framework regions having substantially the amino acid sequence of a human immunoglobulin and CDRs having substantially the amino acid sequence of a non-human immunoglobulin. Ordinarily, a humanized antibody has one or more amino acid residues introduced into it from a source that is non-human. In general, the humanized antibody will include substantially all of at least one, and typically two, variable domains (such as, Fab, Fab', $F(ab')_2$, Fabc, Fv) in which all or substantially all of the CDR regions correspond to those of a non-human immunoglobulin and all or substantially all of the framework ("FR") regions are those of a human immunoglobulin consensus sequence. The humanized antibody optimally comprises at least a portion of an immunoglobulin constant region ("Fc"), typically that of a human immunoglobulin. Generally, the antibody will contain both the light chain as well as at least the variable domain of a heavy chain. The humanized antibody can be selected from any class of immunoglobulins, including IgM, IgG, IgD, IgA and IgE, and any isotype, including $IgG_1$, $IgG_2$, $IgG_3$ and $IgG_4$. The humanized antibody may comprise sequences from more than one class or isotype, and selecting particular constant domains to optimize desired effector functions is within those skilled in the art.

As used herein, the phrase "specifically binds to an immunosuppressive agent" and analogous terms thereof refer to peptides, polypeptides, proteins, fusion proteins and antibodies that specifically bind to an immunosuppressive agent (such as, but not limited to, tacrolimus) and that do not specifically bind to other competitors (such as, but not limited to, metabolites, peptides, polypeptides, proteins, agents or drugs). A peptide, polypeptide, protein, or antibody that specifically binds to an immunosuppressive agent may bind to other metabolites, peptides, polypeptides, proteins, agents or drugs with lower binding affinity as determined by, for example, diagnostic immunoassays, BIAcore®, KinExA® or other assays known in the art. Antibodies or antibody fragments that immunospecifically bind to an immunosuppressive agent can be identified, for example, by diagnostic immunoassays, BIAcore®, KinExA® or other techniques known to those of skill in the art. An antibody binds immunospecifically to an immunosuppressive agent with a higher binding affinity than to any cross-reactive antigen as determined using experimental techniques, such as, but not limited to, radioimmunoassays ("RIA") and enzyme-linked immunosorbent assays ("ELISAs") (See, for example, Paul, ed., *Fundamental Immunology,* 2nd ed., Raven Press, New York, pages 332-336 (1989)). For example, in the present invention, an antibody binds immunospecifically to an immunosuppressive agent when it exhibits, as an immunoglobulin, an equilibrium disassociation constant ($K_D$) for the immunosuppressive agent of at less than $1.9\times10^{-11}$ M in the absence of a selection diluent (such as, a selection diluent containing phosphate buffered saline ("PBS"), 1% bovine serum albumin ("BSA"), and 10% methanol) or less than $1.52\times10^{-10}$ M when exposed to, incubated with or in the presence of a selection diluent (such as, a selection diluent containing PBS, 1% BSA and 10% methanol) as determined by a KinExA® assay under standard assay conditions (as proscribed by the manufacturer), and in particular the KinExA® assay described in Example 10.

As used herein, the term "immunosuppressive agent" refers to a drug that slows or halts immune system activity in a subject. Immunosuppressive agents can be given to a subject to prevent the subject's immune system from mounting an immune response after an organ transplant or for treating a disease that is caused by an overactive immune system. Examples of immunosuppressive agents include, but are not limited to, a calcineurin inhibitor, such as, but not limited to, cyclosporine, ISA(TX) 247, tacrolimus or calcineurin, a target of rapamycin, such as, but not limited to, sirolimus, everolimus, FK778 or TAFA-93, an interleukin-2 α-chain blocker, such as, but not limited to, basiliximab and daclizumab, an inhibitor of inosine monophosphate dehydrogenase, such as mycophenolate mofetil, an inhibitor of dihydrofolic acid reductase, such as, but not limited to, methotrexate, a corticosteroid, such as, but not limited to, prednisolone and methylprednisolone, or an immunosuppressive antimetabolite, such as, but not limited to, azathioprine.

As used herein, the term "isolated" in the context of nucleic acid molecules refers to a nucleic acid molecule which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the phrase "physiological diluent" refers to any liquid or solid material that can be used to mimic, approximate or simulate the in vivo physiological conditions of the subject (preferably a human), from which said sample (such as a test sample) is derived. The composition of the physiological diluent is not critical and will vary depending on how the physiological diluent is to be used. For example, a physiological diluent can comprise at least one buffer (the at least one buffer can be used to modulate (increase or decrease) the pH of the sample), at least one salt (the at least one salt can be used to modulate (increase or decrease) the salt concentration of the sample), at least one protein (the at least one protein can be used to prevent non-specific binding or to stabilize other proteins contained in the sample), etc. Moreover, a physiological diluent may comprise any combinations of at least one buffer, at least one salt, at least one protein, etc.

For example, it is well known in the art that once a test sample is obtained from a subject, said test sample is no longer considered to be under "physiological conditions" or "non-physiological". Prior to using said test sample in an assay, a physiological diluent can be used and added to the test sample to mimic, approximate or simulate the in vivo physiological conditions of the subject from whom the test sample was derived, or, in other words, to make the test sample more "physiological-like". A test sample is considered to mimic, approximate or simulate physiological conditions or to be "physiological-like" when said test sample (a) has a pH between 7.35 to 7.45; (b) contains sodium salt in the amount of 136 to 146 mmole/L; (c) contains potassium salt in the amount of 3.5 to 5.1 mmole/L; (d) contains zinc in the amount of 10.7 to 22.9 μmole/L; (e) contains methanol in an amount less than 0.05 mmole/L; or (f) any combinations of (a)-(e). (The physiological conditions of test samples is described in Tietz, ed., *Clinical Guide to Laboratory Tests*, WB Saunders, Philadelphia, Pa., page 695 (1983)), which is herein incorporated by reference).

Examples of buffers that can be used, include, but are not limited to, MES, MOPS, HEPES, TRIS, phosphate, citrate, borate buffers or combinations thereof.

Examples of salts that can be used are sodium chloride, potassium chloride, zinc sulfate or combinations thereof.

Examples of proteins that can be used are bovine serum albumin ("BSA"), fish gelatin, bovine gamma globulin or combinations thereof.

As used herein, the term "selection diluent" refers to any liquid or solid material that: (a) is known to one skilled in the art to alter the equilibrium dissociation constant ($K_D$) of at least one antibody or is believed by one skilled in the art likely to alter the $K_D$ of at least one antibody if said antibody were incubated with, used with, or exposed to said selection diluent; (b) known to one skilled in the art to alter the functional activity of at least one antibody or is believed by one skilled in the art likely to alter the functional activity of at least one antibody if said antibody were incubated with, used with, or exposed to said selection diluent; or (c) any combinations of (a)-(b) described above. The selection diluent described herein can be used in a variety of ways, preferably, however, the selection diluent is used to approximate, mimic or simulate the reaction conditions of a diagnostic immunoassay. The composition of the selection diluent is not critical and will vary depending on how the selection diluent is to be used. For example, a selection diluent can comprise at least one buffer, at least one salt, at least one detergent, at least one binding competitor, at least one solvent, etc. Moreover, a selection diluent may comprise any combinations of at least one buffer, at least one salt, at least one detergent, at least one binding competitor, at least one solvent, etc. By way of another example, a selection diluent can comprise PBS (pH 7.4), 1% BSA and 10% methanol. By yet of another example, a selection diluent can comprise PBS (pH 7.4), 1% BSA and about 5 to about 200 nM of a binding competitor. However, as indicated previously the amount of excess of binding competitor can vary, such that the amount of binding competitor in the selection diluent can range, e.g., from about 5 to about 100 nM, from about 100 to about 1000 nM, about 5 nM, about 10 nM, about 25 nM, about 100 nM, or about 200 nM.

An assay extraction buffer used in a diagnostic assay comprising a combination of solvents and at least one salt, such as 90% methanol, 10% ethylene glycol and zinc sulfate (such as 100 mM zinc sulfate), can be used to extract tacrolimus from the serum proteins contained in a whole blood test sample obtained from a subject who is receiving such an immunosuppressive agent as a part of the subject's treatment. The assay extraction buffer used to extract tacrolimus from whole blood test samples is subsequently diluted before it encounters a detection reagent, such as an antibody. Despite the dilution, a certain amount of the extraction buffer (for example, 10% methanol) is still present (or remains) in the test sample and is known to increase the $K_D$, lower the functional activity, or increase the $K_D$ and lower the functional activity of the antibodies used in diagnostic immunoassays for monitoring the blood concentrations of tacrolimus in the above-described subjects. One skilled in the art may expect that such extraction buffers containing these organic solvents would likely increase the $K_D$ (and thus decrease the $k_a$ and increase the $k_d$), likely lower the functional activity, or likely increase the $K_D$ and lower the functional activity of future antibodies developed for use in such diagnostic immunoassays. Therefore, a selection diluent, such as a selection diluent containing PBS, 1% BSA and 10% methanol, can be used to mimic, approximate or simulate the reaction conditions of a diagnostic immunoassay that are likely to increase the $K_D$, likely lower the functional activity, or likely increase the $K_D$ and lower the functional activity of an antibody to be tested.

By way of yet another example, a selection diluent comprising one or more binding competitors can be used to compete with one or other molecules for binding to an epitope of interest or that interferes with the binding of one or more other molecules to bind to an epitope of interest in the test sample. Specifically, a selection diluent comprising one or more binding competitors can alter the conditions of a test sample by displacing or preventing binding of an analyte of interest to another component of the test sample. Alternatively, a selection diluent comprising one or more binding competitors can be used in order to test and/or isolate detection reagents (such as a labeled antibody) having greater specificity for the analyte of interest. For example, a selection diluent comprising one or more binding competitors can be used to determine the degree of cross-reactivity an antibody has for one or more binding competitors or can be used to provide conditions to isolate an antibody with improved (i.e. lowered) cross-reactivity to one or more binding competitors. Along these lines, the present invention provides among other things for the improvement of antibody recognition of active parent drug (e.g., cyclosporine or tacrolimus) in the presence of one or more of their respective major metabolites (e.g., M-I, M-II, M-III, M1, M8, M9, M13, M17, M18 and M21).

Examples of buffers that can be used, include, but are not limited to, MES, MOPS, HEPES, TRIS, phosphate, citrate, borate buffers or combinations thereof.

Examples of salts that can be used are sodium chloride, potassium chloride, zinc sulfate or combinations thereof.

Examples of detergents that can be used include, but are not limited to, anionic detergents, cationic detergents, non-ionic detergents or zwitterionic detergents. A selection diluent containing one or more detergents can be used to stabilize and/or solubilize proteins or other analytes of interest contained within a sample, such as a test sample, to prevent nonspecific binding during the course of a diagnostic immunoassay, to rupture cells contained within a sample, etc. Anionic detergents include, but are not limited to, chenodeoxycholic acid, chenodeoxycholic acid sodium salt, cholic acid, dehydrocholic acid, digitonin, digitoxigenin, N,N-dimethyldodecylamine N-oxide, docusate sodium salt, glycochenodeoxycholic acid sodium salt, glycocholic acid hydrate, glycocholic acid sodium salt hydrate, glycodeoxycholic acid monohydrate, glycolithocholic acid 3-sulfate disodium salt, glycolithocholic acid ethyl ester, N-lauroylsarcosine sodium salt, N-lauroylsarcosine solution, lithium dodecyl sulfate, lugol solution, 1-octanesulfonic acid sodium salt, sodium 1-butanesulfonate, sodium 1-decanesulfonate, sodium 1-dodecanesulfonate, sodium 1-heptanesulfonate anhydrous, sodium 1-nonanesulfonate, sodium 1-propanesulfonate monohydrate, sodium 2-bromoethanesulfonate, sodium cholate hydrate, sodium choleate, sodium deoxycholate, sodium deoxycholate monohydrate, sodium dodecyl sulfate, sodium hexane sulfonate anhydrous, sodium octyl sulfate, sodium pentanesulfonate anhydrous, sodium taurocholate, taurochenodeoxycholic acid sodium salt, taurodeoxycholic acid sodium salt monohydrate, taurodeoxycholic acid sodium salt hydrate, taurolithocholic acid 3-sulfate disodium salt, tauroursodeoxycholic acid sodium salt, ursodeoxycholic acid or combinations thereof, all available from Sigma-Aldrich, St. Louis, Mich.

Cationic detergents include, but are not limited to, alkyltrimethylammonium bromide, benzalkonium chloride, benzyldimethylhexadecylammonium chloride, benzyldimethylhexadecylammonium bromide, benzyltrimethylammonium tetrachloroiodate, dimethyldioctadecylammonium bromide, dodecylethyldimethylammonium bromide, dodecyltrimethylammonium bromide, ethylhexadecyldimethylammonium bromide, Girard's reagent T, hexadecyltrimethylammonium bromide or combinations thereof, all available from Sigma-Aldrich, St. Louis, Mich.

Non-ionic detergents, include, but are not limited, to BigCHAP, bis(polyethylene glycol bis[imidazoyl carbonyl]), Brij®35, Brij®56, Brij®72, Cremophor® EL, decaethylene glycol monododecyl ether, N-decanoyl-N-methylglucamine, n-decyl α-D-maltoside, n-dodecyl β-D-maltoside, heptaethylene glycol monodecyl ether, hexaethylene glycol monododecyl ether, octaethylene glycol monodecyl ether, octaethylene glycol monododecyl ether, octaethylene glycol monohexadecyl ether, octaethylene glycol monooctadecyl ether, octaethylene glycol monotetradecyl ether, pentaethylene glycol monodecyl ether, pentaethylene glycol monododecyl ether, pentaethylene glycol monohexadecyl ether, pentaethylene glycol monohexyl ether, pentaethylene glycol monooctadecyl ether, polyethylene glycol diglycidyl ether, polyethylene glycol ether W-1, polyoxyethylene 10 tridecyl ether, polyoxyethylene 100 stearate, polyoxyethylene 20 isohexadecyl ether, saponin, Span®20, Span®40, Span®60, Span®65, Span®80, Span®85, Terigol, Triton CF-21, Triton CF-32, Triton DF-12, Triton DF-16, Triton GR-5M, Triton QS-15, Triton QS-44, Triton X-100, Triton X-102, Triton X-15, Triton®X-100, Triton® X-114, TWEEN®20, TWEEN®21, TWEEN®40, TWEEN®60, TWEEN®61, TWEEN®65, TWEEN®80, TWEEN®81, TWEEN®85 or combinations thereof, all available from Sigma-Aldrich, St. Louis, Mich.

Zwitterionic detergents include, but are not limited to, CHAPS, 3-(Decyldimethylammonio)propanesulfonate inner salt, (Dodecyldimethylammonio)propanesulfonate inner salt, 3-(N,N-Dimethylmyristylammonio)propanesulfonate, 3-(N,N-Dimethyloctadecylammonio)propanesulfonate, 3-(N,N-dimethyloctylammonio)propsanesulfonate inner salt, 3-(N,N-dimethylpalmitylammonio)proposanesulfonate or combinations thereof, all available from Sigma-Aldrich, St. Louis, Mich.

Examples of solvents that can be used are organic solvents. Examples of organic solvents that can be used include, but are not limited to, dimethylformamide, dimethyl sulfoxide, polyethylene glycol, ethylene glycol, methanol, ethanol or combinations thereof. A preferred solvent is 90% methanol that can be reduced to 10% prior to incubation with a detection reagent, such as, but not limited to, an antibody.

As used herein, the term “specific binding partner” means a member of a specific binding pair. The members of a specific binding pair comprise at least two molecules each of which have at least one structure complementary to a structure of the other molecule, the at least two molecules being able to bind through a binding of the complementary structures. The term molecule also includes molecule complexes such as, for example, enzymes consisting of Apo enzyme and coenzyme, proteins consisting of a plurality of subunits, lipoproteins consisting of protein and lipids, etc. Specific binding partners may be substances which occur naturally or else have been prepared for example by chemical synthesis, microbiological techniques and/or methods of genetic manipulation. Examples of specific binding partners, include but are not limited to, antibodies, antigens, haptens, enzymes, lectins, nucleic acids, repressors, oligo- and polynucleotides, protein A, protein G, avidin, streptavidin, biotin, complement component Clq, nucleic acid-binding proteins, etc. Specific binding pairs, include, but are not limited to, antibody-antigen, antibody-hapten, operator-repressor, nuclease-nucleotide, biotin-avidin, lectin-polysaccharide, steroid-steroid-binding protein, drug-drug receptor, hormone-hormone receptor, enzyme-substrate, IgG-protein A, complementary oligo- or polynucleotides, etc.

As used herein, the term “stringent conditions” refers to hybridization to filter-bound DNA in 6× sodium chloride/sodium citrate (“SSC”) at about 45° C. followed by one or more washes in 0.2×SSC/0.1% SDS at about 50-65° C. The term “under highly stringent conditions”, refers to hybridization to filter-bound nucleic acid in 6×SSC at about 45° C. followed by one or more washes in 0.1×SSC/0.2% SDS at about 68° C., or under other stringent hybridization conditions which are known to those skilled in the art (see, for example, Ausubel, F. M. et al., eds., 1989, Current Protocols in Molecular Biology, Vol. I, Green Publishing Associates, Inc. and John Wiley & Sons, Inc., New York at pages 6.3.1-6.3.6 and 2.10.3).

As used herein, the terms “subject” and “patient” are used interchangeably. As used herein, the terms “subject” and “subjects” refer to an animal, in one aspect, a bird (for example, a duck or goose), in another aspect, a shark or whale, or in a further aspect, a mammal including, a non-primate (for example, a cow, pig, camel, llama, horse, goat, rabbit, sheep, hamsters, guinea pig, cat, dog, rat, and mouse) and a primate (for example, a monkey, such as a cynomolgous monkey, chimpanzee, and a human).

As used herein, the term “test sample” refers to a component of a subject’s body which is the source of the analyte (such as antibodies of interest or antigens of interest). These components are well known in the art. For example, a test sample can be any biological sample derived from serum, plasma, whole blood, lymph, CNS fluid, urine or other bodily fluids of a subject. The test sample can be prepared using routine techniques known to those skilled in the art.

II. Antibodies of the Present Invention

The present invention provides antibodies that immunospecifically bind to at least one epitope on at least one immunosuppressive agent. More particularly, the present invention provides for antibodies that have a high binding affinity for least one immunosuppressive agent. In one aspect, the antibodies described herein immunospecifically bind to at least one epitope on at least one immunosuppressive agent and may exhibit at least a 1.1-fold improvement, at least a 2-fold improvement, at least a 3-fold improvement, at least a 4-fold improvement, at least a 5-fold improvement, at least a 6-fold improvement, at least a 7-fold improvement, at least a 8-fold improvement, at least a 9-fold improvement, at least a 10-fold improvement, at least an 11-fold improvement, at least a 12-fold improvement, at least a 13-fold improvement, at least a 14-fold improvement, at least a 15-fold improvement, at least a 16-fold improvement, at least a 17-fold improvement, at least a 18-fold improvement, at least a 19-fold improvement or at least a 20-fold improvement in their equilibrium dissociation constant ($K_D$) or disassociation rate constant ($k_d$ or $k_{off}$) when compared to the $K_D$ or $k_d$ of an antibody produced by mouse hybridoma cell line 1-60-46 (available from Astellas Pharma, Inc., Tokyo, Japan) (which is also referred to herein as the “wildtype”). The above described fold improvement in the $K_D$ or $k_d$ can be exhibited when said antibodies have not been exposed to (such as in a diagnostic immunoassay) or incubated with at least one selection diluent (such as, but not limited to, at least one solvent). Additionally, these antibodies, as immunoglobulins, bind to at least one immunosuppressive agent with a $K_D$ of less than $1.9\times10^{-11}$ M. Preferably, these antibodies bind to at least one immunosuppressive agent with a $K_D$ of between $1.89\times10^{-11}$ M and $1.0\times10^{-13}$ M. More preferably, these antibodies exhibit a $K_D$ of between $1.89\times10^{-11}$ M and $1.0\times10^{-12}$ M. Moreover, these antibodies, as scFvs, bind to at least one immunosuppressive agent with a $k_d$ of less than $1.3\times10^{-4}$/sec. Preferably, these antibodies bind to at least one immunosuppressive agent with a $k_d$ of between $1.29\times10^{-4}$/sec and $1.0\times10^{-6}$/sec. More preferably, these antibodies exhibit a $k_d$ of between $1.29\times10^{-4}$/sec and $1.0\times10^{-5}$/sec.

When the above-described antibodies are exposed to (such as, prior to or during a diagnostic immunoassay; the timing of the exposure of the antibody to the at least one selection diluent is not critical), incubated with, or are in the presence of at least one selection diluent (such as, but not limited to at least one selection diluent), then these antibodies may exhibit at least a 1.1-fold improvement, at least a 2-fold improvement, at least a 3-fold improvement, at least a 4-fold improvement, at least a 5-fold improvement, at least a 6-fold improvement, at least a 7-fold improvement, at least a 8-fold improvement, at least a 9-fold improvement, at least a 10-fold improvement, at least an 11-fold improvement, at least a 12-fold improvement, at least a 13-fold improvement, at least a 14-fold improvement, at least a 15-fold improvement, at least a 16-fold improvement, at least a 17-fold improvement, at least a 18-fold improvement, at least a 19-fold improvement or at least a 20-fold improvement in their $K_D$ or $k_d$ when compared to the $K_D$ or $k_d$ of the wildtype after exposure to or incubation of the wildtype with at least one selection diluent. Additionally, these antibodies, as immunoglobulins, bind to at least one immunosuppressive agent with a $K_D$ of less than $1.52\times10^{-10}$ M. Preferably, these antibodies bind to at least one immunosuppressive agent with a $K_D$ of between $1.51\times10^{-10}$ M and $1.0\times10^{-2}$ M. More preferably, these antibodies have a $K_D$ of between $1.51\times10^{-10}$ M and $1.0\times10^{-11}$ M. Additionally, these antibodies, as scFvs, bind to at least one immunosuppressive agent with a $k_d$ of less than $9.38\times10^{-4}$/sec. Preferably, these antibodies bind to at least one immunosuppressive agent with a $k_d$ of between $9.37\times10^{-4}$/sec and $1.0\times10^{-6}$/sec. More preferably, these antibodies exhibit a $k_d$ of between $9.37\times10^{-4}$/sec and $1.0\times10^{-5}$/sec.

In yet another aspect, the present invention provides antibodies produced by Chinese hamster ovary (hereinafter “CHO”) cell line 1-60-46 AM2 CHO 2-577 or CHO cell line 1-60-46 AM2 CHO 1-1157. Antibodies produced by each of these cell lines immunospecifically bind to at least one epitope on tacrolimus. More specifically, antibodies produced by each of these cell lines bind to at least one epitope on tacrolimus with a $K_D$ of less than $1.9\times10^{-11}$ M, when said antibodies are have not been exposed to (such as prior to or during a diagnostic immunoassay), incubated with or are in the presence of at least one selection diluent (such as, but not limited to at least one solvent). Preferably, these antibodies exhibit a $K_D$ of $1.2\times10^{-12}$ M. However, if said antibodies are exposed to (such prior to or during a diagnostic immunoassay) or incubated with at least one selection diluent, then said antibodies immunospecifically bind to at least one epitope on tacrolimus with a $K_D$ of less than $1.52\times10^{-10}$ M. Preferably, these antibodies exhibit a $K_D$ of $1.3\times10^{-11}$ M in 10% methanol Additionally, the present invention also contemplates antibodies made from nucleic acids (DNA) extracted from CHO cell line 1-60-46 AM2 CHO 2-577 or CHO cell line 1-60-46 AM2 CHO 1-1157. Furthermore, the present invention also relates to a chimeric antibody or binding fragment thereof produced by CHO cell line 1-60-46 AM2 CHO 2-577 or CHO cell line 1-60-46 AM2 CHO 1-1157.

In another aspect, the antibodies of the present invention are derivatives or variants of the antibodies produced by hybridoma cell line 1-60-46. More specifically, the inventors of the present invention have discovered that antibodies that are derivatives or variants of the antibodies produced by hybridoma cell line 1-60-46 can be produced which exhibit a high binding affinity to at least one epitope on at least one immunosuppressive agent, regardless of whether or not said antibodies are exposed to or incubated with at least one selection diluent. More specifically, the antibodies of the present invention, as immunoglobulins, bind to at least one epitope on at least one immunosuppressive agent with a $K_D$ of less than $1.9\times10^{-11}$ M, preferably with a $K_D$ ranging from $1.89\times10^{-11}$ M and $1.0\times10^{-13}$ M, and more preferably, with a $K_D$ ranging from $1.89\times10^{-11}$ M and $1.0\times10^{-12}$ M, when said antibodies are not exposed to, incubated with or are in the presence of at least one selection diluent. As scFvs, the antibodies of the present invention bind to at least one epitope on at least one immunosuppressive agent with a $k_d$ of less than $1.3\times10^{-4}$/sec, preferably with a $k_d$ ranging from $1.29\times10^{-4}$/sec and $1.0\times10^{-6}$/sec, and more preferably, with a $k_d$ ranging from $1.29\times10^{-4}$/sec and $1.0\times10^{-5}$/sec.

In contrast, when these antibodies are exposed to, incubated with, or are in the presence of at least one selection diluent, these antibodies, as immunoglobulins, bind to at least one epitope on at least one immunosuppressive agent with a $K_D$ of less than $1.52\times10^{-10}$ M, preferably with a $K_D$ ranging from $1.51\times10^{-10}$ M and $1.0\times10^{-11}$ M, and more preferably with a $K_D$ ranging from $1.51\times10^{-10}$ M and $1.0\times10^{-11}$ M. As scFvs, these the antibodies of the present invention bind to at least one epitope on at least one immunosuppressive agent with a $k_d$ of less than $9.38\times10^{-4}$/sec, preferably with a $k_d$ ranging from $9.37\times10^{-4}$/sec and $1.0\times10^{-6}$/sec, and more preferably with a $k_d$ ranging from $9.37\times10^{-4}$/sec and $1.0\times10^{-5}$/sec. The derived or variant antibodies of the present invention may comprise at least one mutation (such as at least one deletion, addition, substitution or any combinations thereof) in at least one of the heavy chain complementary determining ("CDR") regions (for example, the heavy chain CDR 1, heavy chain CDR 2 and/or heavy chain CDR 3), at least one mutation (such as at least one deletion, addition, substitution or any combinations thereof) in the light chain CDR regions (for example, the light chain CDR 1, light chain CDR 2, and/or light chain CDR 3) or at least one mutation (such as at least one deletion, addition, substitution or any combinations thereof) in at least one of the heavy chain CDR regions and at least one mutation in at least one of the light chain CDR regions when compared to the amino acid sequence of the antibody produced by the wildtype. Moreover, the antibodies of the present invention may also contain one or more other mutations (such as at least one deletion, addition, substitution or any combinations thereof) in a part or portion of the antibody other than the CDR, such as, but not limited to, the framework region ("FR") of an antibody. Methods for creating such derivatives are well known in the art and include the use of site-directed mutagenesis and PCR-mediated mutagenesis, which will be discussed in more detail infra.

More specifically, in another aspect, the antibody of the present invention specifically binds to at least one epitope on at least one immunosuppressive agent and comprises a heavy chain CDR 2 having an amino acid sequence of the formula of: Thr-Ile-Ser-Ser-Gly-Gly-$Xaa_1$-$Xaa_2$-$Xaa_3$-Phe (SEQ ID NO: 33)

wherein $Xaa_1$ is selected from the group consisting of threonine (Thr), alanine (Ala), lysine (Lys) and glutamic acid (Glu);

wherein $Xaa_2$ is selected from the group consisting of tyrosine (Tyr) and tryptophan (Trp); and wherein $Xaa_3$ is selected from the group consisting of threonine (Thr) and valine (Val);

provided that $Xaa_1$ is other than threonine (Thr) when $Xaa_2$ is tyrosine (Tyr) and $Xaa_3$ is threonine (Thr).

In yet a further aspect, the antibody of the present invention specifically binds to at least one epitope of at least one immunosuppressive agent and comprises a heavy chain CDR 2 having the amino acid sequence shown in SEQ ID NOS:15, 16, 17 or 18. In another aspect, the present invention relates to an antibody that specifically binds to at least one epitope on at least one immunosuppressive agent and that comprises an amino acid sequence that is at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to an amino acid sequence of SEQ ID NOS:15, 16, 17 or 18.

In yet another aspect, the antibody of the present invention specifically binds to at least one epitope on at least one immunosuppressive agent and comprises a light chain CDR 1 that has an amino acid sequence having a formula of: Lys-Ser-Ser-$Xaa_4$-$Xaa_5$-$Xaa_6$-Val-His-Ser-Thr-Gly-Asn-Thr-Phe-Leu-Glu (SEQ ID NO:34)

wherein $Xaa_4$ is selected from the group consisting of: glutamine (Gln), alanine (Ala) and glycine (Gly);

wherein $Xaa_5$ is selected from the group consisting of: serine (Ser) and glycine (Gly); and wherein $Xaa_6$ is selected from the group consisting of: isoleucine (Ile) and leucine (Leu);

provided that $Xaa_4$ is other than glutamine (Gln) when $Xaa_5$ is serine (Ser) and $Xaa_6$ is isoleucine (Ile).

In yet a further aspect, the antibody specifically binds to at least one epitope on at least one immunosuppressive agent and has a light chain CDR 1 having the amino acid sequence of SEQ ID NOS:19, 20, 21 or 22. In another aspect, the present invention relates to an antibody that specifically binds to at least one epitope on at least one immunosuppressive agent and that comprises an amino acid sequence that is at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to an amino acid sequence of SEQ ID NOS:19, 20, 21 or 22.

In yet another aspect, the antibody of the present invention specifically binds to at least one epitope on at least one immunosuppressive agent and comprises a light chain CDR 3 that has an amino acid sequence having a formula of: Phe-Gln-Gly-$Xaa_7$-$Xaa_8$-$Xaa_9$-Pro-Leu-Thr (SEQ ID NO:35), wherein $Xaa_7$ is selected from the group consisting of: serine (Ser) and glycine (Gly);

wherein $Xaa_8$ is selected from the group consisting of: histidine (His), arginine (Arg), valine (Val), threonine (Thr), lysine (Lys) and serine (Ser); and wherein $Xaa_9$ is selected from the group consisting of: valine (Val), alanine (Ala), aspartic acid (Asp), cysteine (Cys) and serine (Ser);

provided that $Xaa_7$ is other than serine (Ser) when $Xaa_8$ is histidine (His) and $Xaa_9$ is valine (Val).

In yet a further aspect, the antibody specifically binds to at least one epitope on at least one immunosuppressive agent and has a light chain CDR 3 having the amino acid sequence of SEQ ID NOS: 23, 24, 25, 26, 27, 28, 29, 30, 31 or 32. In another aspect, the present invention relates to an antibody that specifically binds to at least one epitope on at least one immunosuppressive agent that comprises an amino acid sequence that is at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to an amino acid sequence of SEQ ID NOS: 23, 24, 25, 26, 27, 28, 29, 30, 31 or 32.

In yet a further aspect, the antibody of the present invention specifically binds to at least one epitope on at least one immunosuppressive agent and has a heavy chain CDR 1, heavy chain CDR 2, heavy chain CDR 3, a light chain CDR 1, a light chain CDR 2 and a light variable CDR 3 comprising the following amino acid sequences:

(a) Heavy Chain CDR 1 has an amino acid sequence of: Gly-Phe-Thr-Phe-Ser-Ser-Tyr-Gly-Met-Ser (SEQ ID NO:2);

(b) Heavy Chain CDR 2 has an amino acid sequence having a formula of: Thr-Ile-Ser-Ser-Gly-Gly-$Xaa_1$-$Xaa_2$-$Xaa_3$-Phe (SEQ ID NO:33)

wherein $Xaa_1$ is selected from the group consisting of threonine (Thr), alanine (Ala), lysine (Lys) and glutamic acid (Glu);

wherein $Xaa_2$ is selected from the group consisting of tyrosine (Tyr) and tryptophan (Trp); and wherein $Xaa_3$ is selected from the group consisting of threonine (Thr) and valine (Val);

(c) Heavy Chain CDR 3 has an amino acid sequence of: Gln-Thr-Asp-Gly-Tyr-Ser-Trp-Phe-Pro-Tyr (SEQ ID NO:6);

(d) Light Chain CDR 1 has an amino acid sequence having a formula of: Lys-Ser-Ser-$Xaa_4$-$Xaa_5$-$Xaa_6$-Val-His-Ser-Thr-Gly-Asn-Thr-Phe-Leu-Glu (SEQ ID NO:34)

wherein $Xaa_4$ is selected from the group consisting of: glutamine (Gln), alanine (Ala) and glycine (Gly);

wherein $Xaa_5$ is selected from the group consisting of: serine (Ser) and glycine (Gly); and wherein $Xaa_6$ is selected from the group consisting of: isoleucine (Ile) and leucine (Leu);

(e) Light Chain CDR 2 has an amino acid sequence having the formula of: Lys-Ile-Ser-Asn-Arg-Phe-Ser (SEQ ID NO:11)

(f) Light Chain CDR 3 has an amino acid sequence having a formula of: Phe-Gln-Gly-$Xaa_7$-$Xaa_8$-$Xaa_9$-Pro-Leu-Thr (SEQ ID NO:35), wherein $Xaa_7$ is selected from the group consisting of: Serine (Ser) and Glycine (Gly);

wherein $Xaa_8$ is selected from the group consisting of: histidine (His), arginine (Arg), valine (Val), threonine (Thr), lysine (Lys) and serine (Ser); and wherein $Xaa_9$ is selected from the group consisting of: valine (Val), alanine (Ala), aspartic acid (Asp), cysteine (Cys) and Serine (Ser);

with the proviso that if in heavy chain CDR 2 $Xaa_1$ is Thr, $Xaa_2$ is Tyr and $Xaa_3$ is Thr and in the light chain CDR $Xaa_4$ is Gln, $Xaa_5$ is Ser and $Xaa_6$ is Ile, then in light chain CDR 3 $Xaa_9$ is other than Val if $Xaa_7$ is Ser and $Xaa_8$ is His, or $Xaa_8$ is other than His if $Xaa_7$ is Ser and $Xaa_9$ is Val or $Xaa_7$ is other than Ser if $Xaa_8$ is His and $Xaa_9$ is Val.

Preferably, the antibodies having the above-described formulas comprise a heavy chain CDR 1, heavy chain CDR 2, heavy chain CDR 3, light chain CDR 1, light chain CDR 2 and light chain CDR 3 where $Xaa_1$-$Xaa_8$ in the above described formulas have the amino acid residues shown below in Table A:

TABLE A

| $Xaa_1$ | $Xaa_2$ | $Xaa_3$ | $Xaa_4$ | $Xaa_5$ | $Xaa_6$ | $Xaa_7$ | $Xaa_8$ | $Xaa_9$ | SEQ ID NO. |
|---|---|---|---|---|---|---|---|---|---|
| Thr | Trp | Thr | Gln | Ser | Ile | Ser | His | Val | 63 |
| Ala | Trp | Thr | Gln | Ser | Ile | Ser | His | Val | 64 |
| Lys | Trp | Val | Gln | Ser | Ile | Ser | His | Val | 65 |
| Glu | Trp | Thr | Gln | Ser | Ile | Ser | His | Val | 66 |
| Thr | Tyr | Thr | Gln | Gly | Ile | Ser | His | Val | 67 |
| Thr | Tyr | Thr | Ala | Gly | Ile | Ser | His | Val | 68 |
| Thr | Tyr | Thr | Gly | Gly | Leu | Ser | His | Val | 69 |
| Thr | Tyr | Thr | Gln | Gly | Leu | Ser | His | Val | 70 |
| Thr | Tyr | Thr | Gln | Ser | Ile | Ser | His | Ala | 71 |
| Thr | Tyr | Thr | Gln | Ser | Ile | Ser | Arg | Ala | 72 |
| Thr | Tyr | Thr | Gln | Ser | Ile | Ser | His | Asp | 73 |
| Thr | Tyr | Thr | Gln | Ser | Ile | Ser | His | Cys | 74 |
| Thr | Tyr | Thr | Gln | Ser | Ile | Ser | His | Ser | 75 |
| Thr | Tyr | Thr | Gln | Ser | Ile | Gly | Arg | Cys | 76 |
| Thr | Tyr | Thr | Gln | Ser | Ile | Gly | Val | Cys | 77 |
| Thr | Tyr | Thr | Gln | Ser | Ile | Ser | Thr | Cys | 78 |
| Thr | Tyr | Thr | Gln | Ser | Ile | Ser | Lys | Cys | 79 |
| Thr | Tyr | Thr | Gln | Ser | Ile | Ser | Ser | Ser | 80 |
| Ala | Trp | Thr | Gln | Gly | Leu | Ser | Ser | Ser | 81 |
| Ala | Trp | Thr | Gln | Gly | Leu | Ser | His | Ala | 82 |
| Ala | Trp | Thr | Gln | Ser | Ile | Gly | Arg | Cys | 83 |
| Ala | Trp | Thr | Gln | Ser | Ile | Ser | Ser | Ser | 84 |
| Ala | Trp | Thr | Gln | Gly | Leu | Gly | Arg | Cys | 85 |
| Thr | Tyr | Thr | Gln | Gly | Leu | Gly | Arg | Cys | 86 |
| Thr | Tyr | Thr | Gln | Gly | Leu | Ser | Ser | Ser | 87 |
| Lys | Trp | Val | Gln | Gly | Leu | Ser | His | Ser | 88 |
| Glu | Trp | Thr | Gln | Gly | Leu | Ser | His | Ser | 89 |
| Glu | Trp | Thr | Gln | Ser | Ile | Gly | Val | Cys | 90 |
| Glu | Trp | Thr | Gly | Gly | Leu | Ser | His | Ser | 91 |
| Ala | Trp | Thr | Gln | Gly | Leu | Ser | His | Ser | 92 |

III. Nucleic Acid Molecules

The present invention provides for one or more nucleic acid molecules, generally isolated, encoding an antibody of the present invention that specifically binds to at least one epitope on at least one immunosuppressive agent. In one aspect, the invention provides an isolated nucleic acid molecule encoding an antibody that binds to at least one epitope on at least one immunosuppressive agent and that may exhibit at least a 1.1-fold improvement, at least a 2-fold improvement, at least a 3-fold improvement, at least a 4-fold improvement, at least a 5-fold improvement, at least a 6-fold improvement, at least a 7-fold improvement, at least a 8-fold improvement, at least a 9-fold improvement, at least a 10-fold improvement, at least an 11-fold improvement, at least a 12-fold improvement, at least a 13-fold improvement, at least a 14-fold improvement, at least a 15-fold improvement, at least a 16-fold improvement, at least a 17-fold improvement, at least a 18-fold improvement, at least a 19-fold improvement or at least a 20-fold improvement in its $K_D$ or $k_d$ when compared with an antibody produced by the wildtype. The present invention also provides an isolated nucleic acid molecule that comprises a polynucleotide sequence that hybridizes, under stringent conditions, to the nucleic acid molecule described herein. The above described fold improvement in the $K_D$ or $k_d$ may be exhibited when said antibodies have not been exposed to (such as prior to or during a diagnostic immunoassay) or incubated with at least one selection diluent (such as, but not limited to, at least one solvent).

In another aspect, the invention provides an isolated nucleic acid molecule encoding an antibody that binds to at least one epitope on at least one immunosuppressive agent with at least one immunosuppressive agent and may exhibit at least a 1.1-fold improvement, at least a 2-fold improvement, at least a 3-fold improvement, at least a 4-fold improvement, at least a 5-fold improvement, at least a 6-fold improvement, at least a 7-fold improvement, at least a 8-fold improvement, at least a 9-fold improvement, at least a 10-fold improvement, at least an 11-fold improvement, at least a 12-fold improvement, at least a 13-fold improvement, at least a 14-fold improvement, at least a 15-fold improvement, at least a 16-fold improvement, at least a 17-fold improvement, at least a 18-fold improvement, at least a 19-fold improvement or at least a 20-fold improvement, in its $K_D$ or $k_d$ when compared with an antibody produced by the "wildtype". The present invention also provides an isolated nucleic acid molecule that comprises a polynucleotide sequence that hybridizes, under stringent conditions, to the nucleic acid molecule described herein. The above described fold improvement in the equilibrium dissociation constant may be exhibited when said antibodies have been or are exposed to (such as prior to or during a diagnostic immunoassay) or incubated with at least one selection diluent (such as, but not limited to, at least one solvent).

In yet still another aspect, the invention provides an isolated nucleic acid molecule encoding an antibody that, as an immunoglobulin, specifically binds to at least one epitope on at least one immunosuppressive agent and that has a $K_D$ of at less than $1.9\times10^{-11}$ M, preferably, a $K_D$ between $1.89\times10^{-11}$ M and $1.0\times10^{-13}$ M and more preferably, a $K_D$ between $1.89\times10^{-1}$ M and $1.0\times10^{-12}$ M. The present invention further provides an isolated nucleic acid molecule encoding an antibody that, as an scFv, specifically binds to at least one epitope on at least one immunosuppressive agent and that has a $k_d$ of less than $1.3\times10^{-4}$/sec, preferably with a $k_d$ ranging from $1.29\times10^{-4}$/sec and $1.0\times10^{-6}$/sec, and more preferably, with a $k_d$ ranging from $1.29\times10^{-4}$/sec and $1.0\times10^{-5}$/sec. The present invention also provides an isolated nucleic acid molecule that comprises a polynucleotide sequence that hybridizes, under stringent conditions, to the nucleic acid molecules described herein. The above described $K_D$ or $k_d$ values are exhibited when said antibodies have not been exposed to (such as in a diagnostic immunoassay), incubated with or are in the presence of at least one selection diluent (such as, but not limited to, at least one solvent).

In yet still another aspect, the invention provides an isolated nucleic acid molecule encoding an antibody that, as an immunoglobulin, specifically binds to at least one epitope on at least one immunosuppressive agent and that has a $K_D$ of at less than $1.52\times10^{-10}$ M, preferably, a $K_D$ between $1.51\times10^{-10}$ M and $1.0\times10^{-12}$ M, and more preferably, a $K_D$ between $1.51\times10^{-10}$ M and $1.0\times10^{-11}$ M. The present invention further provides an isolated nucleic acid molecule encoding an antibody that, as an scFv, specifically binds to at least one epitope on at least one immunosuppressive agent and that has a $k_d$ of less than $9.38\times10^{-4}$/sec, preferably with a $k_d$ ranging from $9.37\times10^{-4}$/sec and $1.0\times10^{-6}$/sec, and more preferably with a $k_d$ ranging from $9.37\times10^{-4}$/sec and $1.0\times10^{-5}$/sec. The present invention also provides an isolated nucleic acid molecule that comprises a polynucleotide sequence that hybridizes, under stringent conditions, to the nucleic acid molecules described herein. The above described $K_D$ or $k_d$ values are exhibited when said antibodies have been or are exposed to (such as in a diagnostic immunoassay), incubated with or are in the presence of at least one selection diluent (such as, but not limited to, at least one solvent).

In yet another aspect, the invention provides an isolated nucleic acid molecule encoding an antibody that specifically binds to at least one epitope on at least one immunosuppressive agent, wherein said nucleic acid molecule comprises the polynucleotide sequence of antibody produced by CHO cell 1-60-46 AM2 CHO 2-577 or CHO cell line 1-60-46 AM2 CHO 1-1157. The present invention also provides an isolated nucleic acid molecule that comprises a polynucleotide sequence that hybridizes, under stringent conditions, to the nucleic acid molecule described herein.

In another aspect, the present invention provides an isolated nucleic acid molecule that encodes antibodies that immunospecifically bind to at least one epitope on at least one immunosuppressive agent, wherein said antibodies comprise derivatives or variants of antibodies produced by mouse hybridoma cell line 1-60-46. As discussed previously herein, the inventors of the present invention have discovered that antibodies that are derivatives or variants of the antibodies produced by mouse hybridoma cell line 1-60-46 may be produced which exhibit a high binding affinity, specifically, as immunoglobulins, with a $K_D$ of less than $1.9\times10^{-11}$ M, preferably, a $K_D$ ranging from $1.89\times10^{-11}$ M to $1.0\times10^{-13}$ M, and more preferably, a $K_D$ ranging from $1.89\times10^{-11}$ M to $1.0\times10^{-12}$ M or as scFvs, with a $k_d$ of less than $1.3\times10^{-4}$/sec, preferably with a $k_d$ ranging from $1.29\times10^{-4}$/sec and $1.0\times10^{-6}$/sec, and more preferably, with a $k_d$ ranging from $1.29\times10^{-4}$/sec and $1.0\times10^{-5}$/sec, when said antibodies are not exposed to, incubated with or are in the presence of at least one selection diluent. In contrast, when these antibodies are exposed to, incubated with, or are in the presence of at least one selection diluent, these antibodies bind to at least one epitope on at least one immunosuppressive agent, as immunoglobulins, with a $K_D$ of less than $1.52\times10^{-10}$ M, preferably, a $K_D$ ranging from $1.51\times10^{-10}$ M to $1.0\times10^{-12}$ M, and, more preferably, a $K_D$ ranging from $1.51\times10^{-10}$ M to $1.0\times10^{-11}$ M or as scFvs, with a $k_d$ of less than $9.38\times10^{-4}$/sec, preferably with a $k_d$ ranging from $9.37\times10^{-4}$/sec and $1.0\times10^{-6}$/sec, and more preferably with a $k_d$ ranging from $9.37\times10^{-4}$/sec and $1.0\times10^{-5}$/sec.

The derived or variant antibodies of the present invention comprises at least one mutation (such as at least one deletion, addition, substitution or any combinations thereof) in at least one of the heavy chain CDR regions (for example, the heavy chain CDR 1, heavy chain CDR 2, or heavy chain CDR 3), at least one mutation (such as at least one deletion, addition, substitution or any combinations thereof) in the light chain CDR regions (for example, the light chain CDR 1, light chain CDR 2, or light chain CDR 3) or at least one mutation in at least one of the heavy chain CDR regions and at least one mutation in at least one of the light chain CDR regions when compared to the amino acid sequence the antibody produced by the wildtype. Standard techniques known to those of skill in the art can be used to introduce mutations (such as at least one deletion, addition, substitution or any combinations thereof) in the nucleic acid molecule encoding an antibody of the present invention, including, for example, site-directed mutagenesis and PCR-mediated mutagenesis which results in amino acid substitutions. In one aspect, the derivatives include less than 15 amino acid substitutions or less than 10 amino acid substitutions or less than 7 amino acid substitutions relative to the original antibody produced by the wildtype. In one aspect, the derivatives have conservative amino acid substitutions are made at one or more predicted nonessential amino acid residues (i.e., amino acid residues which are not critical for the antibody to immunospecifically bind to at least one epitope on at least one immunosuppressive agent). A "conservative amino acid substitution" is one in which the amino acid residue is replaced with the amino acid residue having a side chain with a similar charge. Families of amino acid residues having side chains with similar charges have been defined in the art. These families include amino acids with basic side chains (for example, lysine, arginine, histidine), acidic side chains (for example, aspartic acid, glutamic acid), uncharged polar side chains (for example, glycine, asparagine, glutamine, serine, threonine, tyrosine, cysteine), nonpolar side chains (for example, alanine, valine, leucine, isoleucine, proline, phenylalanine, methionine, tryptophan), beta-branched side chains (for example, threonine, valine, isoleucine) and aromatic side chains (for example, tyrosine, phenylalanine, tryptophan, histidine). Alternatively, mutations can be introduced randomly along all or part of the coding sequence, such as by saturation mutagenesis, and the resultant mutants can be screened for biological activity to identify mutants that exhibit enhanced binding affinity to at least one epitope on at least one immunosuppressive agent. Following mutagenesis, the encoded antibody can be expressed and the activity of the antibody can be determined.

In another aspect, the present invention provides an isolated nucleic acid molecule encoding an antibody that specifically binds to at least one epitope on at least one immunosuppressive agent, said antibody having a heavy chain CDR 2 having an amino acid sequence of the formula of:

a heavy chain CDR 2 having an amino acid sequence of the formula of: Thr-Ile-Ser-Ser-Gly-Gly-$Xaa_1$-$Xaa_2$-$Xaa_3$-Phe (SEQ ID NO:33)

wherein $Xaa_1$ is selected from the group consisting of threonine (Thr), alanine (Ala), lysine (Lys) and glutamic acid (Glu);

wherein $Xaa_2$ is selected from the group consisting of tyrosine (Tyr) and tryptophan (Trp); and wherein $Xaa_3$ is selected from the group consisting of threonine (Thr) and valine (Val);

provided that $Xaa_1$ is other than threonine (Thr) when $Xaa_2$ is tyrosine (Tyr) and $Xaa_3$ is threonine (Thr).

The present invention also provides an isolated nucleic acid molecule that comprises a polynucleotide sequence that hybridizes, under stringent conditions, to the nucleic acid molecule described herein that encodes an antibody having a heavy chain CDR 2 having an amino acid sequence described above.

In another aspect, the invention provides an isolated nucleic acid molecule encoding an antibody that specifically binds to at least one epitope on at least one immunosuppressive agent, said antibody comprising (alternatively, consisting of) a heavy chain CDR 2 having an amino acid sequence of SEQ ID NOS:15, 16, 17 or 18. The present invention also provides an isolated nucleic acid molecule that comprises a polynucleotide sequence that hybridizes, under stringent conditions, to the nucleic acid molecule described herein that encodes an antibody comprising a heavy chain CDR 2 having the amino acid sequence of SEQ ID NOS:15, 16, 17 or 18.

In another aspect, the present invention provides an isolated nucleic acid molecule encoding an antibody that specifically binds to at least one epitope on at least one immunosuppressive agent, said antibody having a light chain CDR 1 that has an amino acid sequence having a formula of: Lys-Ser-Ser-$Xaa_4$-$Xaa_5$-$Xaa_6$-Val-His-Ser-Thr-Gly-Asn-Thr-Phe-Leu-Glu (SEQ ID NO:34)

wherein $Xaa_4$ is selected from the group consisting of: glutamine (Gln), alanine (Ala) and glycine (Gly);

wherein $Xaa_5$ is selected from the group consisting of: serine (Ser) and glycine (Gly); and wherein $Xaa_6$ is selected from the group consisting of: isoleucine (Ile) and leucine (Leu);

provided that $Xaa_4$ is other than glutamine (Gln) when $Xaa_5$ is serine (Ser) and $Xaa_6$ is isoleucine (Ile).

The present invention also provides an isolated nucleic acid molecule that comprises a polynucleotide sequence that hybridizes, under stringent conditions, to the nucleic acid molecule described herein that encodes an antibody having a light chain CDR 1 having an amino acid sequence described above.

In another aspect, the invention provides an isolated nucleic acid molecule encoding an antibody that specifically binds to at least one epitope on at least one immunosuppressive agent, said antibody comprising (alternatively, consisting of) a light chain CDR 1 having an amino acid sequence of SEQ ID NOS:19, 20, 21 or 22. The present invention also provides an isolated nucleic acid molecule that comprises a polynucleotide sequence that hybridizes, under stringent conditions, to the nucleic acid molecule described herein that encodes an antibody comprising a light chain CDR 1 having the amino acid sequence of SEQ ID NOS:19, 20, 21 or 22.

In another aspect, the present invention provides an isolated nucleic acid molecule encoding an antibody that specifically binds to at least one epitope on at least one immunosuppressive agent, said antibody having a light chain CDR 3 that has an amino acid sequence having a formula of: Phe-Gln-Gly-$Xaa_7$-$Xaa_8$-$Xaa_9$-Pro-Leu-Thr (SEQ ID NO:35), wherein $Xaa_7$ is selected from the group consisting of: serine (Ser) and glycine (Gly);

wherein $Xaa_8$ is selected from the group consisting of: histidine (His), arginine (Arg), valine (Val), threonine (Thr), lysine (Lys) and serine (Ser); and wherein $Xaa_9$ is selected from the group consisting of: valine (Val), alanine (Ala), aspartic acid (Asp), cysteine (Cys) and serine (Ser);

provided that $Xaa_7$ is other than serine (Ser) when $Xaa_8$ is histidine (His) and $Xaa_9$ is valine (Val).

The present invention also provides an isolated nucleic acid molecule that comprises a polynucleotide sequence that hybridizes, under stringent conditions, to the nucleic acid molecule described herein that encodes an antibody having a light chain CDR 3 having an amino acid sequence described above.

In another aspect, the invention provides an isolated nucleic acid molecule encoding an antibody that specifically binds to at least one epitope on at least one immunosuppressive agent, said antibody comprising (alternatively, consisting of) a light chain CDR 3 having an amino acid sequence of SEQ ID NOS:23, 24, 25, 26, 27, 28, 29, 30, 31 or 32. The present invention also provides an isolated nucleic acid molecule that comprises a polynucleotide sequence that hybridizes, under stringent conditions, to the nucleic acid molecule described herein that encodes an antibody comprising a light chain CDR 3 having the amino acid sequence of SEQ ID NOS:23, 24, 25, 26, 27, 28, 29, 30, 31 or 32.

In another aspect, the invention provides an isolated nucleic acid molecule that encodes an antibody that specifically binds to at least one epitope on at least one immunosuppressive agent, said antibody comprising (alternatively, consisting) a heavy chain CDR 2 having an amino acid sequence of SEQ ID NOS:15, 16, 17 or 18, a light chain CDR 1 having an amino acid sequence of SEQ ID NOS:19, 20, 21 or 22, a light chain CDR 3 having an amino acid sequence of SEQ ID NOS:23, 24, 25, 26, 27, 28, 29, 30, 31 or 32 or any combinations these amino acid sequences. The present invention also provides an isolated nucleic acid molecule that comprises a polynucleotide sequence that hybridizes, under stringent conditions, to the nucleic acid molecule described herein that encodes an antibody comprising a heavy chain CDR 2 having an amino acid sequence of SEQ ID NOS:15, 16, 17 or 18, a light chain CDR 1 having an amino acid sequence of SEQ ID NOS:19, 20, 21 or 22, a light chain CDR 3 having an amino acid sequence of SEQ ID NOS:23, 24, 25, 26, 27, 28, 29, 30, 31 or 32 or any combinations these amino acid sequences.

In another aspect, the present invention provides an isolated nucleic acid molecule encoding an antibody that specifically binds to at least one epitope on at least one immunosuppressive agent, said antibody having a heavy chain CDR 1, heavy chain CDR 2, heavy chain CDR 3, a light chain CDR 1, a light chain CDR 2 and a light variable CDR 3 comprising the following amino acid sequences:

(a) Heavy Chain CDR 1 has an amino acid sequence of: Gly-Phe-Thr-Phe-Ser-Ser-Tyr-Gly-Met-Ser (SEQ ID NO:2);

(b) Heavy Chain CDR 2 has an amino acid sequence having a formula of: Thr-Ile-Ser-Ser-Gly-Gly-$Xaa_1$-$Xaa_2$-$Xaa_3$-Phe (SEQ ID NO:33)

wherein $Xaa_1$ is selected from the group consisting of threonine (Thr), alanine (Ala), lysine (Lys) and glutamic acid (Glu);

wherein $Xaa_2$ is selected from the group consisting of tyrosine (Tyr) and tryptophan (Trp); and wherein $Xaa_3$ is selected from the group consisting of threonine (Thr) and valine (Val);

(c) Heavy Chain CDR 3 has an amino acid sequence of: Gln-Thr-Asp-Gly-Tyr-Ser-Trp-Phe-Pro-Tyr (SEQ ID NO:6);

(d) Light Chain CDR 1 has an amino acid sequence having a formula of: Lys-Ser-Ser-$Xaa_4$-$Xaa_5$-$Xaa_6$-Val-His-Ser-Thr-Gly-Asn-Thr-Phe-Leu-Glu (SEQ ID NO:34)

wherein $Xaa_4$ is selected from the group consisting of: glutamine (Gln), alanine (Ala) and glycine (Gly);

wherein $Xaa_5$ is selected from the group consisting of: serine (Ser) and glycine (Gly); and wherein $Xaa_6$ is selected from the group consisting of: isoleucine (Ile) and leucine (Leu);

(e) Light Chain CDR 2 has an amino acid sequence having the formula of: Lys-Ile-Ser-Asn-Arg-Phe-Ser (SEQ ID NO:11)

(f) Light Chain CDR 3 has an amino acid sequence having a formula of: Phe-Gln-Gly-$Xaa_7$-$Xaa_8$-$Xaa_9$-Pro-Leu-Thr (SEQ ID NO:35), wherein $Xaa_7$ is selected from the group consisting of: Serine (Ser) and Glycine (Gly);

wherein $Xaa_8$ is selected from the group consisting of: histidine (His), arginine (Arg), valine (Val), threonine (Thr), lysine (Lys) and serine (Ser); and wherein $Xaa_9$ is selected from the group consisting of: valine (Val), alanine (Ala), aspartic acid (Asp), cysteine (Cys) and Serine (Ser);

with the proviso that if in heavy chain CDR 2 $Xaa_1$ is Thr, $Xaa_2$ is Tyr and $Xaa_3$ is Thr and in the light chain CDR $Xaa_4$ is Gln, $Xaa_5$ is Ser and $Xaa_6$ is Ile, then in light chain CDR 3 $Xaa_9$ is other than Val if $Xaa_7$ is Ser and $Xaa_8$ is His, or $Xaa_8$ is other than His if $Xaa_7$ is Ser and $Xaa_9$ is Val or $Xaa_7$ is other than Ser if $Xaa_8$ is His and $Xaa_9$ is Val.

The present invention also provides an isolated nucleic acid molecule that comprises a polynucleotide sequence that hybridizes, under stringent conditions, to the nucleic acid molecule described herein that encodes an antibody having a heavy chain CDR 1 region, a heavy chain CDR 2 region, a heavy chain CDR 3 region, a light chain CDR 1 region, a light chain CDR 2 region and a light chain CDR 3 region having the amino acid sequences described above.

Additionally, the present invention also provides an isolated nucleic acid molecule encoding an antibody that specifically binds to at least one epitope on at least one immunosuppressive agent wherein said antibodies comprises a heavy chain CDR 1, a heavy chain CDR 2, a heavy chain CDR 3, a light chain CDR 1, a light chain CDR 2 and a light chain CDR 3 having the sequences described above and where $Xaa_1$-$Xaa_8$ have the amino acid residues shown in Table A which was previously described herein. The present invention also provides an isolated nucleic acid molecule that comprises a polynucleotide sequence that hybridizes, under stringent conditions, to the nucleic acid molecule described herein wherein that encodes an antibody having a heavy chain CDR 1 region, a heavy chain CDR 2 region, a heavy chain CDR 3 region, a light chain CDR 1 region, a light chain CDR 2 region and a light chain CDR 3 region having the amino acid sequences described above and where $Xaa_1$-$Xaa_8$ have the amino acid residues shown in Table A.

In yet still another aspect, the present invention provides an isolated nucleic acid molecule encoding an antibody that specifically binds to at least one epitope on at least one immunosuppressive agent, wherein said antibody is produced by CHO cell line 1-60-46 AM2 CHO 2-577 or CHO cell line 1-60-46 AM2 CHO 1-1157. The present invention also provides an isolated nucleic acid molecule that comprises a polynucleotide sequence that hybridizes, under stringent conditions, to the nucleic acid molecule that encodes an antibody that specifically binds to at least one epitope on at least one immunosuppressive agent, wherein said antibody is produced by CHO cell line 1-60-46 M2 CHO 2-577 or CHO cell line 1-60-46 AM2 CHO 1-1157.

IV. Methods for Preparing the Antibodies of the Present Invention

The antibodies of the present invention can be prepared using routine techniques known to those skilled in the art.

In one aspect, the antibodies of the present invention can be prepared by recombinant expression of immunoglobulin light and heavy chain genes in a host cell. To express an antibody recombinantly, a host cell is transfected with one or more recombinant expression vectors carrying nucleic acid molecules encoding the immunoglobulin light and heavy chains of the antibody such that the light and heavy chains are expressed in the host cell and, preferably, secreted into the medium in which the host cells are cultures, from which medium the antibodies can be recovered. Standard recombinant nucleic acid (DNA) methodologies are used to obtain antibody heavy and light chain genes, incorporate these genes into recombinant expressions vectors and introduce the vectors into host cells, such as those described in Sambrook, Fritsch and Maniatis (eds), *Molecular Cloning: A Laboratory Manual, Second Edition*, Cold Spring Harbor, N.Y., (1989), Ausubel, F. M. et al. (eds.) *Current Protocols in Molecular Biology*, Greene Publishing Associates (1989) and in U.S. Pat. No. 4,816,397.

To express the antibodies of the invention, nucleic acid molecules encoding the light and heavy chain regions are first obtained. These nucleic acid molecules may be obtained from the mouse hybridoma cell line expressing antibody 1-60-46 and modified by means well known in the art (such as site-directed mutagenesis) to generate antibodies of the present invention, including, for example, the antibodies produced by CHO cell line 1-60-46 AM2 CHO 2-577 or CHO cell line 1-60-46 AM2 CHO 1-1157. A mouse hybridoma cell line expressing antibody 1-60-46 is available from Astellas Pharma, Inc., Tokyo, Japan. The nucleic acid sequences of the VH and VL genes of antibody 1-60-46 are shown in FIG. 2 and SEQ ID NOS:43 and 45.

For example, once the 1-60-46 variable heavy (VH) and variable (VL) nucleic acid fragments are obtained, these sequences or specific regions within these sequences, such as the CDRs, can be mutated to encode the AM2 or AM2-related (See FIGS. 6-7 and 10) amino acid sequences disclosed herein. The amino acid sequences encoded by the 1-60-46 VH and VL DNA sequences are compared to the AM2 or AM2-related sequences to identify amino acid residues in the AM2-related sequences that differ. The appropriate nucleotides of antibody 1-60-46 are mutated such that the mutated sequence encodes the AM2 or AM2-related amino acid sequence, using the genetic code to determine which nucleotide changes should be made. Mutagenesis of 1-60-46 sequences can be carried out by standard methods, such as PCR-mediated mutagenesis (in which the mutated nucleic acids are incorporated into the PCR primers such that the PCR product contains the mutations) or site-directed mutagenesis.

Alternatively, in another aspect, nucleic acid molecules encoding the VH and VL chains can be synthesized on a chemical synthesizer, using routine techniques known to those in the art. For example, the VH and VL chains from the nucleic acid molecules described in Section III can be chemically synthesized using routine techniques known in the art. Starting at the 3' terminal base which is attached to a support, nucleotides are coupled in a step-wise fashion. Following the addition of the most 5' nucleotide, the nucleotide is cleaved from the solid support and purified by desalting followed by polyacrylamide gel electrophoresis (hereinafter "PAGE") (Midland Certified Reagents, Midland, Tex.).

Once nucleic acid fragments encoding AM2 or AM2-related VH and VL segments are obtained (by amplification and mutagenesis of VH and VL genes, as described above), these nucleic acid fragments can be further manipulated by standard recombinant DNA techniques, for example to convert the variable region genes to an antibody (such as, but not limited to, a full-length antibody chain genes, to Fab fragment genes or to a scFv gene). In these manipulations, a VL- or VH-encoding nucleic acid fragment is operatively linked to another nucleic acid fragment encoding another protein, such as antibody constant region or a flexible linker. The term "operatively linked", as used in this context, is intended to mean that the two nucleic acid fragments are joined such that the amino acid sequences encoded by the two nucleic acid fragments remain in-frame.

In an alternative method, a scFv gene may be constructed with wildtype CDR regions (such as those of antibody 1-60-46) and then mutated using techniques known in the art.

The isolated nucleic acid molecule encoding the VH region can be converted to a full-length heavy chain gene by operatively linking the VH-encoding nucleic acid molecule to another nucleic acid molecule encoding heavy chain constant regions (CH1, CH2 and CH3). The sequences of human heavy chain constant region genes are known in the art (See for example, Kabat, E. A., et al., *Sequences of Proteins of Immunological Interest, Fifth Edition*, U.S. Department of Health and Human Services, NIH Publication No. 91-3242 (1991)). In another aspect, the present invention further encompasses all known human heavy chain constant regions, including but not limited to, all known allotypes of the human heavy chain constant region. Nucleic acid fragments encompassing these regions can be obtained by standard PCR amplification. The heavy chain constant region can be an IgG1, IgG2, IgG3, IgG4, IgA, IgE, IgM or IgD constant region.

The isolated nucleic acid molecule encoding the VL region can be converted to a full-length light chain gene (as well as a Fab light chain gene) by operatively linking the VL-encoding nucleic acid molecule to another nucleic acid molecule encoding the light chain constant region, CL. The sequences of human light chain constant region genes are known in the art (see e.g., Kabat, E. A., et al., *Sequences of Proteins of Immunological Interest, Fifth Edition*, U.S. Department of Health and Human Services, NIH Publication No. 91-3242 (1991)). The present invention encompasses all known human light chain constant regions, including but not limited to, all known allotypes of the human light chain constant region. Nucleic acid fragments encompassing these regions can be obtained by standard PCR amplification. The light chain constant region can be a kappa or lambda constant region, but most preferably is a kappa constant region.

It is to be understood that the specific designations of FR and CDR regions within a particular heavy or light chain region may vary depending on the convention or numbering system used to identify such regions (e.g. Chothia, Kabat, Oxford Molecular's AbM modeling software, all of which are known to those of ordinary skill in the art). For the purposes of the present invention, the Oxford Molecular's AbM modeling software numbering system is used.

To create a scFv gene, the VH- and VL-encoding nucleic acid fragments are operatively linked to another fragment encoding a flexible linker, such as, a linker that is encoded by the amino acid sequence GPAKELTPLKEAKVS (SEQ ID NO:36). Examples of other linker sequences that can be used in the present invention can be found in Bird et al., *Science* 242:423-426 (1988), Huston et al., *Proc. Natl. Acad. Sci. USA* 85:5879-5883 (1988) and McCafferty et al., *Nature,* 348:552-554 (1990).

To express the antibodies, or antibody portions of the invention, nucleic acid molecules encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or, more typically, both genes are inserted into the same expression vector. The antibody genes are inserted into the expression vector by standard methods (for example, ligation of complementary restriction sites on the antibody gene fragment and vector, or blunt end ligation if no restriction sites are present). Prior to the insertion of the light or heavy chain sequences, the expression vector may already carry antibody constant region sequences. For example, one approach to converting the VH and VL sequences to full-length antibody genes is to insert them into expression vectors already encoding heavy chain constant and light chain constant regions, respectively, such that the VH segment is operatively linked to the CH "segment" within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The single peptide can be an immunoglobin signal peptide or a heterologous signal peptide (i.e., a signal peptide from a non-immunoglobulin protein).

In addition to the antibody chain genes, the recombinant expression vectors can carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; *Gene Expression Technology. Methods in Enzymology* 185, Academic Press, San Diego, Calif. (1990). It will be appreciated by those skilled in the art that the design of the expression vector, including the selection of regulatory sequences may depend on such factors as the choice of the host cell to be transformed, the level of the expression of protein desired, etc. Preferred regulatory sequences for mammalian host cell expression include viral elements that direct high levels of protein expression in mammalian cells, such as promoters and/or enhancers derived from cytomegalovirus (hereinafter "CMV") (such as the CMV promoter/enhancer), Simian Virus 40 (hereinafter "SV40") (such as the SV40 promoter/enhancer), adenovirus, (such as the adenovirus major late promoter ("AdMLP")) and polyoma. For further description of viral regulatory elements, and sequences thereof, see for example, U.S. Pat. No. 5,168,062, U.S. Pat. No. 4,510,245 and U.S. Pat. No. 4,968,615.

In addition to the antibody chain genes and regulatory sequences, recombinant expression vectors may carry additional sequences, such as sequences that regulate replication of the vector in host cells (e.g., origins of replication) and selectable marker genes. The selectable marker gene facilitates selection of host cells into which the vector has been introduced (See, for example, U.S. Pat. Nos. 4,399,216, 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (hereinafter "DHFR") gene for use in dhfr-host cells with methotrexate selection/amplification and the neomycin (hereinafter "neo") gene for G418 selection.

For expression of the light and heavy chains, the expression vector(s) encoding the heavy and light chains are transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (See, Boss, M. A. and Wood, C. R., *Immunology Today* 6:12-13 (1985)).

Preferred mammalian host cells for expressing the recombinant antibodies of the invention include the CHO cells (including dhfr-CHO cells, described in Urlaub and Chasin, *Proc. Natl. Acad. Sci. USA* 77:4216-4220 (1980), used with a DHFR selectable marker, for example, as described in R. J. Kaufman and P. A. Sharp, *Mol. Biol.* 159:601-621 (1982)), NSO myeloma cells, COS cells, HEK-293 cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce portions of intact antibodies, such as Fab fragments, F(ab') fragments or scFv molecules. It will be understood that variations on the above procedure are within the scope of the present invention. For example, it may be desirable to transfect a host cell with nucleic acid molecule encoding either the light chain or the heavy chain (but not both) of an antibody of the present invention. Recombinant DNA technology may also be used to remove some or all of the nucleic acid molecules encoding either or both of the light and heavy chains that are not necessary for binding to at least one epitope on at least one immunosuppressive agent. The molecules expressed from such truncated nucleic acid molecules also are encompassed by the antibodies of the invention.

In a preferred system for recombinant expression of an antibody, or antigen binding portion thereof, of the invention, a recombinant expression vector encoding both the antibody heavy chain and the antibody light chain is introduced into dhfr-CHO cells by liposome-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector. Cells were cultured in medium without hypoxanthine and thymidine to obtain those CHO cells that have acquired the DHFR gene from the transfecting vector. Antigen specific screening methods were used to identify those clones that expressed the highest quantity of antibody. Those individual clones were expanded and were routinely re-screened. Two cell lines were chosen for further characterization, Tacrolimus 1-60-46 AM2 CHO 2-577 and Tacrolimus 1-60-46 AM2 CHO 1-1157. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

In view of forgoing, another aspect of the invention pertains to nucleic acid, vector and host cell compositions that can be used for recombinant expression of the antibodies and antibody portions of the invention. The amino acid sequence encoding the heavy chain CDR 2 region of AM2 and variants thereof is shown in SEQ ID NO:16. The amino acid sequence encoding the AM2 light chain CDR 1 region is shown in SEQ ID NO:22. The amino acid sequence encoding the AM2 light chain CDR 3 is shown in SEQ ID NO:23.

V. Selection of Recombinant Antibodies

The antibodies of the present invention, including the AM2 or AM2-related antibodies disclosed herein, can be isolated by screening of a combinatorial antibody library. The combinatorial antibody library can be prepared using bio-display techniques known in the art, such as, but not limited to, phage display, bacterial display, ribosomal/mRNA display, DNA display and in vitro compartmentalization. For example, the combinatorial antibody library is a recombinant combinatorial library, such as a scFv yeast display library, prepared using murine, chimeric, humanized or human VL and VH cDNAs. Methodologies for preparing and screening such libraries are known in the art. In addition to commercially available vectors for generating yeast display libraries (such as, the pYD1 vector, Invitrogen, Carlsbad, Calif.) examples of methods and reagents particularly amenable for use in generating and screening antibody display libraries can be found in, for example, Boder E. T. and Wittrup K. D., Yeast surface display for directed evolution of protein expression, affinity, and stability, *Methods Enzymol.,* 328:430-44 (2000), Boder E. T. and Wittrup K. D., Yeast surface display for screening combinatorial polypeptide libraries, *Nat. Biotechnol.* 15(6): 553-7 (June 1997) and Hawley and Hawley, eds., *Methods in Molecular Biology: Flow Cytometry Protocols,* 2nd ed., Humana Press, Totowa, N.J., pages 311-332 (2004).

In a preferred embodiment, to isolate antibodies with high binding affinity, such as any of the antibodies described in Section II herein, an antibody that is known to immunospecifically bind to at least one epitope on at least one immunosuppressive agent is first used to generate murine heavy and light chain sequences expressed as scFvs on the surface of yeast (preferably, *Saccharomyces cerevisiae*). These antibody (such as antibody produced by hybridoma cell line 1-60-46) scFvs are analyzed to determine the disassociation rate constant (namely, the $k_{off}$ or $k_d$) of these antibodies. Such constructs then are screened, preferably using biotinylated-tacrolimus antigen (hereinafter referred to as "bt-tacro"). The disassociation rate constant data can then be plotted as mean fluorescence intensity ("MFI") versus time (in seconds). A first order decay equation can be used to fit the data. An example of such a formula that can be used is:

$$y=m1*\exp(-m2*M0)+m3$$

where m1 is the maximum fluorescence at time zero (*=multiplication and exp=exponential);

where m2 is the dissociation rate constant (the formula for determining off-rate is well known to those skilled in the art);

where M0 is time x (x being the time that is being measured); and where m3 is the background being generated from the system.

The dissociation rate constant data can be used to identify antibodies of the present invention with improved dissociation rates from mutagenic libraries.

The VH and VL segments of the preferred VH/VL pair(s) can be randomly mutated, preferably within the CDR 2 region of VH, the CDR 1 region and/or CDR 3 region of VL in a process analogous to the in vivo somatic mutation process responsible for affinity maturation of antibodies during a natural immune response. This in vitro affinity maturation can be accomplished by replacing a portion of each CDR with a degenerate single-stranded oligonucleotide encoding three amino acids within the CDR being targeted. The replacement of a portion of each CDR with a new randomized sequence (up to 8000 possibilities) can be accomplished by homologous recombination in yeast (see, for example, Example 4). These randomly mutated VH and VL segments can be analyzed for binding to at least one epitope on at least one immunosuppressive agent in the context of a scFv. ScFvs exhibiting an improved fluorescence and that (a) in the presence of a physiological diluent (PBS (pH 7.4) and 1% BSA), bind to at least one epitope on at least one immunosuppressive agent and have a $k_d$ of less than $1.3\times10^{-4}$/sec, preferably with a $k_d$ ranging from $1.29\times10^{-4}$/sec and $1.0\times10^{-6}$/sec, and more preferably, with a $k_d$ ranging from $1.29\times10^{-4}$/sec and $1.0\times10^{-5}$/sec; or (b) in the presence of at least one selection diluent, bind to at least one epitope on at least one immunosuppressive agent and have a $k_d$ of less than $9.38\times10^{-4}$/sec, preferably with a $k_d$ ranging from $9.37\times10^{-4}$/sec and $1.0\times10^{-6}$/sec, and more preferably with a $k_d$ ranging from $9.37\times10^{-4}$/sec and $1.0\times10^{-5}$/sec, can then be isolated and the CDR mutation identified by sequencing.

To further increase the binding affinity, individual mutations isolated from the mutagenic libraries described above are combined. In a preferred embodiment, scFv genes containing the different mutations obtained in CDR 2 region of the VH gene coupled with different mutations obtained in CDR 1 region of the VL gene and/or different mutations obtained in CDR 3 region of the VL gene are constructed. As another embodiment, scFv genes containing different mutations obtained in CDR 1 region of the VL gene and different mutations obtained in CDR 3 region of the VL gene are constructed. The genetic manipulations to create these mutant combinations use techniques known in the art. The combination mutant scFv clones exhibiting an improved fluorescence and that (a) in the presence of at least one physiological diluent (PBS (pH 7.4) and 1% BSA), bind to at least one epitope on at least one immunosuppressive agent and have a $k_d$ of less than $1.3\times10^{-4}$/sec, preferably with a $k_d$ ranging from $1.29\times10^{-4}$/sec and $1.0\times10^{-6}$/sec, and more preferably, with a $k_d$ ranging from $1.29\times10^{-4}$/sec and $1.0\times10^{-5}$/sec; or (b) in the presence of at least one selection diluent, after exposure to at least one selection diluent, or after incubation with at least one selection diluent, bind to at least one epitope on at least one immunosuppressive agent and have a $k_d$ of less than $9.38\times10^{-4}$/sec, preferably with a $k_d$ ranging from $9.37\times10^{-4}$/sec and $1.0\times10^{-6}$/sec, and more preferably with a $k_d$ ranging from $9.37\times10^{-4}$/sec and $1.0\times10^{-5}$/sec, can then be characterized and the CDR mutations verified by sequencing.

Following screening of a recombinant scFv display library, clones having the desired characteristics are selected for conversion. Nucleic acid molecules encoding the selected antibody can be recovered from the display package (for example, from the yeast expression vector) and subcloned into other expression vectors by standard recombinant DNA techniques. If desired, the nucleic acid can be further manipulated to create other antibody forms of the invention (for example, linked to nucleic acid encoding additional immunoglobulin domains, such as additional constant regions). To express a recombinant human antibody isolated by screening of a combinatorial library, the DNA encoding the antibody is cloned into a recombinant expression vector and introduced into a mammalian host cells, as described in further detail in Section IV above.

VI. Diagnostic Immunoassays

In another aspect, the present invention relates to diagnostic immunoassays that can be used for the qualitative and/or quantification of at least one immunosuppressive agent (namely, an analyte) in a test sample. The diagnostic immunoassays of the present invention can be conducted using any format known in the art, such as, but not limited to, a competitive inhibition format (including both forward and reverse competitive inhibition assays) or a fluorescence polarization format.

In diagnostic immunoassays for the qualitative detection of at least one immunosuppressive agent in a test sample, at least one antibody that binds to at least one epitope of at least one immunosuppressive agent thereof is contacted with at least one test sample suspected of containing or that is known to contain at least one immunosuppressive agent to form an antibody-immunosuppressive agent immune complex. The antibodies described in Section II herein can be used in such immunoassays to form such antibody-immunosuppressive agent immune complexes in at least one test sample. These immune complexes can then detected using routine techniques known to those skilled in the art. For example, the antibody of the present invention can be labeled with a detectable label to detect the presence antibody-immunosuppressive agent complex. Alternatively, at least one immunosuppressive agent in the test sample can be labeled with a detectable label and the resulting antibody-immunosuppressive agent immune complexes detected using routine techniques known to those skilled in the art. Detectable labels and their attachment to antibodies are discussed in more detail infra.

The inventors have discovered that a diagnostic immunoassay can be performed using the antibodies of the present invention. More specifically, the antibodies of the present invention can be used in said immunoassay. Preferably, the antibody of the present invention, as an immunoglobulin, specifically binds to at least one epitope on at least one immunosuppressive agent with (a) a $K_D$ less than $1.9\times10^{-11}$ M, preferably a $K_D$ between $1.89\times10^{-11}$ M to $1.0\times10^{-13}$ M and most preferably, a $K_D$ between $1.89\times10^{-11}$ M to $1.0\times10^{-12}$ M when said antibody has not been exposed to, incubated with or is in the presence of at least one selection diluent; or (b) a $K_D$ less than $1.52\times10^{-10}$ M, preferably a $K_D$ between $1.51\times10^{-10}$ M to $1.0\times10^{-11}$ M, and, most preferably, a $K_D$ between $1.51\times10^{-10}$ M to $1.0\times10^{-11}$ M with a when said antibody has been exposed to, incubated with or is in the presence of at least one selection diluent (the antibody may be exposed to or incubated with at least one selection diluent either prior to or during the immunoassay, the timing of the exposure or incubation is not critical). As an scFv, the antibody of the present invention specifically binds to at least one epitope on at least one immunosuppressive agent with (a) a $k_d$ of less than $1.3\times10^{-4}$/sec, preferably with a $k_d$ ranging from $1.29\times10^{-4}$/sec and $1.0\times10^{-6}$/sec, and more preferably, with a $k_d$ ranging from $1.29\times10^{-4}$/sec and $1.0\times10^{-5}$/sec when said antibody has not been exposed to, incubated with or is in the presence of at least one selection diluent; or (b) a $k_d$ of less than $9.38\times10^{-4}$/sec, preferably with a $k_d$ ranging from $9.37\times10^{-4}$/sec and $1.0\times10^{-6}$/sec, and more preferably with a $k_d$ ranging from $9.37\times10^{-4}$/sec and $1.0\times10^{-5}$/sec when said antibody has been exposed to, incubated with or is in the presence of at least one selection diluent (the antibody may be exposed to or incubated with at least one selection diluent either prior to or during the immunoassay, the timing of the exposure or incubation is not critical).

In a preferred embodiment, an aliquot of a labeled antigen of at least one immunosuppressive agent of a known concentration is used to compete with at least one immunosuppressive agent in a test sample for binding to an antibody (such as an antibody of the present invention) in a forward competitive assay format. Antigens of immunosuppressive agents and methods of making said antigens are well known in the art and are commercially available. The immunosuppressive agent or antigen of said immunosuppressive agent can be labeled with any detectable label known to those skilled in the art. For example, but not limiting, the detectable label can be a radioactive label, such as, $^{3}H$, $^{125}I$, $^{35}S$, $^{14}C$, $^{32}P$, $^{33}P$, an enzymatic label, such as horseradish peroxidase, alkaline peroxidase, glucose 6-phosphate dehydrogenase, etc., a chemiluminescent label, such as, acridinium esters, luminal, isoluminol, thioesters, sulfonamides, phenanthradinium esters, etc. a fluorescence label, such as, fluorescein (5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, etc.), rhodamine, phycobiliproteins, R-phycoerythrin, quantum dots (zinc sulfide-capped cadmium selenide), a thermometric label or an immuno-polymerase chain reaction label. An introduction to labels, labeling procedures and detection of labels is found in Polak and Van Noorden, *Introduction to Immunocytochemistry*, 2$^{nd}$ ed., Springer Verlag, N.Y. (1997) and in Haugland, *Handbook of Fluorescent Probes and Research Chemicals* (1996), which is a combined handbook and catalogue published by Molecular Probes, Inc., Eugene, Oreg. For example, as described in the Examples herein, biotinylated-tacrolimus or acridinium-tacrolimus antigen can also be used in said competitive formats.

In a forward competition assay, an immobilized antibody (such as an antibody of the present invention) can either be sequentially or simultaneously contacted with the test sample and a labeled immunosuppressive agent or antigen of an immunosuppressive agent. The immunosuppressive agent or antigen of said immunosuppressive agent can be labeled with any detectable label known to those skilled in the art. In this assay, the antibody of the present invention can be immobilized on to a solid support. Moreover, if necessary, the solid support can be derivatized to allow reactivity with various functional groups on the antibody. Such derivatization requires the use of certain coupling agents such as, but not limited to, maleic anhydride, N-hydroxysuccinimide and 1-ethyl-3-(3-dimethylaminopropyl)carbodiimide. Alternatively, the antibody of the present invention can be coupled to an antibody, such as an antispecies antibody, that has been immobilized on to a solid support, such as a microparticle (See, Example 9).

The labeled immunosuppressive agent or antigen of said immunosuppressive agent, the test sample and the antibody are incubated in order to allow for the formation of an antibody (or multiple antibody)-immunosuppressive agent complex. The incubation can be carried out at a pH of from about 4.5 to about 10.0, at a temperature of from about 2° C. to about 45° C., and for a period from at least about one (1) minute to about eighteen (18) hours, preferably from about 1-24 minutes, most preferably from about 4-18 minutes. Two different species of antibody-immunosuppressive agent complexes are then generated. Specifically, one of the antibody-immunosuppressive agent complexes generated contains a detectable label while the other antibody-immunosuppressive agent complex does not contain a detectable label. The antibody-immunosuppressive agent complex can be, but does not have to be, separated from the remainder of the test sample prior to quantification of the detectable label. Regardless of whether the antibody-immunosuppressive agent complex is separated from the remainder of the test sample, the amount of detectable label in the antibody-immunosuppressive agent complex is then quantified. For example, if an enzymatic label is used, the labeled complex is reacted with a substrate for the label that gives a quantifiable reaction such as the development of color. If the label is a radioactive label, the label is quantified using a scintillation counter. If the label is a fluorescent label, the label is quantified by stimulating the label with a light of one color (which is known as the "excitation wavelength") and detecting another color (which is known as the "emission wavelength") that is emitted by the label in response to the stimulation. If the label is a chemiluminescent label, the label is quantified detecting the light emitted either visually or by using luminometers, x-ray film, high speed photographic film, a CCD camera, etc. The concentration of at least one immunosuppressive agent in the test sample can then be determined by comparing the quantity of detectable label in the antibody-immunosuppressive agent complex to a standard curve. The standard curve can be generated using serial dilutions of at least one immunosuppressive agent of known concentration, by mass spectroscopy, gravimetrically and by other techniques known in the art.

The antibody-immunosuppressive agent complex can be separated from the test sample by binding the antibody to a solid support, such as the solid supports, and then removing the remainder of the test sample from contact with the solid support. For example, if the at least first antibody is bound to a solid support, such as a well or a bead, separation can be accomplished by removing the fluid (from the test sample) from contact with the solid support.

In a reverse competition assay, an immobilized immunosuppressive agent or an antigen of said immunosuppressive agent can either be sequentially or simultaneously contacted with a test sample and at least one labeled antibody. An example of an antibody that specifically binds to at least one epitope on at least one immunosuppressive agent is the antibody produced by CHO cell line 1-60-4 6 AM2 CHO 2-577 or CHO cell line 1-60-46 AM2 CHO 1-1157. The antibody can be labeled with any detectable label known to those skilled in the art. The detectable label can be bound to the antibodies either directly or through a coupling agent. An example of a coupling agent that can be used is EDAC (1-ethyl-3-(3-dimethylaminopropyl) carbodiimide, hydrochloride) that is commercially available from Sigma-Aldrich, St. Louis, Mo. Other coupling agents that can be used are known in the art. Methods for binding a detectable label to an antibody are known in the art. Additionally, many detectable labels can be purchased or synthesized that already contain end groups that facilitate the coupling of the detectable label to the antibody, such as, N10-(3-sulfopropyl)-N-(3-carboxypropyl)-acridinium-9-carboxamide, otherwise known as CPSP-Acridinium Ester or N10-(3-sulfopropyl)-N-(3-sulfopropyl)-acridinium-9-carboxamide, otherwise known as SPSP-Acridinium Ester.

The immunosuppressive agent or an antigen of said immunosuppressive agent can be bound to a solid support, such as the solid supports discussed above in connection with the forward competitive format.

The immobilized immunosuppressive agent or antigen of said immunosuppressive agent, test sample and at least one labeled antibody are incubated under conditions similar to those described above in connection with the sandwich assay format. Two different species immunosuppressive agent-antibody complexes are then generated. Specifically, one of the immunosuppressive agent-antibody complexes generated is immobilized and contains a detectable label while the other immunosuppressive agent-antibody complex is not immobilized and contains a detectable label. The non-immobilized immunosuppressive agent-antibody complex and the remainder of the test sample are removed from the presence of the immobilized immunosuppressive agent-antibody complex through techniques known in the art, such as washing. Once the non-immobilized immunosuppressive agent antibody complex is removed, the amount of detectable label in the immobilized immunosuppressive agent-antibody complex is then quantified. The concentration of at least one immunosuppressive agent in the test sample can then be determined by comparing the quantity of detectable label in the immunosuppressive agent-complex to a standard curve. The standard curve can be generated using serial dilutions of at least one immunosuppressive agent of known concentration, by mass spectroscopy, gravimetrically and by other techniques known in the art.

In a fluorescence polarization assay, in one embodiment, an antibody or functionally active fragment thereof is first contacted with an unlabeled test sample suspected of containing at least one immunosuppressive agent to form an unlabeled immunosuppressive agent-antibody complex. The unlabeled immunosuppressive agent-antibody complex is then contacted with a fluorescently labeled immunosuppressive agent or antigen of said immunosuppressive agent. The labeled immunosuppressive agent or antigen of said immunosuppressive agent competes with any unlabeled at least one immunosuppressive agent in the test sample for binding to the antibody or functionally active fragment thereof. The amount of labeled immunosuppressive agent-antibody complex formed is determined and the amount of immunosuppressive agent in the test sample determined via use of a standard curve.

Preferably, the antibody used in a fluorescence polarization assay specifically binds to an at least one epitope on an immunosuppressive agent. An example of an antibody that specifically binds to at least one epitope on at least one immunosuppressive agent is the antibody produced by CHO cell line 1-60-46 AM2 CHO 2-577 or CHO cell line 1-60-46 AM2 CHO 1-1157.

The antibody, labeled immunosuppressive agent or labeled antigen of said immunosuppressive agent and test sample and at least one labeled antibody are incubated under conditions similar to those described above in connection with the forward competitive assay format.

Alternatively, in another embodiment, an antibody or functionally active fragment thereof is simultaneously contacted with a fluorescently labeled immunosuppressive agent or an antigen of an immunosuppressive agent and an unlabeled test sample suspected of containing at least one immunosuppressive agent thereof to form both labeled immunosuppressive agent-antibody complexes and unlabeled immunosuppressive agent-antibody complexes. The amount of labeled immunosuppressive agent-antibody complex formed is determined and the amount of immunosuppressive agent in the test sample determined via use of a standard curve. The antibody used in this immunoassay specifically binds to at least one epitope on at least one immunosuppressive agent. An example of an antibody that specifically binds to at least one epitope on at least one immunosuppressive agent is the antibody produced by CHO cell line 1-60-46 AM2 CHO 2-577 or CHO cell line 1-60-46 AM2 CHO 1-1157.

Alternatively, in yet another embodiment, an antibody (such as antibody of the present invention, such as an antibody produced by CHO cell line 1-60-46 AM2 CHO 2-577 or CHO cell line 1-60-46 AM2 CHO 1-1157) or functionally active fragment thereof is first contacted with a fluorescently labeled immunosuppressive agent or an antigen from said immunosuppressive agent to form a labeled immunosuppressive agent-antibody complex. The labeled immunosuppressive agent-antibody complex is then contacted with an unlabeled test sample suspected of containing an immunosuppressive agent or an antigen of an immunosuppressive agent. Any unlabeled at least one immunosuppressive agent in the test sample competes with the labeled immunosuppressive agent or an antigen of an immunosuppressive agent for binding to the antibody or functionally active fragment thereof. The amount of labeled immunosuppressive agent-antibody complex formed is determined the amount of immunosuppressive agent in the test sample determined via use of a standard curve. The antibody used in this immunoassay specifically binds to at least one epitope on at least one immunosuppressive agent. An example of an antibody that specifically binds to at least one epitope on at least one immunosuppressive agent is the antibody produced by CHO cell line 1-60-46 AM2 CHO 2-577 or CHO cell line 1-60-46 AM2 CHO 1-1157.

VII. Methods for Selecting Antibodies and Specific Binding Partners

The present invention also provides methods for selecting an antibody or a specific binding partner. The selected antibody or specific binding partner selected pursuant to the methods described herein can be used in a diagnostic immunoassay for detecting an analyte in a test sample, quantifying the amount of analyte in a test sample, or detecting an analyte in a test sample and quantifying the amount of analyte in a test sample.

In one aspect, the present invention relates to methods for selecting an antibody (such as, an affinity maturated antibody). The method involves contacting at least one antibody with a sample in the presence of at least one selection diluent. Alternatively, the method involves first incubating the at least one antibody with at least one selection diluent and then contacting the at least one antibody with the sample. The order in which the at least one antibody, sample and at least one selection diluent or, in the case of a prior incubation, the at least one antibody and at least one selection diluent, followed by the at least one antibody and the sample, are contacted is not critical and can be performed sequentially or simultaneously. Additionally, the amount of antibody, sample or both, used in the method is not critical. Optionally, before the sample is exposed to the at least one selection diluent, at least one physiological diluent may be added to the test sample (the amount of a physiological diluent to be added to a test sample can be readily determined by those skilled in the art) in order to approximate, mimic or simulate the in vivo physiological conditions of the subject from whom the sample was derived (in other words, to make the test sample more “physiological like”). If said sample is exposed to at least one physiological diluent, once the at least one selection diluent is added to the test sample or once the test sample is exposed to the at least one selection diluent, it is expected that the at least one selection diluent will change the conditions of the test sample and make it “non-physiological”. For example, if at least one physiological diluent is added to a test sample, the addition of at least one selection diluent to the test sample may raise or lower the pH of the test sample, increase the amount of sodium or potassium salt in the test sample, increase the amount of solvent in the test sample, etc.

The sample used in the method is the source of an analyte containing at least one epitope of interest. The sample can be a test sample from a subject or may not be derived from a subject but nonetheless comprises the analyte containing the at least one epitope of interest. The sample may comprise, but not be limited to, antibodies, antigens, haptens, hormones, drugs, enzymes, receptors, proteins, peptides, polypeptides, oligonucleotides or polynucleotides of interest. For example, the sample may be an immunosuppressive agent, such as tacrolimus or cyclosporine (namely, the drug itself). Alternatively, the sample may be a whole blood sample obtained from a subject that contains tacrolimus or cyclosporine. Alternatively, the sample may contain an avidin-labeled protein.

The at least one antibody selected for testing in the method described herein is known by one skilled in the art to bind to at least one epitope of interest (Namely, the at least one antibody is known to be a specific binding partner for the analyte (antigen) containing the epitope of interest). Preferably, the antibody and the antigen are part of a specific binding pair. For example, the sample may be tacrolimus (namely, the drug itself). The antibody may be an antibody produced from hybridoma cell line 1-60-46, CHO cell line 1-60-46 AM2 CHO 2-577 or CHO cell line 1-60-46 AM2 CHO 1-1157 as described herein, which binds to tacrolimus. It is preferred, although not necessary, that prior to performing the method described herein, that the equilibrium dissociation constant ($K_D$), disassociation rate constant ($k_d$), association rate constant ($k_a$) or functional activity of the at least one antibody be tested in the method, in the presence and absence of the selection diluent, be determined to serve as a baseline measurement.

Preferably, the selection diluent selected for use in the method described herein (a) is known by one skilled in the art to increase the $K_D$ (and thus decrease the $k_a$ and/or increase the $k_d$) of the at least one antibody being tested in the method or is believed by said skilled person to likely increase the $K_D$ of the at least one antibody being tested in the method; (b) is known by one skilled in the art to lower the functional activity of the at least one antibody being tested in the method or is believed by said skilled person likely to lower the functional activity of the at least one antibody being tested in method, if said at least one antibody were to be incubated with or used with or in the presence of said selection diluent (such as, but not limited to, being used prior to or during an diagnostic immunoassay); or (c) any combinations of (a)-(b).

Assay extraction buffers containing one or more organic solvents, such as a combination of 90% methanol and 10% ethylene glycol (and optionally, 100 mM zinc sulfate), are used to extract tacrolimus from a whole blood test sample obtained from a subject receiving this immunosuppressive agent as a part of the subject’s treatment. The inventors of the present invention discovered that these assay extraction buffers that are employed in diagnostic immunoassays alter the $K_D$, functional activity or both the $K_D$ and functional activity of one or more antibodies used in said immunoassay. Therefore, it is preferred that in the method described herein that the selection diluent be used to approximate, simulate or mimic the reaction conditions of a diagnostic immunoassay. By using the selection diluent to approximate, simulate or mimic the reaction conditions of a diagnostic immunoassay, the method of the present invention allows one skilled in the art to select an antibody that will exhibit a higher affinity or functional activity in a diagnostic immunoassay than antibodies that are not selected pursuant to this method.

In order to facilitate the method, all or only a portion of the at least one antibody used in the method may be expressed using the techniques described in Sections IV and V herein (such as bio-display) in such a way to couple the phenotype of said antibody with the genotype of said antibody. Preferably, this allows the gene of said antibody displaying a trait of interest (for example, decreased dissociation rate in presence of an organic solvent) to be isolated after application of a selective pressure, namely incubation with a selection diluent resulting in non-physiological conditions or containing a binding competitor. Additionally, recombinant libraries introducing various changes into the starting antibody gene sequence can be constructed using methods known to those skilled in the art and also described in Sections IV and V herein. The sample used in the method may be immobilized to a solid support, such as, but not limited to, an absorbent polymer present in enzyme immunoassay ("EIA") plate or other matrices such as, but not limited to, Sepharose or glass; may be expressed (such as in native or recombinant forms) on cell surface of natural or recombinant cell line by means known to those skilled in the art. Alternatively, the sample may not be immobilized but may simply be present in solution. Additionally, the at least one antibody, sample or both can be labeled with a detectable label using the techniques described in Section VI.

The at least one antibody, sample and at least one selection diluent or the at least one antibody and sample (if the antibody is previously incubated with the at least one selection diluent) are allowed to incubate in order to allow for the formation of antibody (or multiple antibody)-analyte complexes, analyte-antibody complexes or combinations of antibody (multiple antibody)-analyte and analyte-antibody complexes. The incubation can be carried out at a pH of from about 4.5 to about 10.0, at a temperature of from about 2° C. to about 45° C., and for a period from at least about one (1) minute to about forty-eight (48) hours.

After incubation, those antibodies displaying phenotypic enhancements for the desired trait are selectively enriched after removal of unwanted antibodies. Unwanted antibodies can be removed by washing by virtue of their inability to bind immobilized sample to the same degree as antibodies having enhanced phenotypic properties. Alternatively, antibodies displaying phenotypic enhancements for the desired trait can be enriched from unwanted antibodies using a reporter system as described in Section VI to identify desired antibodies and enable subsequent separation from unwanted antibodies. A preferred, but not limiting, embodiment uses fluorescence-activated cell sorting ("FACS"), in conjunction with fluorescently labeled sample, to selectively identify and isolate antibodies with desired phenotypic enhancements. Unlabeled sample can also be used to identify and isolate antibodies with desired phenotypic enhancements in conjunction with FACS if a second fluorescently labeled reagent capable of binding to a non-overlapping epitope on the sample is available. Typically, the enriched clones with the enhanced phenotypic trait are amplified and the selection process is repeated for further enrichment and refinement.

After multiple rounds of selection as described above, the $K_D$, $k_d$, $k_a$ or functional activity of the at least one antibody or combinations thereof can be determined using routine techniques known in the art. For example, the $K_D$, $k_d$ or $k_a$ can be determined using KinExA® or Biacore® assays. Methods for determining the functional activity of an antibody are also well known in the art and include, but are not limited to, KinExA® and Biacore® assays, radioimmunoassays ("RIAs"), enzyme immunoassays ("EIAs"), chemiluminescent immunoassays ("CIAs"), fluorescence correlation spectroscopy ("FCS"), fluorescence-activated cell sorting ("FACS") or fluorescence polarization immunoassay ("FPIA"). The antibody that exhibits the best $K_D$, $k_d$ or $k_a$ or functional activity in the presence of the selection diluent when compared to the other antibodies tested (and optionally, the baseline measurement) will be deemed to be an improved antibody (for example, an affinity maturated antibody) and selected for further development, such as use in a diagnostic immunoassay.

In second aspect, the present invention relates to methods for selecting a specific binding partner for detecting an analyte in a test sample. The method involves contacting a specific binding partner with a sample in the presence of at least one selection diluent. The order in which the specific binding partner, sample and at least one selection diluent are contacted is not critical and can performed sequentially or simultaneously. Additionally, the amount of the specific binding partner, or sample used in the method is not critical.

The sample used in the method is the source of an analyte containing at least one epitope of interest. The sample can be a test sample from a subject or may not be derived from a subject but nonetheless comprises the analyte containing the at least one epitope of interest. The sample may comprise, but not be limited to, antibodies, antigens, haptens, hormones, drugs, enzymes, receptors, proteins, peptides, polypeptides, oligonucleotides or polynucleotides of interest. For example, the sample may be an immunosuppressive agent, such as tacrolimus or cyclosporine (namely, the drug itself). Alternatively, the sample may be a whole blood sample obtained from a subject that contains tacrolimus or cyclosporine.

The at least one specific binding partner selected for testing in the method described herein is known by one skilled in the art to bind to at least one epitope of interest contained in analyte in the test sample. For example, the sample may be tacrolimus or cyclosporine (namely, the drug itself). The specific binding partner may be proteins present in a test sample (such as serum), such as, but not limited to, cyclophilin or FK binding protein ("FKBP"). It is preferred, although not necessary, that prior to performing the method described herein, that the equilibrium dissociation constant ($K_D$), disassociation rate constant ($k_d$), association rate constant ($k_a$) or functional activity of the at least one specific binding partner be tested in the method, in the presence and absence of the selection diluent, be determined to serve as a baseline measurement.

Preferably, the selection diluent selected for use in the method described herein (a) is known by one skilled in the art to increase the $K_D$ (and thus decrease the $k_a$ and/or increase the $k_d$) of the at least one antibody being tested in the method or is believed by said skilled person to likely increase the $K_D$ of the at least one antibody being tested in the method; (b) is known by one skilled in the art to lower the functional activity of the at least one antibody being tested in the method or is believed by said skilled person likely to lower the functional activity of the at least one antibody being tested in method, if said at least one antibody were to be incubated with or used with or in the presence of said selection diluent (such as, but not limited to, being used prior to or during an diagnostic immunoassay); or (c) any combinations of (a)-(b).

As previously described herein, assay extraction buffers containing one or more organic solvents, such as a combination of 90% methanol and 10% ethylene glycol (and optionally, 100 mM zinc sulfate), are used to extract tacrolimus from a whole blood test sample obtained from a subject receiving this immunosuppressive agent as a part of the subject's treatment. Therefore, it is preferred that in the method described herein that the selection diluent be used to approximate, simulate or mimic the reaction conditions of a diagnostic immunoassay. By using the selection diluent to approximate, simulate or mimic the reaction conditions of a diagnostic immunoassay, the method of the present invention allows one skilled in the art to select an improved specific binding partner that can be further evaluated for use in a diagnostic immunoassay.

In order to facilitate the method, all or only a portion of the at least one-specific binding partner used in the method may be expressed using the techniques described in Sections IV and V herein in such a way to couple the phenotype of said antibody with the genotype of said antibody. Preferably, this allows the gene of said specific binding partner displaying a trait of interest (for example, decreased dissociation rate in presence of an organic solvent) to be isolated after application of a selective pressure, namely incubation with a selection diluent resulting in non-physiological conditions or containing a binding competitor. Additionally, recombinant libraries introducing various changes into the starting specific binding partner gene sequence can be constructed using methods known to those skilled in the art and also described in Sections IV and V herein. The sample used in the method may be immobilized to a solid support, such as, but not limited to, an absorbent polymer present in enzyme immunoassay ("EIA") plate or other matrices such as, but not limited to, Sepharose or glass; may be expressed (such as in native or recombinant forms) on cell surface of natural or recombinant cell line by means known to those skilled in the art. Alternatively, the sample may not be immobilized but may simply be present in solution. Additionally, the at least one specific binding partner, sample or both can be labeled with a detectable label using the techniques described in Section VI.

The specific binding partner, sample and at least one selection diluent are allowed to incubate in order to allow for the formation of specific binding partner (or multiple specific binding partner)-analyte complexes. The incubation can be carried out at a pH of from about 4.5 to about 10.0, at a temperature of from about 2° C. to about 45° C., and for a period from at least about one (1) minute to about forty eight (48) hours.

After incubation, those specific binding partners displaying phenotypic enhancements for the desired trait are selectively enriched after removal of unwanted specific binding partners. Unwanted specific binding partners can be removed by washing by virtue of their inability to bind immobilized sample to the same degree as specific binding partners having enhanced phenotypic properties. Alternatively, specific binding partners displaying phenotypic enhancements for the desired trait can be enriched from unwanted specific binding partners using a reporter system as described in Section VI to identify desired specific binding partners and enable subsequent separation from unwanted specific binding partners. A preferred, but not limiting, embodiment uses fluorescence-activated cell sorting ("FACS"), in conjunction with fluorescently labeled sample, to selectively identify and isolate specific binding partners with desired phenotypic enhancements. Unlabeled sample can also be used to identify and isolate specific binding partners with desired phenotypic enhancements in conjunction with FACS if a second fluorescently labeled reagent capable of binding to a non-overlapping epitope on the sample is available. Typically, the enriched clones with the enhanced phenotypic trait are amplified and the selection process is repeated for further enrichment and refinement.

After multiple rounds of selection as described above, the $K_D$, $k_d$, $k_a$ or functional activity of the specific binding partners which have formed the specific binding partner-analyte complexes can be determined using routine techniques known in the art. For example, the $K_D$, $k_d$ or $k_a$ can be determined using KinExA® or Biacore® assays. Methods for determining the functional activity of a specific binding partner are also well known in the art and include, but are not limited to, KinExA® and Biacore® assays, radioimmunoassays, enzyme immunoassays, chemiluminescent immunoassays, fluorescence correlation spectroscopy, fluorescent-activated cell sorting, fluorescence-activated cell sorting or fluorescence polarization immunoassay. The specific binding partner that exhibits the best $K_D$, $k_d$ or $k_a$ or functional activity in binding to the analyte when compared to the other specific binding partners tested is deemed to be improved and allows for a specific binding partner to be selected for further development, such as for use in an diagnostic immunoassay.

Now by way of example, and not of limitation, examples of the present invention shall now be given.

Example 1

Identification of Immunoglobulin Genes

Messenger RNA was isolated from anti-tacrolimus 1-60-46 hybridoma cells using commercially available kits. 1-60-46 mRNA was utilized in a reverse transcriptase-polymerase chain reaction using a mouse Ig primer set kit purchased from Novagen (Novagen (which is an Affiliate of Merck KGaA, Darmstadt, Germany), Cat No. 69831-3) with immunoglobulin gene specific primers contained in the kit. The resulting PCR products were sequenced and the immunoglobulin variable heavy and variable light chain genes were identified (See FIGS. 2, 6, and 7A-7B and SEQ ID NOS:1-14, 43 and 45).

Example 2

Conversion of Tacrolimus 1-60-46 mAb into Single-Chain Antibody Fragment (scFv)

A yeast display system was used to express unmutated (wild-type ("wt")) anti-tacrolimus proteins (described herein infra) and a library of anti-tacrolimus proteins on the yeast surface as a fusion to the yeast mating protein, AGA2 (See, Boder and Wittrup, *Nature Biotechnology,* 15:553-557 (June 1997)). PCR single overlap extension ("SOE") was used to combine the variable heavy ("VH") and the variable light genes ("VL") via a flexible linker having the sequence GPAKELTPLKEAKVS (SEQ ID NO:36) to create the WT 1-60-46 scFv construct (See, FIG. 1). The 1-60-46 VH gene (SEQ ID NO:43) was amplified using primers Tacro scFv VH forward-(GCGGCCCAGCCGGCCATGGCCGAGGTGGAATTGGTGGAGTCTGGG (SEQ ID NO:47)) and Tacro scFv VL reverse (CGCCTCCTTCAGGGGCGTCAACTCCTTGGCGGGACCTGCAGAGACAGTGACCAGAGTCCC (SEQ ID NO:48)). The 1-60-46 VL gene (SEQ ID NO:45) was amplified using primers Tacro scFv VL forward-(AAGGAGTTGACGCCCCTGAAGGAGGCGAAGGTCTCTGATGTTTTGATGACCCAAACTCCA (SEQ ID NO:49)) and Tacro scFv VL reverse-(AGACTCGAGGGCGGCCGCCCGTTTCAGCTCCAGCTTGGTCCC (SEQ ID NO:50)). The 1-60-46 scFv DNA was subsequently cloned into the yeast display vector pYD1 (Invitrogen, Carlsbad, Calif.) using standard molecular biology techniques. This vector includes a galactose inducible promoter, a C-terminal V5 epitope tag, and tryptophan and ampicillin markers for EBY100 and *E. coli* selection, respectively. The tacrolimus WT 1-60-46 scFv_pYD vector was transformed into DH5α *E. coli* and sequence verified.

The tacrolimus WT 1-60-46 scFv_pYD vector was transformed into the tryptophan-deficient *S. cerevisiae* strain EBY100 using Gietz and Schiestl Method (See, Schiestl and Gietz, *Current Genetics,* 16(5-6):339-46 (December 1989)).

Dilutions of the transformation reaction were plated on selective (lacking tryptophan) glucose plates (2% glucose (0.67% yeast nitrogen base, 0.105% Hollenberg Supplement Media ("HSM") -trp (tryptophan) -ura (uracil), 1.8% bacterial agar, 18.2% sorbitol, 0.86% $NaH_2PO_4H_2O$, 1.02% $Na_2HPO_4$ $7H_2O$)) and incubated at 30° C. for 48-72 hours. Selective glucose media was inoculated with individual colonies and grown shaking at 30° C. for 16-20 hours. Protein expression was induced in colonies by transferring 0.5 OD600 of cells/ml ($1\times10^7$ ("1e7cells")/0.5 OD/ml) to selective galactose media. Colonies were shaken at 20° C. for 16-24 hours and then analyzed by flow cytometry for binding to tacrolimus antigen with a biotin group attached to position 32 of the molecule (referred to as "bt-tacro") (Abbott Laboratories, Abbott Park, Ill.) and anti-V5 monoclonal antibody (Invitrogen, Carlsbad, Calif.). For flow cytometry assays, yeast cells expressing 1-60-46 scFv were incubated with bt-tacro and anti-V5 monoclonal antibody followed by streptavidin: phycoerythrin (SA:PE, BD Pharmingen) and goat anti-mouse immunoglobulin-Alexa Fluora 488 (GAM:488, Molecular Probes (which is an Affiliate of Invitrogen, Carlsbad, Calif.)). The bivariate plots of the flow cytometric data as shown in FIG. 1C illustrate full-length surface expression of 1-60-46 scFv (anti-V5) and binding (SA:PE) of 1-60-46 scFv to bt-tacro.

Example 3

Dissociation Rate Analysis for 1-60-46 scFv on Yeast

Dissociation rate measurements of 1-60-46 scFv and 1-60-46 variants on yeast were measured by saturating 0.05 OD yeast ($1\times10^6$ cells) with 100 nM bt-tacro (10-fold molar excess) and anti-V5 antibody (2.5 ug/ml) for 30-60 minutes at room temperature. Reactions were performed in: (a) a physiological diluent (composed of phosphate buffered saline ("PBS"), pH 7.4 and 1% bovine serum albumin ("BSA"); and (b) a selection diluent (composed of PBS, BSA and 10% methanol). Cells were then washed twice and incubated at room temperature with 100-fold molar excess unlabelled tacrolimus (Astellas Pharma, Inc., Tokyo, Japan) in the appropriate diluent (the physiological diluent or the selection diluent described above). Individual samples were withdrawn at various time points and analyzed by flow cytometry to determine the amount of bound bt-tacro remaining after addition of secondary staining reagents, SA:PE (1:200 dilution) and GAM:488 (1:100 dilution). FIG. 1D shows the dissociation rate data plotted as mean fluorescence intensity ("MFI") versus time (seconds) (See, FIG. 1D). A first order exponential decay equation (y=m1*exp(−m2*m0)+m3) was used to fit the data. The dissociation for the WT 1-60-46 scFv was determined to be $1\times10^{-4}$ ($\pm2\times10^{-5}$)/sec without 10% methanol and $9\times10^{-4}$ ($\pm2\times10^{-4}$)/sec with 10% methanol. The 1-60-46 scFv half-life ($t_{1/2}=\ln^2/k_{off}$)) was 115 min in the absence of 10% methanol and 13 minutes in the presence of 10% methanol.

Example 4

Generation of 1-60-46 CDR Mutagenic Libraries

Figure 3:
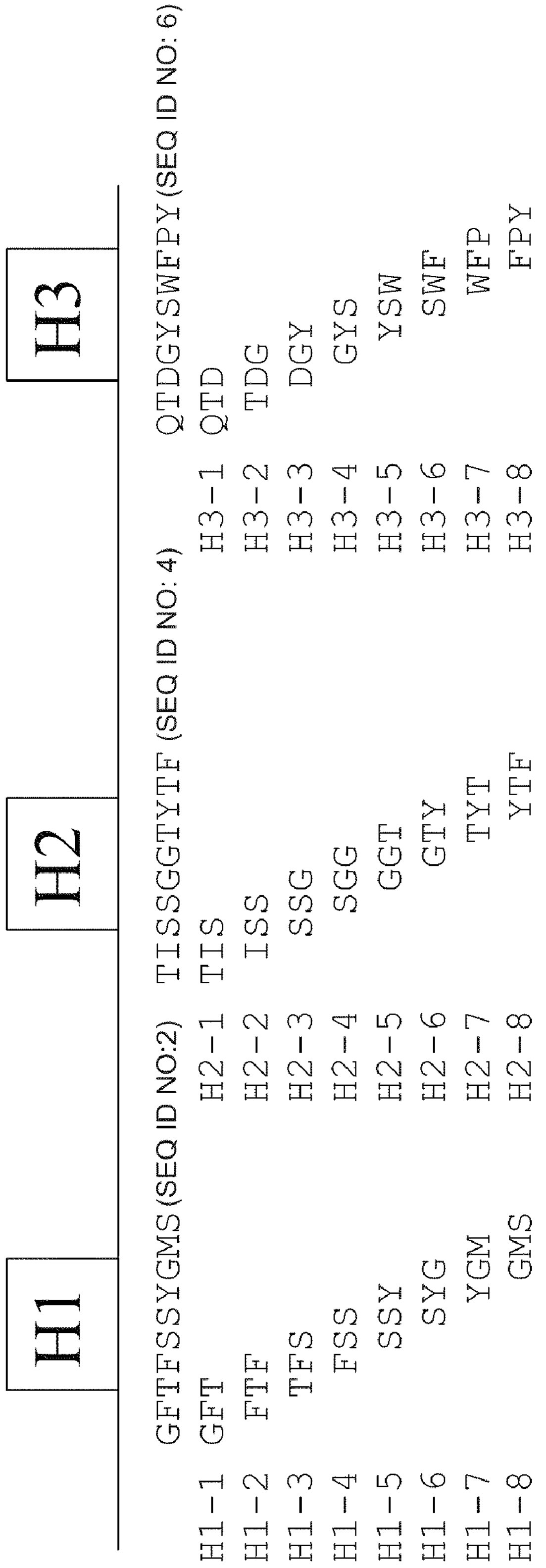
FIG. 3 shows a schematic representation of tacrolimus 1-60-46 VH complementary determining region ("CDR") mutagenic libraries. Libraries names are denoted to the left of each of the 3 amino acid sequences (i.e., SEQ ID NO: 2, SEQ ID NO: 4, and SEQ ID NO: 6) subjected to randomization. The amino acid sequences of the tacrolimus 1-60-46 VH CDRs are shown below each CDR.
Figure 4:
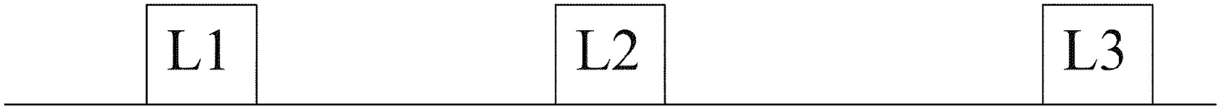
FIG. 4 shows a schematic representation of tacrolimus 1-60-46 VL CDR mutagenic libraries. Libraries names are denoted to the left of each of the 3 amino acid sequences (i.e., SEQ ID NO: 93, SEQ ID NO: 11, and SEQ ID NO: 13) subjected to randomization. The amino acid sequences of the tacrolimus 1-60-46 VL CDRs are shown below each CDR.

All 6 CDRs of anti-tacrolimus antibody 1-60-46 (See, FIGS. 3, 4, 6, and 7A-7B and SEQ ID NOS:2, 4, 6, 9, 11 and 13) were subjected to mutagenesis. Individual libraries composed of 8000 members, in which 3 successive CDR amino acid positions are randomly mutated, were generated (See, FIGS. 3 and 4). It is to be understood that the specific designation of CDR regions within a particular heavy or light chain variable region may vary depending on the convention or numbering system used to identify such regions (e.g., Chothia, Kabat, Oxford Molecular's AbM modeling software, IMGT V-quest, all of which are known to those of ordinary skill in the art). Such designations, however, are not critical. Linearized pYD1 vectors missing specific regions of each CDR were prepared by PCR and the "gap" was replaced by a degenerate single-stranded oligonucleotide, encoding all 19 amino acid possible replacements within the 3 amino acids mutagenic window in the CDR being targeted, using the homologous recombination system inherent in yeast using the Gietz library transformation protocol (See, Schiestl and Gietz, *Current Genetics,* 16(5-6):339-46 (December 1989)). Transformed yeast cells were selectively recovered using the auxotrophic tryptophan marker present on reconstituted vectors. A total of 50 libraries were generated and are schematically represented in FIGS. 3 and 4.

Example 5

Selection of 1-60-46 Mutagenic Libraries

A dissociation rate sorting strategy was used to identify 1-60-46 variants from all 50 mutagenic libraries with improved binding characteristics in a selection diluent (composed of PBS, 1% BSA and 10% methanol). Individual libraries within each CDR region were pooled prior to selection (e.g., H1 libraries 1-8 were combined to generate a H1 master library); however, each CDR master library was kept separate from one another during the selection process. The 1-60-46 mutagenic libraries were first saturated with bt-tacro in the selection diluent at room temperature for 20 minutes and chilled on ice for 10 minutes. Cells were washed and then incubated at room temperature with 100-fold molar excess for 65-72 minutes (5×WT scFv $t_{1/2}$) in the selection diluent in order to select for variants with improved binding relative to the parental wt 1-60-46 scFv. After the dissociation incubation, the cell were again chilled, washed, and labeled. The amount of the bt-tacro antigen remaining on each individual cell was detected using SA:PE (1:200 dilution). Antigen binding was normalized to the amount of scFv expression on each individual cell using anti-V5 mAb (2 ug/ml) and GaM-488 (1:100 dilution). Control samples were prepared to set fluorescence compensation and monitor non-specific binding. Samples incubated in a physiological diluent (composed of PBS, pH 7.4 and 1% BSA) were also prepared for comparison. Populations of variants with desired binding properties were selectively enriched using fluorescence-activated cell sorting ("FACS") on a FACSAria cell sorter (Becton Dickinson, San Jose, Calif.).

Figures 5A, 5B, 5C:
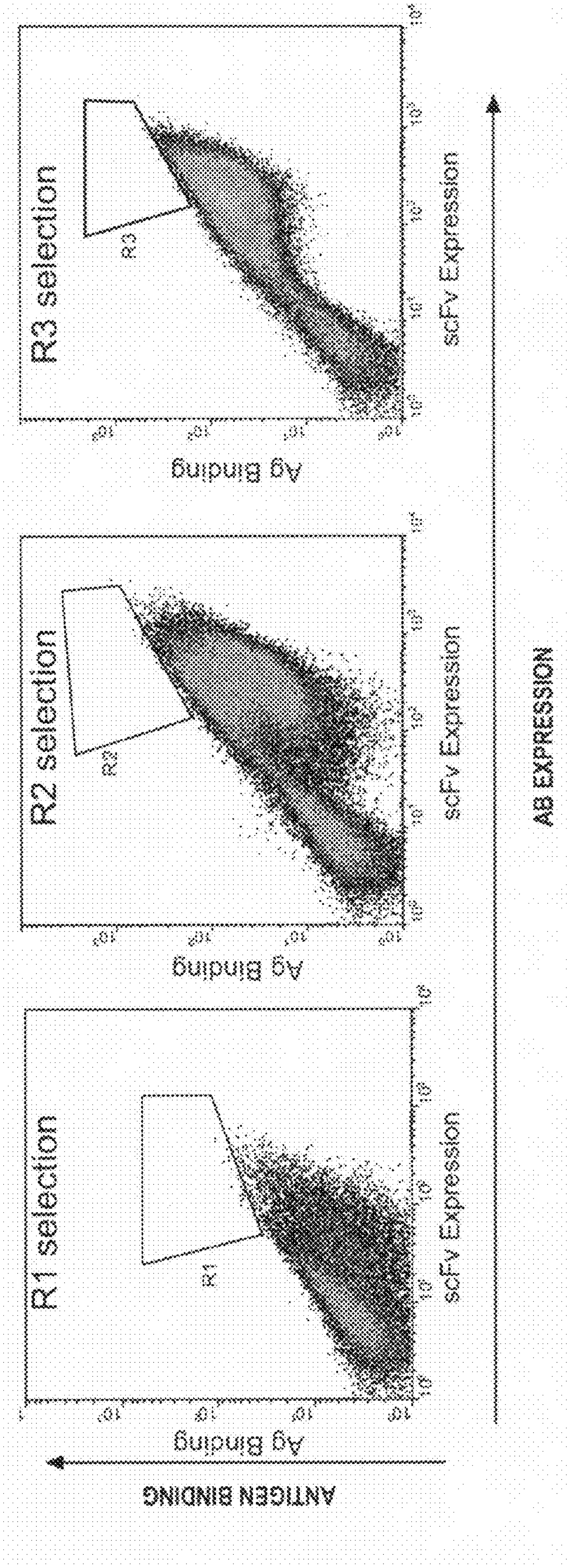
FIGS. 5A-5C show bivariate plots of a representative tacrolimus 1-60-46 mutagenic CDR library during 3 rounds of selection. ScFv expression is denoted on the X-axis and is plotted against antigen-binding which is shown on the Y-axis. Representative sort gates isolated the brightest 0.1%-1.0% of antigen-binding clones and these are shown in each plot.

Three rounds of selection were performed on each library sample with a representative library are shown in FIG. 5. Each round of selection consisted of selectively gating 0.1%-1% of cells with the highest degree of fluorescence in the SA:PE (antigen-binding) channel plotted against the scFv expression signal. Selected cells were collected, and re-grown in media containing dextrose (selection round output), which inhibits expression from the galactose promoter thereby preventing scFv expression, at 30° C. for 2-3 days. An aliquot from each library would be removed for each round output for preservation. The output was then induced for scFv expression with media containing galactose at 20° C. for 12-24 hrs and the selection process was repeated. Libraries containing mutations that decreased the dissociation rate in the selection diluent became progressively brighter throughout each round of selection (H2, L1 and L3), whereas libraries lacking beneficial changes did not and were not further analyzed. An aliquot of cells after the third round of sorting were plated on selective media to obtain individual clones for further analysis.

Example 6

Analysis of Selected 1-60-46 Variants

PCR was used to amplify the scFv region from a number of individual clones from each master CDR library (H2, L1 and L3) that showed improvements in binding to bt-tacro in a selection diluent (composed of PBS, 1% BSA and 10% methanol) from the selection above. The scFv genes were amplified and sequenced using vector specific primers (pYD41 forward-TAGCATGACTGGTGGACAGC (SEQ ID NO:37) and pYD41reverse-CGTAGAATCGAGACCGAG (SEQ ID NO:38)) to identify the amino acid substitutions. FIGS. 6 and 7 highlight the sequencing results for each unique clone obtained.

Each unique clone was induced for scFv expression and the binding properties of the selected mutant scFv were assessed using flow cytometry. The dissociation rate ($k_{off}$) for each mutant was determined as outlined above in both the presence and absence of 10% methanol during the reaction (See, FIG. 8). All mutant clones had 2- to 8-fold improvements in $k_{off}$ relative to the WT 1-60-46 scFv in both reaction conditions with the best clone (L3-1A) having a dissociation rate of $1.2\times10^{-4}$/sec in 10% methanol.

Those clones that had the greatest improvement in dissociation rate from each master CDR library were further characterized. Equilibrium dissociation constants ($K_D$) for bt-tacro antigen were determined in both (a) a physiological diluent (composed of PBS, pH 7.4 and 1% BSA); and (b) a selection diluent (composed of PBS, 1% BSA and 10% methanol). Yeast clones induced for scFv expression were mixed with various concentrations of bt-tacro (range of antigen concentration) and allowed to reach equilibrium (4-18 hrs) in the appropriate diluent. Reactions were quenched on ice, washed, and labeled for flow cytometric measurement as described previously (See, for example, Hawley and Hawley, eds., *Methods in Molecular Biology: Flow Cytometry Protocols,* 2nd ed., Humana Press, Totowa, N.J., pages 311-332 (2004)). The antibody-normalized, antigen-binding mean fluorescence intensity was plotted against antigen concentration and a non-linear least squares fit (y=m1+m2*m0/(m3+m0)) was used to determine $K_D$. Mutants contained 2- to 8-fold improvements relative to the WT 1-60-46 scFv with the highest affinity clone (H2-1A) having a $K_D=1.3\times10^{-10}$ M in 10% methanol.

Example 7

Generation and Analysis of Tacrolimus 1-60-46 Combinatorial Mutant Clones

Clones having the greatest improvement in dissociation rate from each master CDR library were used to construct scFv genes containing different pairings of the individual mutations. This approach enabled determination of whether the binding properties were further enhanced upon combining individual mutations. Combinatorial clones containing various mutations in the H2 (H2-1A, H2-1B, H2-3B), L1 (L1-1B, L1-4A) and L3 (L3-A, L3-1A, L3-2A, L3-1B, L3-2B) CDR regions were constructed by PCR amplification and combined using routine techniques known to those skilled in the art. Combinatorial mutant clones were sequence-verified, and transformed into yeast as described above for further characterization. Each combinatorial mutant clone was induced for scFv expression (as previously described herein) and the binding properties were assessed using flow cytometry.

Figure 9B:
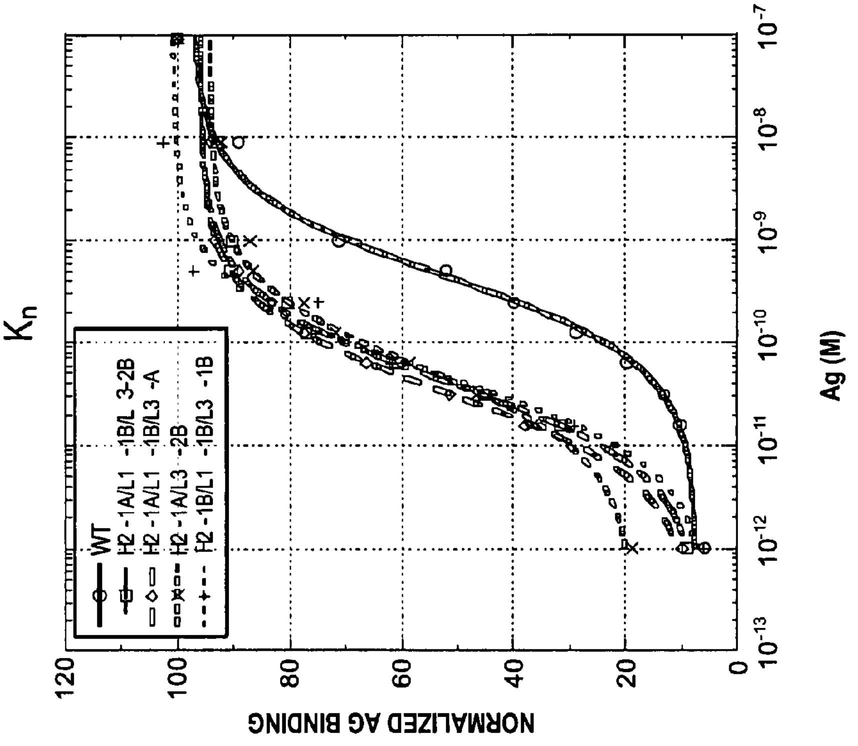
FIGS. 9A-9B show an affinity analysis of tacrolimus 1-60-46 WT scFv and the combinatorial mutant clones (H2 1A/L1-1B/L 3-2B, H2-1A/L1-1B/L3-A, H2-1A/L3-1B and H2-1B/L1-1B/L3-1B) in a selection diluent (composed of PBS, 1% BSA and 10% methanol).
Figure 9A:
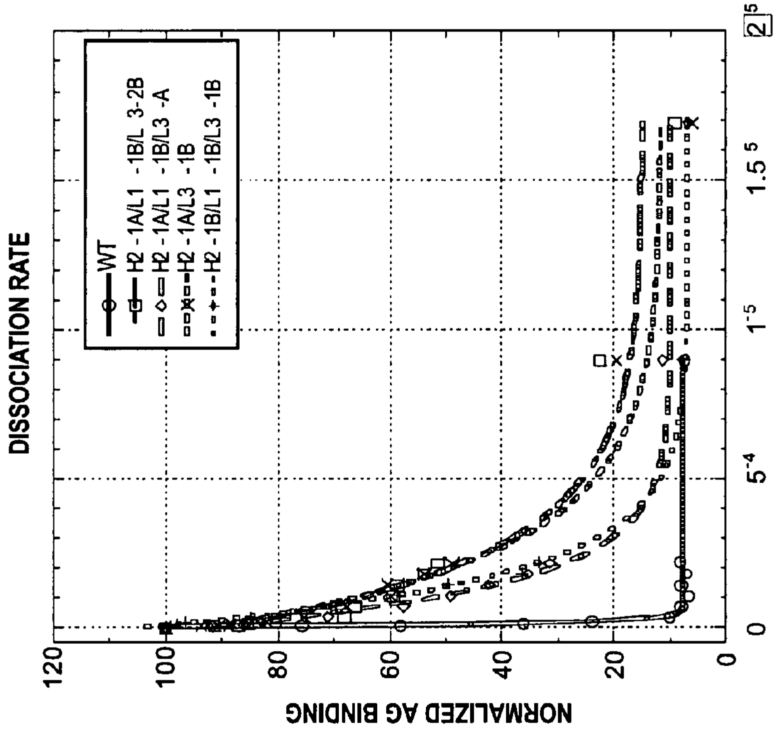

The dissociation rate for each clone was determined with a selection diluent (composed of PBS, 1% BSA and 10% methanol). Additionally, several clones were also analyzed in a physiological diluent (composed of PBS, pH 7.4 and 1% BSA) (See, FIGS. 8 and 9). Many of the tacrolimus 1-60-46 combination mutant clones exhibited greater than 10-fold improvements in $k_{off}$ with the best clone (H2-1A/L3-1A) having a dissociation rate of $5.5\times10^{-5}$/sec in 10% methanol, a substantial improvement relative to any of the original tacrolimus 1-60-46 mutations, in general, and the WT 1-60-46 clone, in particular. Equilibrium dissociation constants for bt-tacro antigen were also determined in the selection diluent as previously described. Most combinatorial pairings of mutations show improved affinities relative to both the original tacrolimus 1-60-46 mutations and the WT 1-60-46 clone (See, FIGS. 8 and 9). The clone H2-1A/L1-1B/L3-A had a $K_D$ of $3.8\times10^{-11}$ M.

Example 8

Cloning and Expression of Yeast Display-Derived Antibodies

Select tacrolimus 1-60-46 mutant scFv clones (See, FIG. 10) were converted into murine Ig2a/κ antibodies (IgG) by PCR amplification of the variable domains, followed by ligation of these domains to an intact IgG2a constant region or K region present in the pBOS vector (Mizushima and Nagata, *Nucleic Acids Research,* 18:5322, (1990)). Select 1-60-46 mutant VH genes were amplified by PCR using Tacro VH IgG2a forward-(TTCTTGTCGCGATTTTAAAAGGTGTCCAGTGCGAGGTGGAATTGGTGGAGTCT (SEQ ID NO:51)) and Tacro VH IgG2a reverse-(TGTTTTAGCGCTTGCAGAGACAGTGACCAGAGT (SEQ ID NO:52)). Select 1-60-46 mutant VL genes were amplified by PCR using Tacro VL mCk forward-(CCCGGCTCGCGATGCGATGTTTTGATGACCCAAACT (SEQ ID NO:53)) and Tacro VL Ck reverse-(AGCATCAGCGCTCGCCCGTTTCAGCTCCAGCTT (SEQ ID NO:54)). pBOS plasmids encoding both heavy and light chain regions were transiently transfected into HEK-293 or COS cells and the resulting supernatants from cell cultures were purified over a protein A Sepharose column. Tacrolimus 1-60-46 AM1 IgG contains the H2-1A, L1-1B and L3-2B mutations. Tacrolimus 1-60-46 AM2 IgG contains the H2-1A, L1-1B and L3-A mutations. Tacrolimus 1-60-46 AM3 IgG contains the H2-1A and L3-2B mutations. Tacrolimus 1-60-46 AM4 IgG contains the H2-1A, L1-1B and L3-1A mutations. Tacrolimus 1-60-46 AM5 IgG contains the H2-1B, L1-1B and L3-1B mutations. Purified IgG were dialyzed into phosphate buffered saline ("PBS") and quantitated by measuring absorbance at 280 nm. Purified antibodies were then evaluated by assay performance and affinity measurements.

Example 9

Tacrolimus 1-60-46 Mutant IgG Immunoassay Evaluation

The affinity-matured anti-tacrolimus antibodies (AM1, AM2, AM3) were individually immobilized to goat anti-mouse IgG ("GAM") coated paramagnetic microparticles. To prepare these particles, the GAM was coupled covalently to the particles, and then the particles were combined with a buffering and stabilizing solution containing the anti-tacrolimus antibody. The GAM and the anti-tacrolimus formed a stable complex on the microparticle surface. These anti-tacrolimus-GAM-paramagnetic microparticles were tested in an automated tacrolimus assay using a competitive format on the ARCHITECT® instrument (Abbott Laboratories, Abbott Park, Ill.).

In the assay, the instrument mixes the test sample containing the assay extraction buffer (namely 90% methanol, 10% ethylene glycol and 100 mM zinc sulfate) with the microparticles and a tracer reagent. The tracer molecule contains tacrolimus attached covalently to acridinium through a linker at position 32 (Abbott Laboratories, Abbott Park, Ill.). The tracer and tacrolimus from the sample compete for the limited number of anti-tacrolimus binding sites on the microparticles. After an incubation period, the microparticles are attracted to a magnet, and then washed to remove unbound materials. The instrument then adds triggering solutions to initiate chemiluminescence in the acridinium portion of the bound tracer. The chemiluminescence is measured by a photometer; the amount of chemiluminescence signal is inversely proportional to the amount of tacrolimus in the sample.

The ability of the assay to detect low concentrations of tacrolimus is related directly to the ability of tacrolimus to displace the tracer from the anti-tacrolimus antibody, which in turn, is directly related to the affinity of the antibody for the drug. The results in FIG. 10 show that, with the wildtype antibody, a sample with a tacrolimus concentration of 3 ng/mL was able to displace approximately 40% of the tracer. For the three affinity-matured antibodies (AM 1-3), the same 3 ng/mL tacrolimus sample produced 78-80% displacement. This greater displacement will allow the detection of lower tacrolimus concentrations using the recombinant antibody.

Example 10

Affinity Determination of Tacrolimus 1-60-46 Mutant IgG Antibodies

The equilibrium dissociation constants for both the 1-60-46 AM2 IgG and the 1-60-46 WT mAb IgG produced from the murine hybridoma cell line 1-60-46 were determined using Kinetic Exclusion Assay (KinExA®), available from Sapidyne Instruments (Boise, Id.) (See, Darling and Brault, *ASSAY and Drug Development Technologies,* 2(6):647-657 (2004)). A constant amount of IgG antibody (AM2 or WT) was incubated with various concentrations ($10^{-8}$ M to $10^{-13}$ M) of tacrolimus drug (commercially available from Astellas Pharma, Inc., Tokyo, Japan) and allowed to come to equilibrium (2 hours to 14 hours) before sampling. The amount of free binding sites was determined by injecting the antibody: tacrolimus reaction mixture over bt-tacro immobilized to a solid-phase. Tacrolimus IgG antibody bound to the bt-tacro immobilized to the solid-phase was subsequently detected by injecting goat anti-mouse polyclonal antibody conjugates (GAM) to Cy5 (GAM-Cy5) fluorescent dye. The degree of GAM-Cy5 bound was proportional to the amount of tacrolimus IgG bound to the immobilized bt-tacro and was detected after excitation with the appropriate wavelength. The $K_D$ was determined by analyzing the amount of free binding sites versus the amount of antigen present in the reaction sample using software provided by the manufacturer (Sapidyne Instruments; Boise, Id.). Experiments were performed in either (a) a physiological diluent (composed of PBS, pH 7.4 and 1% BSA); and (b) a selection diluent (composed of PBS, 1% BSA and 10% methanol) and the results are summarized below in Table B. The $K_D$ of the 1-60-46 AM2 IgG in the physiological diluent was $1.2\times10^{-12}$ M, which is a 16-fold improvement relative to the 1-60-46 WT IgG value of $1.9\times10^{-11}$ M. The $K_D$ of the 1-60-46 AM2 IgG in the selection diluent was $1.3\times10^{-11}$ M which is a 12-fold improvement relative to the 1-60-46 WT IgG value of $1.5\times10^{-10}$ M.

TABLE B

| | KD (no MeOH) | Fold Improvement | Kd (10% MeOH) | Fold Improvement |
|---|---|---|---|---|
| 1-60-46 WT IgG | $1.9\times10^{-11}$ M | 1x | $1.52\times10^{-10}$ M | 1x |
| 1-60-46 AM2 IgG | $1.2\times10^{-12}$ M | 16x | $1.3\times10^{-11}$ M | 12x |

Example 11

Tacrolimus 1-60-46 AM2 IgG Stable Mammalian Cell Line Development

Chinese Hamster Ovary cells were transfected with a plasmid containing Tacrolimus 1-60-46 AM2 IgG heavy chain ("HC") (See, FIG. 11 (SEQ ID NO:39)) and IgG light chain ("LC") (FIG. 12 (SEQ ID NO:41)) gene sequences using techniques known to those skilled in the art. Stable cell lines were identified after restoration of dihydrofolate reductase function in media lacking certain nutrients (See, Urlaub et al., *Cell,* 33:405-412 (1983)). A Chinese Hamster Ovary cell line designated tacrolimus 1-60-46 AM 2 CHO 2-577 was deposited with the American Type Culture Collection ("A.T.C.C") (Manassas, Va.) in accordance with the Budapest Treaty on Mar. 15, 2006 and assigned A.T.C.C. Accession No. PTA-7436. A Chinese Hamster Ovary cell line designated tacrolimus 1-60-46 AM 2 CHO 1-1157 was deposited with A.T.C.C (Manassas, Va.) in accordance with the Budapest Treaty on Mar. 27, 2006 and assigned A.T.C.C. Accession No. PTA-7446.

Example 12

Identification of Anti-Cyclosporine ("CsA") Hybridoma 29-56-14 Immunoglobulin Genes and Conversion into Single-Chain Antibody Fragment (scFv)

FIG. 16 shows the structure of CsA and a metabolite of CsA, which is referred to herein as "AM1 or M17". CsA and its metabolites are described in detail in Kahan et al., "Consensus Document: Hawk's Cay Meeting on Therapeutic Drug Monitoring of Cyclosporine," *Clin. Chem.,* 36/8:1510-1516 (1990), which is herein incorporated by reference.

Immunoglobulin genes for CsA were identified and converted into scFv using the procedures described in Examples 1 and 2. Messenger RNA was isolated from anti-CSA 29-56-14 mouse hybridoma cells (Novartis, Basel, Switzerland) using commercially available kits. 29-56-14 hybridoma mRNA was utilized in a reverse transcriptase-polymerase chain reaction using a mouse Ig primer set kit purchased from Novagen (Novagen (which is an Affiliate of Merck KGaA, Darmstadt, Germany), Cat No. 69831-3) with immunoglobulin gene specific primers contained in the kit. The resulting PCR products were sequenced and the immunoglobulin variable heavy and variable light chain genes were identified (See FIGS. 13A and 13B).

Figure 1D:
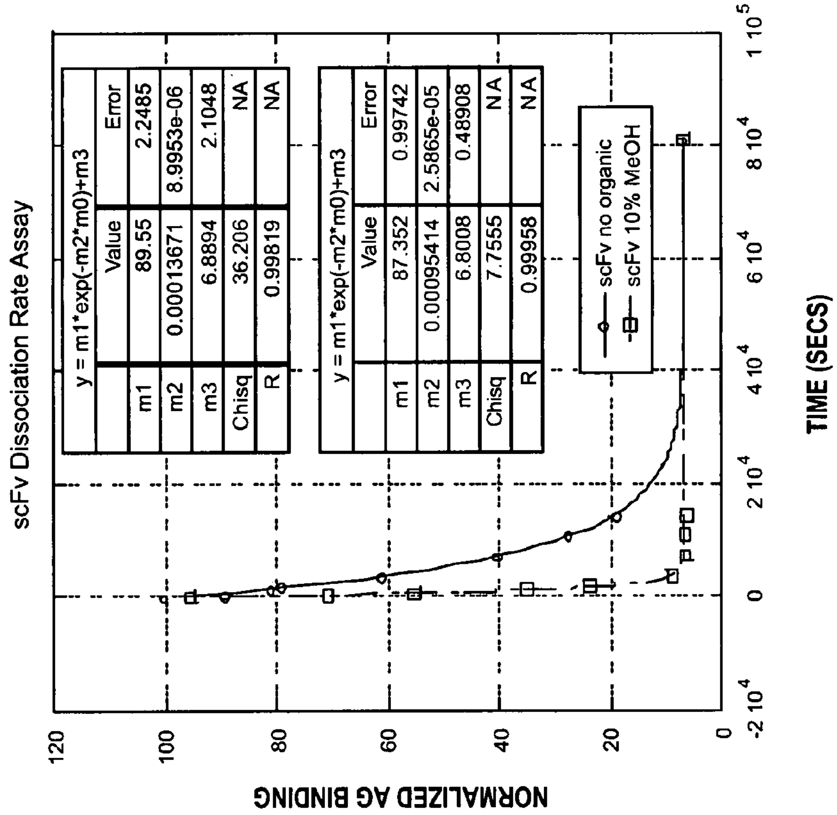
FIG. 1D shows a tacrolimus WT 1-60-46 scFv flow cytometric dissociation rate assay plot.
Figure 1C:
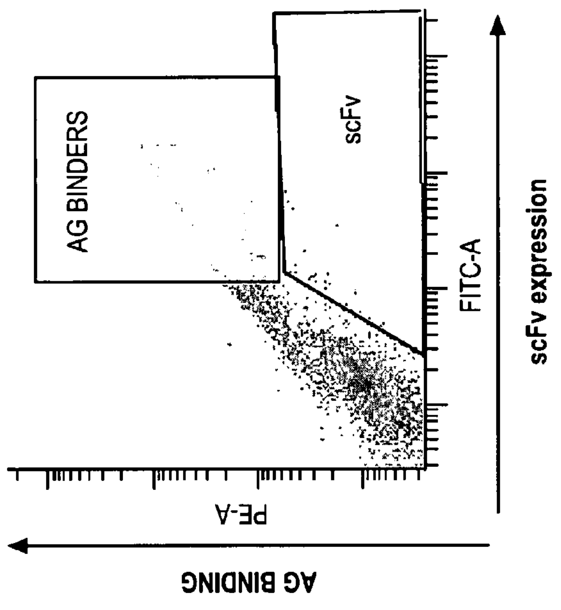
FIG. 1C shows a bivariate plot showing scFv expression versus antigen binding by wildtype ("WT") 1-60-46 scFv yeast as determined by a flow cytometric assay.

A yeast display system was used to express unmutated (wild-type ("WT")) and mutated anti-cyclosporine variable light and heavy chain proteins on the yeast surface as a fusion to the yeast mating protein, AGA2 (See FIG. 1B and Boder and Wittrup, *Nature Biotechnology,* 15:553-557 (June 1997)). PCR single overlap extension ("SOE") was used to combine the variable heavy ("VH") and the variable light genes ("VL") via a flexible linker having the sequence GPAKELTPLKEAKVS (SEQ ID NO:36) to create the WT Cyclosporine 29-56-14 scFv construct.

The 29-56-14 VH gene (FIG. 13A, SEQ ID NO:55) was amplified using the following primers: CsA scFv VH forward-GGCCCAGCCGGCCATGGCCGAGGTCCAGCTGCAACAGTCTGG (SEQ ID NO:59)

```
CsA scFv VH forward -
                                        (SEQ ID NO: 59)
GGCCCAGCCGGCCATGGCCGAGGTCCAGCTGCAACAGTCTGG

CsA scFv VH 40 reverse-
                                        (SEQ ID NO: 60)
CTTCGCCTCCTTCAGGGGCGTCAACTCCTTGGCGGGACCTGAGGAGACGG

TGACTGAGGTTCC
```

The 29-56-14 VL gene (FIG. 13B, SEQ ID NO:57) was amplified using primers:

```
CsA scFv VL 40 forward -
                                        (SEQ ID NO: 61)
CAAGGAGTTGACGCCCCTGAAGGAGGCGAAGGTCTCTGACATTGTACTGA

CCCAATCTCC

CsA scFv VL reverse -
                                        (SEQ ID NO: 62)
TCTAGACTCGAGGGCGGCCGCCCGTTTGATTTCCAGGTTGGTGC.
```

The 29-56-14 scFv DNA was subsequently cloned into the yeast display vector pYD1 (Invitrogen, Carlsbad, Calif.) using standard molecular biology techniques. This vector includes a galactose inducible promoter, a C-terminal V5 epitope tag, and tryptophan and ampicillin markers for EBY100 and *E. coli* selection, respectively. The cyclosporine WT 29-56-14 scFv_pYD vector was transformed into DH5α *E. coli* and sequence verified.

The cyclosporine WT 29-56-14 scFv_pYD vector was transformed into the tryptophan-deficient *S. cerevisiae* strain EBY100 using Gietz and Schiestl Method (See, Schiestl and Gietz, *Current Genetics,* 16(5-6):339-46 (December 1989)). Dilutions of the transformation reaction were plated on selective (lacking tryptophan) glucose plates (2% glucose (0.67% yeast nitrogen base, 0.105% Hollenberg Supplement Media ("HSM")-trp (tryptophan)-ura (uracil), 1.8% bacterial agar, 18.2% sorbitol, 0.86% $NaH_2PO_4H_2O$, 1.02% $Na_2HPO_4$ $7H_2O$)) and incubated at 30° C. for 48-72 hours. Selective glucose media was inoculated with individual colonies and grown shaking at 30° C. for 16-20 hours. Protein expression was induced in colonies by transferring 0.5 OD600 of cells/ml ($1\times10^7$ ("1e7cells")/0.5 OD/ml) to selective galactose media. Colonies were shaken at 20° C. for 16-24 hours and then analyzed by flow cytometry for binding to cyclosporine antigen with a biotin group attached to position 1 of the cyclic undecapeptide (referred to as "bt-CsA") and anti-V5. For flow cytometry assays, yeast cells expressing 29-56-14 scFv were incubated with bt-CsA and anti-V5 antibody followed by streptavidin: phycoerythrin (SA:PE, BD Pharmingen) and goat anti-mouse immunoglobulin-Alexa Fluora 488 (GAM: 488, Molecular Probes (which is an Affiliate of Invitrogen, Carlsbad, Calif.)). Bivariate plots of flow cytometric data similar to those shown in FIG. 1C were obtained to illustrate full-length surface expression of 29-56-14 scFv (anti-V5) and binding (SA:PE) of 29-56-14 scFv to bt-CsA.

Example 13

Affinity Measurement for CsA of 29-56-14 scFv Expressed on Yeast Cells

Equilibrium dissociation constant ($K_D$) for bt-CsA antigen was determined in a physiological diluent (composed of PBS, pH 7.4 and 1% BSA). Yeast clones induced for scFv expression were mixed with various concentrations of bt-CsA and allowed to reach equilibrium (4-18 hrs) in either (a) a physiological diluent (composed of PBS, pH 7.4 and 1% BSA); and (b) a selection diluent (composed of PBS, 1% BSA and 10% methanol), chilled on ice, washed, and labeled for flow cytometric measurement. The antibody-normalized, antigen-binding mean fluorescence intensity was plotted against antigen concentration and a non-linear least squares fit (y=m1+m2*m0/(m3+m0)) was used to determine $K_D$. WT CsA 29-56-14 scFv $K_D$ was $5.6\times10^{-10}$M in the physiological diluent and $2.0\times10^{-9}$M in the selection diluent. The $K_D$ value for bt-CsA was used for screening of mutagenic libraries in the presence of excess competitor.

Example 14

Generation of 29-56-14 CDR Mutagenic Libraries

All 6 CDRs of anti-cyclosporine antibody 29-56-14 were subjected to mutagenesis using the procedure described previously in Example 4. Individual libraries composed of 8000 members, in which 3 successive CDR amino acid positions are randomly mutated. Linearized pYD1 vectors missing specific regions of each CDR were prepared by PCR and the "gap" was replaced by a degenerate single-stranded oligonucleotide, encoding all 19 amino acid possible replacements within the 3 amino acids mutagenic window in the CDR being targeted, using the homologous recombination system inherent in yeast using the Gietz library transformation protocol (Schiestl and Gietz, *Current Genetics,* 16(5-6):339-46 (December 1989)). Transformed yeast cells were selectively recovered using the auxotrophic tryptophan marker present on reconstituted vectors. A total of 53 CDR mutagenic libraries were generated and individual CDR mutagenic libraries were combined to generate 8 CDR pooled libraries. Individual libraries within each CDR region were pooled prior to selection (e.g. H1 libraries 1-8 were combined to generate a H1 master library); however, each CDR master library was kept separate from one another during the selection process.

Example 15

Selection of 29-56-14 Mutagenic Libraries in the Presence of M17 Competitor

A competitive selection strategy using flow cytometric sorting was used to identify 29-56-14 variants from the 8 pools of CDR mutagenic libraries with improved binding characteristics for bt-CsA in the presence of 20-100 fold molar excess of CsA metabolite (M17). For the initial round of library screening, the 29-56-14 mutagenic libraries were incubated overnight with 1 nM bt-CsA+20 nM M17 in a selection diluent (composed of PBS, 1% BSA and 10% methanol) at room temperature. Cells were washed and the amount of the bt-CsA antigen remaining on each individual cell was detected using SA:PE (1:200 dilution). Antigen binding was normalized to the amount of scFv expression on each individual cell using anti-V5 mAb (2.5 ug/ml) and GaM-488 (1:200 dilution). Control samples were prepared to set fluorescence compensation and monitor non-specific binding. Populations of variants with improved bt-CsA binding were selectively enriched using fluorescence-activated cell sorting (FACS) on a FACSAria cell sorter (Becton Dickinson, San Jose, Calif.).

Four rounds of selection were performed on each library pool with each round of selection consisting of selectively gating 0.1%-0.5% of cells with the highest degree of fluorescence in the SA:PE (antigen-binding) channel plotted against the scFv expression signal. Selected cells were collected, and re-grown in media containing dextrose (selection round output), which inhibits expression from the galactose promoter thereby preventing scFv expression, at 30° C. for 2-3 days. An aliquot from each library would be removed for each round output for preservation. The output was then induced for scFv expression with media containing galactose at 20° C. for 12-24 hrs and the selection process was repeated with 100 nM (100 fold molar excess) of M17 metabolite competitor. Libraries containing mutations that increased the binding of bt-CsA in the presence of M17 competitor became progressively brighter throughout each round of selection. An aliquot of cells after the fourth round of sorting were plated on selective media to obtain individual clones for further analysis.

Example 16

Sequence Analysis of Selected 29-56-14 Variants with Reduced Cross-Reactivity to M17 Metabolite PCR was used to amplify the scFv region from a number of individual clones from each master CDR library (H1, H2, H3-1, H3-2, L1-1, L1-2, L2, and L3) that showed improvements in binding to bt-CsA in the presence of excess M17 metabolite from the selection described in Example 15. The scFv genes were amplified and sequenced using vector specific primers (pYD41 forward-TAGCATGACTGGTGGACAGC (SEQ ID NO:37) and pYD41 reverse-CGTAGAATCGAGACCGAG (SEQ ID NO:38)) to identify the CDR amino acid substitutions.

Example 17

Generation and Analysis of Cyclosporine 29-56-14 Combinatorial Mutant Clones CDR mutant sequences identified after four rounds of flow cytometric selection from each master CDR library were used to construct scFv genes containing different pairings of the individual mutations. Combinatorial clones containing various mutations in the H1, H2, H3, L2, and L3 CDR regions were constructed by PCR amplification and combined using techniques known to those skilled in the art. Combinatorial mutant clones were sequence-verified, and transformed into yeast as described above for additional selection by flow cytometry in the presence of 100 nM (100 fold molar excess) M17 competitor as previously described in Example 15. Only one round of competitive sorting was required to enrich for combinatorial mutant clones with improved specificity for bt-CsA in the presence of M17 metabolite.

Figure 15B:
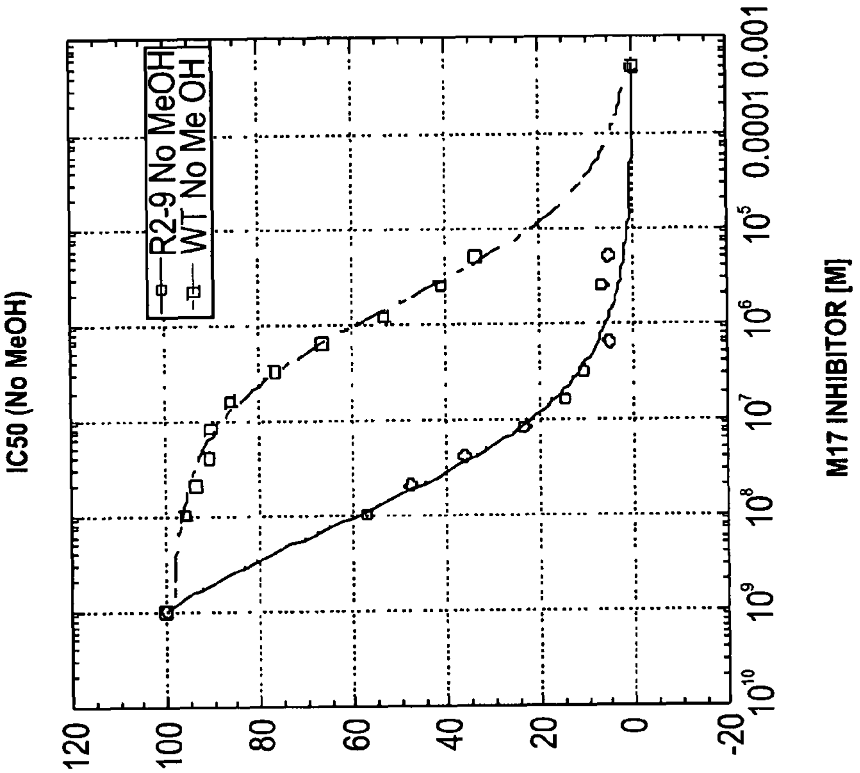
FIGS. 15A and 15B show the IC50 data for 29-56-14 WT and mutant R2-9 yeast clones for bt-CsA binding measured with increasing concentrations of M17 metabolite assayed in either (a) a physiological diluent (composed of PBS, pH 7.4 and 1% BSA); or (b) a selection diluent (composed of PBS, 1% BSA and 10% methanol).
Figure 15A:
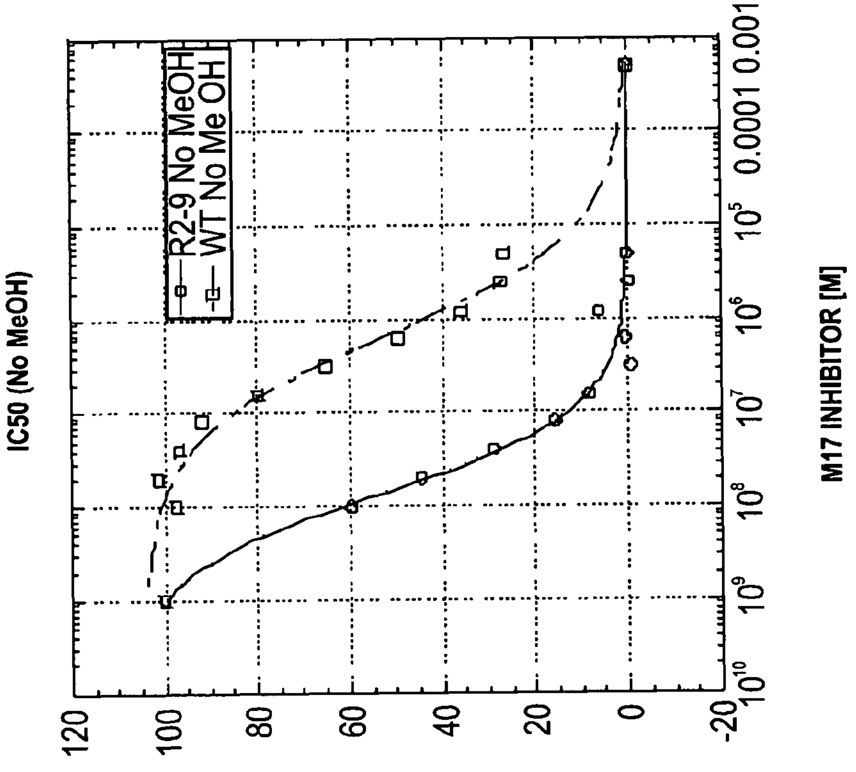

The scFv genes were amplified and sequenced using vector specific primers (pYD41 forward-TAGCATGACTGGTGGACAGC (SEQ ID NO:37) and pYD41 reverse-CGTAGAATCGAGACCGAG (SEQ ID NO:38)) to identify the multiple CDR amino acid substitutions. Sequence analysis identified a population consisting of only four combinations encoding mutations in CDRs H2, H3, L2, and L3 (See FIG. 14). Mutant combinatorial clone R2-9 was selected as the best clone based upon IC50 data. WT and mutant combinatorial clones were incubated overnight with 0.5 nM bt-CsA in the presence of M17 competitor concentrations ranging from 0 to 5 uM. The IC50 data for clone R2-9 tested in either (a) a physiological diluent (composed of PBS, pH 7.4 and 1% BSA); and (b) a selection diluent (composed of PBS, 1% BSA and 10% methanol) is shown in FIG. 15. The mutations encoded in clone R2-9 increase the IC50 for M17 metabolite 30~100 fold compared to WT CsA 29-56-14.

Example 18

Selection of 29-56-14 Mutagenic Libraries in the Presence of M17 and M1 Competitors This example describes a screening method using yeast display to select for CDR (complementarity-determining region) mutations encoded by anti-cyclosporine antibodies that improve selection for cyclosporine parent drug and reduces specificity for major metabolites (lowered cross-reactivity).

The anti-cyclosporine mouse hybridoma 29-56-14 was the model system from which a single chain construct (scFv) comprised of the immunoglobulin heavy and light chains was expressed on the surface of yeast cells. scFv yeast libraries encoding mutations at multiple antigen binding sites utilizing a CDR scanning approach were screened by flow cytometry for improved binding to biotinylated CsA in the presence of 5~200 fold molar excess of AM1 (M17) and AM9 (M1) metabolites together as binding competitors. Distinct yeast clones encoding mutations in several heavy and light chain CDRs were isolated and exhibited up to a 1,000 fold increase of $K_i$ (inhibition constant) for AM1 (M17) and greater than 5 fold $K_i$ for AM9 (M1) compared to CsA wildtype yeast control. Minimal change in the affinity for CsA was observed for the mutants that demonstrated decreased binding for AM1 (M17) and AM9 (M1). These results confirm that the screening approach employed in this and preceding Examples establishes a method by which an antibody with improved specificity for an immunosuppressive agent and more favorable cross-reactivity (lower binding) to metabolites can be developed and ultimately utilized in diagnostic immunoassays.

One skilled in the art would readily appreciate that the present invention is well adapted to carry out the objects and obtain the ends and advantages mentioned, as well as those inherent therein. The compositions, formulations, methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein.

Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A recombinant antibody, which specifically binds to tacrolimus and is expressed from DNA, which is extracted from the Chinese Hamster Ovary cell line 1-60-46 AM2 CHO 2-577 as deposited with the American Type Culture Collection under A.T.C.C. Accession No. PTA-7436.

2. A recombinant antibody, which specifically binds to tacrolimus and is produced by the Chinese Hamster Ovary cell line designated tacrolimus 1-60-46 AM2 CHO 2-577 as deposited with the American Type Culture Collection under A.T.C.C. Accession No. PTA-7436.

3. A recombinant antibody, which specifically binds to tacrolimus and is expressed from DNA, which is extracted from the Chinese Hamster Ovary cell line designated tacrolimus 1-60-46 AM2 CHO 1-1157 as deposited with the American Type Culture Collection under A.T.C.C. Accession No. PTA 7446.

4. A recombinant antibody, which specifically binds to tacrolimus and is produced by the Chinese Hamster Ovary cell line designated tacrolimus 1-60-46 AM2 CHO 1-1157 as deposited with the American Type Culture Collection under A.T.C.C. Accession No. PTA-7446.

5. An isolated recombinant antibody which specifically binds to tacrolimus, wherein said antibody has a variable heavy domain and a variable light domain, the variable heavy domain comprising a heavy chain complementary determining region ("CDR") 1, a heavy chain CDR 2 and a heavy chain CDR 3, the variable light domain comprising a light chain CDR 1, a light chain CDR 2 and a light chain CDR 3, wherein (a) Heavy Chain CDR 1 has an amino acid sequence of: Gly-Phe-Thr-Phe-Ser-Ser-Tyr-Gly-Met-Ser (SEQ ID NO: 2);

(b) Heavy Chain CDR 2 has an amino acid sequence having a formula of: Thr-Ile-Ser-Ser-Gly-Gly-Ala-Trp-Thr-Phe (SEQ ID NO: 16);

(c) Heavy Chain CDR 3 has an amino acid sequence of: Gln-Thr-Asp-Gly-Tyr-Ser-Trp-Phe-Pro-Tyr (SEQ ID NO: 6);

(d) Light Chain CDR 1 has an amino acid sequence having a formula of: Lys-Ser-Ser-Gln-Gly-Leu-Val-His-Ser-Thr-Gly-Asn-Thr-Phe-Leu-Glu (SEQ ID NO: 22);

(e) Light Chain CDR 2 has an amino acid sequence having the formula of: Lys-Ile-Ser-Asn-Arg-Phe-Ser (SEQ ID NO: 11); and (f) Light Chain CDR 3 has an amino acid sequence having a formula of: Phe-Gln-Gly-Ser-His-Ala-Pro-Leu-Thr (SEQ ID NO: 23).

6. An isolated recombinant antibody which specifically binds to tacrolimus, wherein said antibody has a variable heavy domain and a variable light domain, the variable heavy domain comprising a heavy chain complementary determining region ("CDR") 1, a heavy chain CDR 2 and a heavy chain CDR 3, the variable light domain comprising a light chain CDR 1, a light chain CDR 2 and a light chain CDR 3, wherein (a) Heavy Chain CDR 1 has an amino acid sequence of: Gly-Phe-Thr-Phe-Ser-Ser-Tyr-Gly-Met-Ser (SEQ ID NO: 2);

(b) Heavy Chain CDR 2 has an amino acid sequence having a formula of: Thr-Ile-Ser-Ser-Gly-Gly-Ala-Trp-Thr-Phe (SEQ ID NO: 16);

(c) Heavy Chain CDR 3 has an amino acid sequence of: Gln-Thr-Asp-Gly-Tyr-Ser-Trp-Phe-Pro-Tyr (SEQ ID NO: 6);

(d) Light Chain CDR 1 has an amino acid sequence having a formula of: Lys-Ser-Ser-Gln-Gly-Leu-Val-His-Ser-Thr-Gly-Asn-Thr-Phe-Leu-Glu (SEQ ID NO: 22);

(e) Light Chain CDR 2 has an amino acid sequence having the formula of: Lys-Ile-Ser-Asn-Arg-Phe-Ser (SEQ ID NO: 11);

(f) Light Chain CDR 3 has an amino acid sequence having a formula of: Phe-Gln-Gly-Ser-His-Ala-Pro-Leu-Thr (SEQ ID NO: 23);

(g) Heavy Chain framework region FR1 has an amino acid sequence having a formula of: Glu-Val-Glu-Leu-Val-Glu-Ser-Gly-Gly-Asp-Leu-Val-Lys-Pro-Gly-Gly-Ser-Leu-Lys-Leu-Ser-Cys-Ala-Ala-Ser (SEQ ID NO: 1);

(h) Heavy Chain framework region FR2 has an amino acid sequence having a formula of: Trp-Val-Arg-Gln-Thr-Pro-Asp-Lys-Arg-Leu-Glu-Trp-Val-Ala (SEQ ID NO: 3);

(i) Heavy Chain framework region FR3 has an amino acid sequence having a formula of: Tyr-Pro-Asp-Ser-Val-Lys-Gly-Arg-Phe-Thr-Ile-Ser-Arg-Asp-Asn-Ala-Lys-Asn-Thr-Leu-Ser-Leu-Gln-Met-Ser-Ser-Leu-Lys-Ser-Ala-Asp-Thr-Ala-Met-Tyr-Tyr-Cys-Ser-Arg (SEQ ID NO: 5);

(j) Heavy Chain framework region FR4 has an amino acid sequence having a formula of: Trp-Gly-Gln-Gly-Thr-Leu-Val-Thr-Val-Ser-Ala (SEQ ID NO: 7);

(k) Light Chain framework region FR1 has an amino acid sequence having a formula of: Asp-Val-Leu-Met-Thr-Gln-Thr-Pro-Leu-Ser-Leu-Pro-Val-Ser-Leu-Gly-Asp-Gln-Ala-Ser-Ile-Ser-Cys (SEQ ID NO: 8);

(l) Light Chain framework region FR2 has an amino acid sequence having a formula of: Trp-Phe-Leu-Gln-Lys-Pro-Gly-Gln-Ser-Pro-Lys-Leu-Leu-Ile-Tyr (SEQ ID NO: 10);

(m) Light Chain framework region FR3 has an amino acid sequence having a formula of: Gly-Val-Pro-Asp-Arg-Phe-Ser-Gly-Ser-Gly-Ser-Gly-Thr-Asp-Phe-Thr-Leu-Lys-Ile-Ser-Arg-Val-Glu-Ser-Glu-Asp-Leu-Gly-Val-Tyr-Tyr-Cys (SEQ ID NO: 12); and (n) Light Chain framework region FR4 has an amino acid sequence having a formula of: Phe-Gly-Ala-Gly-Thr-Lys-Leu-Glu-Leu-Lys-Arg-Ala (SEQ ID NO: 14).

7. An isolated recombinant antibody which specifically binds to tacrolimus, wherein said antibody has a variable heavy domain and a variable light domain, the variable heavy domain comprising an amino acid sequence having a formula of: Glu-Val-Glu-Leu-Val-Glu-Ser-Gly-Gly-Asp-Leu-Val-Lys-Pro-Gly-Gly-Ser-Leu-Lys-Leu-Ser-Cys-Ala-Ala-Ser-Gly-Phe-Thr-Phe-Ser-Ser-Tyr-Gly-Met-Ser-Trp-Val-Arg-Gln-Thr-Pro-Asp-Lys-Arg-Leu-Glu-Trp-Val-Ala-Thr-Ile-Ser-Ser-Gly-Gly-Ala-Trp-Thr-Phe-Tyr-Pro-Asp-Ser-Val-Lys-Gly-Arg-Phe-Thr-Ile-Ser-Arg-Asp-Asn-Ala-Lys-Asn-Thr-Leu-Ser-Leu-Gln-Met-Ser-Ser-Leu-Lys-Ser-Ala-Asp-Thr-Ala-Met-Tyr-Tyr-Cys-Ser-Arg-Gln-Thr-Asp-Gly-Tyr-Ser-Trp-Phe-Pro-Tyr-Trp-Gly-Gln-Gly-Thr-Leu-Val-Thr-Val-Ser-Ala-Ser-Ala-Lys-Thr-Thr-Ala-Pro-Ser-Val-Tyr-Pro-Leu-Ala-Pro-Val-Cys-Gly-Asp-Thr-Thr-Gly-Ser-Ser-Val-Thr-Leu-Gly-Cys-Leu-Val-Lys-Gly-Tyr-Phe-Pro-Glu-Pro-Val-Thr-Leu-Thr-Trp-Asn-Ser-Gly-Ser-Leu-Ser-Ser-Gly-Val-His-Thr-Phe-Pro-Ala-Val-Leu-Gln-Ser-Asp-Leu-Tyr-Thr-Leu-Ser-Ser-Ser-Val-Thr-Val-Thr-Ser-Ser-Thr-Trp-Pro-Ser-Gln-Ser-Ile-Thr-Cys-Asn-Val-Ala-His-Pro-Ala-Ser-Ser-Thr-Lys-Val-Asp-Lys-Lys-Ile-Glu-Pro-Arg-Gly-Pro-Thr-Ile-Lys-Pro-Cys-Pro-Pro-Cys-Lys-Cys-Pro-Ala-Pro-Asn-Leu-Leu-Gly-Gly-Pro-Ser-Val-Phe-Ile-Phe-Pro-Pro-Lys-Ile-Lys-Asp-Val-Leu-Met-Ile-Ser-Leu-Ser-Pro-Ile-Val-Thr-Cys-Val-Val-Val-Asp-Val-Ser-Glu-Asp-Asp-Pro-Asp-Val-Gln-Ile-Ser-Trp-Phe-Val-Asn-Asn-Val-Glu-Val-His-Thr-Ala-Gln-Thr-Gln-Thr-His-Arg-Glu-Asp-Tyr-Asn-Ser-Thr-Leu-Arg-Val-Val-Ser-Ala-Leu-Pro-Ile-Gln-His-Gln-Asp-Trp-Met-Ser-Gly-Lys-Glu-Phe-Lys-Cys-Lys-Val-Asn-Asn-Lys-Asp-Leu-Pro-Ala-Pro-Ile-Glu-Arg-Thr-Ile-Ser-Lys-Pro-Lys-Gly-Ser-Val-Arg-Ala-Pro-Gln-Val-Tyr-Val-Leu-Pro-Pro-Pro-Glu-Glu-Glu-Met-Thr-Lys-Lys-Gln-Val-Thr-Leu-Thr-Cys-Met-Val-Thr-Asp-Phe-Met-Pro-Glu-Asp-Ile-Tyr-Val-Glu-Trp-Thr-Asn-Asn-Gly-Lys-Thr-Glu-Leu-Asn-Tyr-Lys-Asn-Thr-Glu-Pro-Val-Leu-Asp-Ser-Asp-Gly-Ser-Tyr-Phe-Met-Tyr-Ser-Lys-Leu-Arg-Val-Glu-Lys-Lys-Asn-Trp-Val-Glu-Arg-Asn-Ser-Tyr-Ser-Cys-Ser-Val-Val-His-Glu-Gly-Leu-His-Asn-His-His-Thr-Thr-Lys-Ser-Phe-Ser-Arg-Thr-Pro-Gly-Lys (SEQ ID NO: 40)

and the variable light domain comprising an amino acid sequence having a formula of: Asp-Val-Leu-Met-Thr-Gln-Thr-Pro-Leu-Ser-Leu-Pro-Val-Ser-Leu-Gly-Asp-Gln-Ala-Ser-Ile-Ser-Cys-Lys-Ser-Ser-Gln-Gly-Leu-Val-His-Ser-Thr-Gly-Asn-Thr-Phe-Leu-Glu-Trp-Phe-Leu-Gln-Lys-Pro-Gly-Gln-Ser-Pro-Lys-Leu-Leu-Ile-Tyr-Lys-Ile-Ser-Asn-Arg-Phe-Ser-Gly-Val-Pro-Asp-Arg-Phe-Ser-Gly-Ser-Gly-Ser-Gly-Thr-Asp-Phe-Thr-Leu-Lys-Ile-Ser-Arg-Val-Glu-Ser-Glu-Asp-Leu-Gly-Val-Tyr-Tyr-Cys-Phe-Gln-Gly-Ser-His-Ala-Pro-Leu-Thr-Phe-Gly-Ala-Gly-Thr-Lys-Leu-Glu-Leu-Lys-Arg-Ala-Ser-Ala-Asp-Ala-Ala-Pro-Thr-Val-Ser-Ile-Phe-Pro-Pro-Ser-Ser-Glu-Gln-Leu-Thr-Ser-Gly-Gly-Ala-Ser-Val-Val-Cys-Phe-Leu-Asn-Asn-Phe-Tyr-Pro-Lys-Asp-Ile-Asn-Val-Lys-Trp-Lys-Ile-Asp-Gly-Ser-Glu-Arg-Gln-Asn-Gly-Val-Leu-Asn-Ser-Trp-Thr-Asp-Gln-Asp-Ser-Lys-Asp-Ser-Thr-Tyr-Ser-Met-Ser-Ser-Thr-Leu-Thr-Leu-Thr-Lys-Asp-Glu-Tyr-Glu-Arg-His-Asn-Ser-Tyr-Thr-Cys-Glu-Ala-Thr-His-Lys-Thr-Ser-Thr-Ser-Pro-Ile-Val-Lys-Ser-Phe-Asn-Arg-Asn-Glu-Cys (SEQ ID NO: 42).

* * * * *